(12) United States Patent
Windmiller et al.

(10) Patent No.: US 11,857,344 B2
(45) Date of Patent: Jan. 2, 2024

(54) FAULT DETECTION FOR MICRONEEDLE ARRAY BASED CONTINUOUS ANALYTE MONITORING DEVICE

(71) Applicant: Biolinq Incorporated, San Diego, CA (US)

(72) Inventors: Joshua Ray Windmiller, San Diego, CA (US); Alan Steven Campbell, San Diego, CA (US); Jared Rylan Tangney, Encinitas, CA (US)

(73) Assignee: Biolinq Incorporated, San Diego, CA (US)

( * ) Notice: Subject to any disclaimer, the term of this patent is extended or adjusted under 35 U.S.C. 154(b) by 0 days.

(21) Appl. No.: 17/738,990

(22) Filed: May 6, 2022

(65) Prior Publication Data
US 2022/0370011 A1 Nov. 24, 2022

Related U.S. Application Data

(60) Provisional application No. 63/186,086, filed on May 8, 2021.

(51) Int. Cl.
*A61B 5/145* (2006.01)
*A61B 5/00* (2006.01)

(52) U.S. Cl.
CPC .......... *A61B 5/685* (2013.01); *A61B 5/14514* (2013.01); *A61B 5/14532* (2013.01)

(58) Field of Classification Search
CPC . A61B 5/14514; A61B 5/14532; A61B 5/685; A61B 2562/046; A61B 2562/125; A61B 5/14503; A61B 5/7225
See application file for complete search history.

(56) References Cited

U.S. PATENT DOCUMENTS 4,305,401 A 12/1981 Reissmueller et al.
4,323,996 A 4/1982 Ganter
(Continued)

FOREIGN PATENT DOCUMENTS

CN 101068591 A 11/2007
CN 112617822 A 4/2021
(Continued)

OTHER PUBLICATIONS

Abbot press release (2020). "New late-breaking data show use of abbott's Freestyle® Libre System significantly reduces HBA1C levels in people with type 2 diabetes using insulin or not," 3 pages.
(Continued)

*Primary Examiner* — Eric J Messersmith
(74) *Attorney, Agent, or Firm* — Cooley LLP

(57) ABSTRACT

Fault detection and diagnostics for a microneedle array based continuous analyte monitoring device are provided. The electrochemical sensors, including the electrodes of the analyte monitoring device configured for measuring one or more target analytes, may experience various faults during use of the analyte monitoring device. By modeling the sensors as an electrical network, measurements of the electrical network may be correlated with operational parameters of the sensor. The voltage at the counter electrode provides an indication of the resistance or impedance between the working electrode and the counter electrode and is used to identify the occurrence of faults occurring at the continuous analyte monitoring device.

20 Claims, 20 Drawing Sheets

(56) References Cited

U.S. PATENT DOCUMENTS

| | | |
|---|---|---|
| 4,407,295 A | 10/1983 | Steuer et al. |
| 4,450,842 A | 5/1984 | Zick et al. |
| 4,908,117 A | 3/1990 | Kinlen et al. |
| 4,969,468 A | 11/1990 | Byers et al. |
| 5,035,711 A | 7/1991 | Aoki et al. |
| 5,131,390 A | 7/1992 | Sakaguchi et al. |
| 5,279,543 A | 1/1994 | Glikfeld et al. |
| 5,286,364 A | 2/1994 | Yacynych et al. |
| 5,540,828 A | 7/1996 | Yacynych |
| 5,730,714 A | 3/1998 | Guy et al. |
| 5,766,132 A | 6/1998 | Yasukawa et al. |
| 5,832,410 A | 11/1998 | Lin et al. |
| 5,869,078 A | 2/1999 | Baudino |
| 5,953,306 A | 9/1999 | Yi |
| 6,036,055 A | 3/2000 | Mogadam et al. |
| 6,091,975 A | 7/2000 | Daddona et al. |
| 6,132,449 A | 10/2000 | Lum et al. |
| 6,132,499 A | 10/2000 | Wong et al. |
| 6,132,755 A | 10/2000 | Eicher et al. |
| 6,139,718 A | 10/2000 | Kurnik et al. |
| 6,269,053 B1 | 7/2001 | Kawata et al. |
| 6,284,126 B1 | 9/2001 | Kurnik et al. |
| 6,364,890 B1 | 4/2002 | Lum et al. |
| 6,413,396 B1 | 7/2002 | Yang et al. |
| 6,465,091 B1 | 10/2002 | Ou-yang |
| 6,471,903 B2 | 10/2002 | Sherman et al. |
| 6,527,762 B1 | 3/2003 | Santini, Jr. et al. |
| 6,551,849 B1 | 4/2003 | Kenney |
| 6,587,705 B1 | 7/2003 | Kim et al. |
| 6,599,408 B1 | 7/2003 | Chan et al. |
| 6,603,987 B2 | 8/2003 | Whitson |
| 6,611,707 B1 | 8/2003 | Prausnitz et al. |
| 6,793,789 B2 | 9/2004 | Choi et al. |
| 6,801,041 B2 | 10/2004 | Karinka et al. |
| 6,814,845 B2 | 11/2004 | Wilson et al. |
| 6,862,466 B2 | 3/2005 | Ackerman |
| 6,908,453 B2 | 6/2005 | Fleming et al. |
| 7,081,195 B2 | 7/2006 | Simpson et al. |
| 7,097,776 B2 | 8/2006 | Govinda Raju |
| 7,132,054 B1 | 11/2006 | Kravitz et al. |
| 7,262,068 B2 | 8/2007 | Roy et al. |
| 7,343,188 B2 | 3/2008 | Sohrab |
| 7,344,499 B1 | 3/2008 | Prausnitz et al. |
| 7,366,556 B2 | 4/2008 | Brister et al. |
| 7,415,299 B2 | 8/2008 | Zimmermann et al. |
| 7,429,333 B2 | 9/2008 | Chiou et al. |
| 7,456,112 B2 | 11/2008 | Lee |
| 7,471,972 B2 | 12/2008 | Rhodes et al. |
| 7,473,244 B2 | 1/2009 | Frazier et al. |
| 7,493,232 B1 | 2/2009 | Surina |
| 7,534,330 B2 | 5/2009 | Yu et al. |
| 7,583,990 B2 | 9/2009 | Goode, Jr. |
| 7,599,726 B2 | 10/2009 | Goode, Jr. |
| 7,613,491 B2 | 11/2009 | Boock |
| 7,645,263 B2 | 1/2010 | Angel et al. |
| 7,715,893 B2 | 5/2010 | Kamath et al. |
| 7,768,408 B2 | 8/2010 | Reggiardo et al. |
| 7,778,680 B2 | 8/2010 | Goode, Jr. |
| 7,797,028 B2 | 9/2010 | Goode, Jr. |
| 7,811,231 B2 | 10/2010 | Jin et al. |
| 7,837,654 B2 | 11/2010 | Shumate et al. |
| 7,885,697 B2 | 2/2011 | Brister et al. |
| 7,905,833 B2 | 3/2011 | Brister et al. |
| 7,917,186 B2 | 3/2011 | Kamath et al. |
| 7,949,382 B2 | 5/2011 | Jina |
| 7,959,569 B2 | 6/2011 | Goode et al. |
| 8,005,526 B2 | 8/2011 | Martin et al. |
| 8,010,174 B2 | 8/2011 | Goode, Jr. |
| 8,022,292 B2 | 9/2011 | Arianpour et al. |
| 8,064,977 B2 | 11/2011 | Boock et al. |
| 8,088,321 B2 | 1/2012 | Ferguson et al. |
| 8,094,009 B2 | 1/2012 | Allen et al. |
| 8,108,023 B2 | 1/2012 | Mir et al. |
| 8,110,079 B2 | 2/2012 | Gooding et al. |
| 8,125,331 B2 | 2/2012 | Allen et al. |
| 8,130,095 B2 | 3/2012 | Allen et al. |
| 8,160,665 B2 | 4/2012 | Mischler et al. |
| 8,160,671 B2 | 4/2012 | Kamath et al. |
| 8,160,834 B2 | 4/2012 | Liang et al. |
| 8,162,901 B2 | 4/2012 | Gonnelli et al. |
| RE43,399 E | 5/2012 | Simpson et al. |
| 8,216,138 B1 | 7/2012 | McGarraugh |
| 8,236,368 B2 | 8/2012 | Jung et al. |
| 8,249,684 B2 | 8/2012 | Kamath et al. |
| 8,257,324 B2 | 9/2012 | Prausnitz et al. |
| 8,280,475 B2 | 10/2012 | Brister et al. |
| 8,280,476 B2 | 10/2012 | Jina |
| 8,284,046 B2 | 10/2012 | Allen et al. |
| 8,287,453 B2 | 10/2012 | Li et al. |
| 8,308,960 B2 | 11/2012 | Kälvesten et al. |
| 8,346,335 B2 | 1/2013 | Harper et al. |
| 8,376,945 B2 | 2/2013 | Hayter et al. |
| 8,386,004 B2 | 2/2013 | Kamath et al. |
| 8,423,114 B2 | 4/2013 | Simpson et al. |
| 8,428,678 B2 | 4/2013 | Kamath et al. |
| 8,452,369 B2 | 5/2013 | Huys et al. |
| 8,463,350 B2 | 6/2013 | Kamath et al. |
| 8,483,793 B2 | 7/2013 | Simpson et al. |
| 8,506,529 B1 | 8/2013 | Yang |
| 8,548,553 B2 | 10/2013 | Kamath et al. |
| 8,565,848 B2 | 10/2013 | Brister et al. |
| 8,574,165 B2 | 11/2013 | Marsh |
| 8,617,069 B2 | 12/2013 | Bernstein et al. |
| RE44,695 E | 1/2014 | Simpson et al. |
| 8,626,257 B2 | 1/2014 | Li et al. |
| 8,637,351 B2 | 1/2014 | Kälvesten et al. |
| 8,660,628 B2 | 2/2014 | Wang et al. |
| 8,708,966 B2 | 4/2014 | Allen et al. |
| 8,798,799 B2 | 8/2014 | Deo et al. |
| 8,815,070 B2 | 8/2014 | Wang et al. |
| 8,870,763 B2 | 10/2014 | Yang et al. |
| 8,882,665 B2 | 11/2014 | Yang et al. |
| 9,008,743 B2 | 4/2015 | Hayter et al. |
| 9,008,745 B2 | 4/2015 | Pushpala et al. |
| 9,055,901 B2 | 6/2015 | Brister et al. |
| 9,125,625 B2 | 9/2015 | Wang et al. |
| 9,182,368 B2 | 11/2015 | Pushpala et al. |
| 9,234,872 B2 | 1/2016 | Homyk et al. |
| 9,248,273 B2 | 2/2016 | Guvanasen et al. |
| 9,332,934 B2 | 5/2016 | Hayter et al. |
| 9,336,423 B2 | 5/2016 | Goodnow et al. |
| 9,357,951 B2 | 6/2016 | Simpson et al. |
| 9,386,954 B2 | 7/2016 | Saini et al. |
| 9,387,000 B2 | 7/2016 | Corrie et al. |
| 9,414,778 B2 | 8/2016 | Mao et al. |
| 9,420,965 B2 | 8/2016 | Brauker et al. |
| 9,532,741 B2 | 1/2017 | Brauker et al. |
| 9,551,698 B2 | 1/2017 | Huys et al. |
| 9,662,056 B2 | 5/2017 | Budiman et al. |
| 9,737,247 B2 | 8/2017 | Wang et al. |
| 9,743,870 B2 | 8/2017 | Wang et al. |
| 9,743,871 B2 | 8/2017 | Simpson et al. |
| 9,757,061 B2 | 9/2017 | Shults et al. |
| 9,770,211 B2 | 9/2017 | Hayter et al. |
| 9,804,114 B2 | 10/2017 | Rhodes et al. |
| 9,933,387 B1 | 4/2018 | McCanna et al. |
| 9,958,409 B2 | 5/2018 | Gerber et al. |
| 10,022,076 B2 | 7/2018 | Hoss et al. |
| 10,039,480 B2 | 8/2018 | Brauker et al. |
| 10,046,114 B1 | 8/2018 | Biederman et al. |
| 10,052,055 B2 | 8/2018 | Li et al. |
| 10,092,207 B1 | 10/2018 | Windmiller |
| 10,136,846 B2 | 11/2018 | Wang et al. |
| 10,173,042 B2 | 1/2019 | Pushpala et al. |
| 10,182,748 B2 | 1/2019 | Catt et al. |
| 10,188,333 B2 | 1/2019 | Kamath et al. |
| 10,228,341 B2 | 3/2019 | Katsuki et al. |
| 10,299,712 B2 | 5/2019 | Brister et al. |
| 10,327,678 B2 | 6/2019 | Gottlieb et al. |
| 10,492,708 B1 | 12/2019 | Windmiller |
| D875,254 S | 2/2020 | Cooke et al. |
| 10,549,080 B2 | 2/2020 | Pushpala et al. |
| 10,610,103 B2 | 4/2020 | Brister et al. |
| 10,709,332 B2 | 7/2020 | Brister et al. |

(56) References Cited

U.S. PATENT DOCUMENTS

| | | |
|---|---|---|
| 10,743,800 B2 | 8/2020 | Larvenz et al. |
| 10,820,860 B2 | 11/2020 | Pushpala et al. |
| 10,881,334 B2 | 1/2021 | Facchinetti et al. |
| 10,932,700 B2 | 3/2021 | Simpson et al. |
| 10,983,083 B2 | 4/2021 | Harding et al. |
| 11,020,026 B2 | 6/2021 | Boock et al. |
| 11,035,872 B2 | 6/2021 | Boutelle et al. |
| 11,045,142 B1 | 6/2021 | Windmiller et al. |
| 11,051,724 B2 | 7/2021 | Pace et al. |
| 11,123,532 B2 | 9/2021 | Pushpala et al. |
| 11,179,068 B2 | 11/2021 | Pace et al. |
| 11,197,985 B2 | 12/2021 | Pushpala et al. |
| 11,272,866 B2 | 3/2022 | Pushpala et al. |
| 11,272,885 B2 | 3/2022 | Pushpala et al. |
| 11,291,390 B2 | 4/2022 | Pushpala et al. |
| 11,331,022 B2 | 5/2022 | Halac et al. |
| 11,359,300 B1 | 6/2022 | Beer et al. |
| 11,406,818 B2 | 8/2022 | Windmiller |
| 11,478,194 B2 | 10/2022 | Windmiller et al. |
| 11,596,332 B2 | 3/2023 | Shults et al. |
| 11,654,270 B2 | 5/2023 | Mansfield, III et al. |
| D988,160 S | 6/2023 | Morelock |
| 11,672,965 B2 | 6/2023 | Mansfield, III et al. |
| D996,999 S | 8/2023 | Morelock |
| 2002/0004640 A1 | 1/2002 | Conn et al. |
| 2002/0020688 A1 | 2/2002 | Sherman et al. |
| 2002/0055704 A1 | 5/2002 | Scott et al. |
| 2002/0072784 A1 | 6/2002 | Norman, Jr. et al. |
| 2002/0105080 A1 | 8/2002 | Speakman |
| 2002/0187556 A1 | 12/2002 | Shartle et al. |
| 2003/0088166 A1 | 5/2003 | Say et al. |
| 2003/0095582 A1 | 5/2003 | Ackley |
| 2003/0100040 A1 | 5/2003 | Bonnecaze et al. |
| 2003/0104119 A1 | 6/2003 | Wilson et al. |
| 2003/0135158 A1 | 7/2003 | Gonnelli |
| 2003/0208167 A1 | 11/2003 | Prausnitz et al. |
| 2003/0225360 A1 | 12/2003 | Eppstein et al. |
| 2003/0235817 A1 | 12/2003 | Bartkowiak et al. |
| 2004/0065158 A1 | 4/2004 | Schrepfer et al. |
| 2004/0082875 A1 | 4/2004 | Donoghue et al. |
| 2004/0220625 A1 | 11/2004 | Silvestri et al. |
| 2005/0036020 A1 | 2/2005 | Li et al. |
| 2005/0137536 A1 | 6/2005 | Gonnelli |
| 2005/0209565 A1 | 9/2005 | Yuzhakov et al. |
| 2005/0267440 A1 | 12/2005 | Herman et al. |
| 2005/0272989 A1 | 12/2005 | Shah et al. |
| 2006/0015061 A1 | 1/2006 | Kuo et al. |
| 2006/0016700 A1 | 1/2006 | Brister et al. |
| 2006/0173259 A1 | 8/2006 | Flaherty et al. |
| 2006/0264716 A1 | 11/2006 | Zander |
| 2006/0281121 A1 | 12/2006 | Unger et al. |
| 2007/0078445 A1 | 4/2007 | Malloy |
| 2007/0169533 A1 | 7/2007 | Shah et al. |
| 2007/0170054 A2 | 7/2007 | Wilsey |
| 2007/0213044 A1 | 9/2007 | Steingart et al. |
| 2007/0282246 A1 | 12/2007 | Henley |
| 2008/0009800 A1 | 1/2008 | Nickel |
| 2008/0009801 A1 | 1/2008 | Nickel |
| 2008/0027369 A1 | 1/2008 | Carter et al. |
| 2008/0033269 A1 | 2/2008 | Zhang |
| 2008/0097280 A1 | 4/2008 | Martin et al. |
| 2008/0097352 A1 | 4/2008 | Beck et al. |
| 2008/0119707 A1 | 5/2008 | Stafford |
| 2008/0154107 A1 | 6/2008 | Jina |
| 2008/0156661 A1 | 7/2008 | Cooper et al. |
| 2008/0213461 A1 | 9/2008 | Gill et al. |
| 2008/0221408 A1 | 9/2008 | Hoarau et al. |
| 2008/0234562 A1 | 9/2008 | Jina |
| 2008/0255434 A1 | 10/2008 | Hayter et al. |
| 2008/0275327 A1 | 11/2008 | Faarbaek et al. |
| 2009/0057148 A1* | 3/2009 | Wieder ............ A61B 5/14532 |
| | | 205/792 |
| 2009/0066348 A1 | 3/2009 | Shin et al. |
| 2009/0069651 A1 | 3/2009 | Zimmermann et al. |
| 2009/0069697 A1 | 3/2009 | Frazier et al. |
| 2009/0084678 A1 | 4/2009 | Joshi et al. |
| 2009/0088652 A1 | 4/2009 | Tremblay |
| 2009/0090623 A1 | 4/2009 | Chuang et al. |
| 2009/0099427 A1 | 4/2009 | Jina et al. |
| 2009/0101498 A1 | 4/2009 | Papadimitrakopoulos et al. |
| 2009/0131778 A1 | 5/2009 | Jina et al. |
| 2009/0143761 A1 | 6/2009 | Cantor et al. |
| 2009/0152598 A1 | 6/2009 | Baek et al. |
| 2009/0191616 A1 | 7/2009 | Lu et al. |
| 2009/0198118 A1 | 8/2009 | Hayter et al. |
| 2009/0218239 A1 | 9/2009 | Gooding et al. |
| 2009/0259118 A1 | 10/2009 | Feldman et al. |
| 2009/0294306 A1 | 12/2009 | Feldman et al. |
| 2010/0006451 A1 | 1/2010 | Gordon et al. |
| 2010/0021637 A1 | 1/2010 | Revol et al. |
| 2010/0025238 A1 | 2/2010 | Gottlieb et al. |
| 2010/0030045 A1 | 2/2010 | Gottlieb et al. |
| 2010/0049021 A1 | 2/2010 | Jina et al. |
| 2010/0052892 A1 | 3/2010 | Allen et al. |
| 2010/0052897 A1 | 3/2010 | Allen et al. |
| 2010/0052898 A1 | 3/2010 | Allen et al. |
| 2010/0052915 A1 | 3/2010 | Allen et al. |
| 2010/0056873 A1 | 3/2010 | Allen et al. |
| 2010/0137779 A1 | 6/2010 | Seitz |
| 2010/0200538 A1 | 8/2010 | Petisce et al. |
| 2010/0279377 A1 | 11/2010 | Shah et al. |
| 2010/0286803 A1 | 11/2010 | Tillotson et al. |
| 2011/0027127 A1 | 2/2011 | Simpson et al. |
| 2011/0077490 A1 | 3/2011 | Simpson et al. |
| 2011/0105871 A1 | 5/2011 | Zimmermann et al. |
| 2011/0140703 A1 | 6/2011 | Chiao et al. |
| 2011/0224515 A1 | 9/2011 | Mir et al. |
| 2011/0230736 A1 | 9/2011 | Tepper et al. |
| 2011/0237925 A1 | 9/2011 | Yue et al. |
| 2011/0247934 A1 | 10/2011 | Wang et al. |
| 2011/0275918 A1 | 11/2011 | Yamashita et al. |
| 2011/0306853 A1 | 12/2011 | Black et al. |
| 2011/0319787 A1 | 12/2011 | Lamoise et al. |
| 2012/0018302 A1 | 1/2012 | Shiraki et al. |
| 2012/0037515 A1 | 2/2012 | Solanki |
| 2012/0067734 A1 | 3/2012 | Wang et al. |
| 2012/0078071 A1 | 3/2012 | Bohm et al. |
| 2012/0123232 A1 | 5/2012 | Najarian et al. |
| 2012/0172692 A1 | 7/2012 | Tamada et al. |
| 2012/0209244 A1 | 8/2012 | Gray |
| 2012/0277629 A1 | 11/2012 | Bernstein et al. |
| 2012/0323097 A9 | 12/2012 | Chowdhury |
| 2013/0053660 A1 | 2/2013 | Shieh |
| 2013/0065257 A1 | 3/2013 | Wang et al. |
| 2013/0135158 A1 | 5/2013 | Faraone et al. |
| 2013/0144131 A1 | 6/2013 | Wang et al. |
| 2013/0158376 A1 | 6/2013 | Hayter et al. |
| 2013/0225956 A1 | 8/2013 | Huang et al. |
| 2013/0281808 A1 | 10/2013 | Shieh |
| 2013/0338746 A1 | 12/2013 | Guvanasen et al. |
| 2013/0345597 A1 | 12/2013 | Hagino et al. |
| 2014/0135679 A1 | 5/2014 | Mann et al. |
| 2014/0259652 A1 | 9/2014 | Pushpala et al. |
| 2014/0275897 A1 | 9/2014 | Pushpala et al. |
| 2014/0275899 A1 | 9/2014 | Gottlieb et al. |
| 2014/0275907 A1 | 9/2014 | Feldman et al. |
| 2014/0303471 A1 | 10/2014 | Rajaraman et al. |
| 2014/0336487 A1 | 11/2014 | Wang et al. |
| 2014/0378804 A1 | 12/2014 | Kalvesten et al. |
| 2015/0073238 A1 | 3/2015 | Matsumoto et al. |
| 2015/0126834 A1 | 5/2015 | Wang et al. |
| 2015/0208970 A1 | 7/2015 | Huang |
| 2015/0243851 A1 | 8/2015 | Lee et al. |
| 2015/0276758 A1 | 10/2015 | Addisu |
| 2015/0313527 A1 | 11/2015 | Renlund |
| 2016/0029937 A1 | 2/2016 | Sia et al. |
| 2016/0058342 A1 | 3/2016 | Maiz-Aguinaga et al. |
| 2016/0095541 A1 | 4/2016 | Wang et al. |
| 2016/0095547 A1 | 4/2016 | Wang et al. |
| 2016/0139069 A1 | 5/2016 | Wang |
| 2016/0157764 A1 | 6/2016 | Di Palma et al. |
| 2016/0158514 A1 | 6/2016 | Stoeber et al. |
| 2016/0166184 A1 | 6/2016 | Teng et al. |
| 2016/0258945 A1 | 9/2016 | Malima et al. |

(56) References Cited

U.S. PATENT DOCUMENTS

| | | |
|---|---|---|
| 2016/0270704 A1 | 9/2016 | Deturk |
| 2016/0296149 A1 | 10/2016 | Polsky et al. |
| 2016/0302687 A1 | 10/2016 | Lee et al. |
| 2016/0370377 A1 | 12/2016 | Ahmad |
| 2017/0003766 A1 | 1/2017 | Budiman |
| 2017/0007813 A1 | 1/2017 | Negi et al. |
| 2017/0035331 A1 | 2/2017 | Parajape et al. |
| 2017/0086713 A1 | 3/2017 | Pushpala et al. |
| 2017/0127989 A1 | 5/2017 | Feldman et al. |
| 2017/0128009 A1 | 5/2017 | Pushpala et al. |
| 2017/0164881 A1* | 6/2017 | Fujita .................. A61B 5/1486 |
| 2017/0251959 A1 | 9/2017 | Feldman et al. |
| 2017/0251960 A1 | 9/2017 | Crouther et al. |
| 2017/0347925 A1 | 12/2017 | Wang et al. |
| 2018/0116572 A1 | 5/2018 | Simpson et al. |
| 2018/0140235 A1 | 5/2018 | Pushpala et al. |
| 2018/0279929 A1 | 10/2018 | Huang et al. |
| 2018/0317820 A1 | 11/2018 | Pace et al. |
| 2018/0338712 A1 | 11/2018 | Cass et al. |
| 2019/0008425 A1 | 1/2019 | Srinivasan et al. |
| 2019/0022365 A1 | 1/2019 | Chowdhury et al. |
| 2019/0029577 A1 | 1/2019 | Koelker et al. |
| 2019/0090811 A1 | 3/2019 | Reitz et al. |
| 2019/0091455 A1 | 3/2019 | Reitz et al. |
| 2019/0094169 A1 | 3/2019 | Shah et al. |
| 2019/0110724 A1 | 4/2019 | Kamath et al. |
| 2019/0125223 A1 | 5/2019 | Wang et al. |
| 2019/0167167 A1 | 6/2019 | Mitchell et al. |
| 2019/0209095 A1 | 7/2019 | Kamath et al. |
| 2019/0223795 A1 | 7/2019 | Patolsky et al. |
| 2019/0224712 A1 | 7/2019 | Petisce et al. |
| 2019/0241926 A1 | 8/2019 | Mckinlay et al. |
| 2019/0261907 A1 | 8/2019 | Brister et al. |
| 2019/0274599 A1 | 9/2019 | Polsky et al. |
| 2019/0274600 A1 | 9/2019 | Pesantez et al. |
| 2019/0298210 A1 | 10/2019 | Bennet et al. |
| 2019/0307379 A1 | 10/2019 | Boock et al. |
| 2019/0309433 A1 | 10/2019 | Sattayasamitsathit et al. |
| 2019/0310219 A1 | 10/2019 | Boock |
| 2019/0357827 A1 | 11/2019 | Li et al. |
| 2020/0029876 A1 | 1/2020 | Brister et al. |
| 2020/0037938 A1 | 2/2020 | Rong et al. |
| 2020/0085341 A1 | 3/2020 | Windmiller |
| 2020/0101286 A1 | 4/2020 | Windmiller et al. |
| 2020/0121902 A1 | 4/2020 | Pushpala et al. |
| 2020/0178853 A1 | 6/2020 | Pushpala et al. |
| 2020/0187778 A1 | 6/2020 | Brister et al. |
| 2020/0214566 A1 | 7/2020 | Allen et al. |
| 2020/0254240 A1 | 8/2020 | Windmiller et al. |
| 2020/0297997 A1 | 9/2020 | Windmiller et al. |
| 2020/0305771 A1 | 10/2020 | Feldman et al. |
| 2020/0359949 A1 | 11/2020 | Brauker et al. |
| 2020/0405234 A1 | 12/2020 | Pushpala et al. |
| 2021/0045663 A1 | 2/2021 | Simpson et al. |
| 2021/0045665 A1 | 2/2021 | Simpson et al. |
| 2021/0045666 A1 | 2/2021 | Simpson et al. |
| 2021/0100452 A1 | 4/2021 | Brister et al. |
| 2021/0100504 A1 | 4/2021 | Pushpala et al. |
| 2021/0100505 A1 | 4/2021 | Pushpala et al. |
| 2021/0183508 A1 | 6/2021 | Parker et al. |
| 2021/0187286 A1 | 6/2021 | Windmiller et al. |
| 2021/0190719 A1 | 6/2021 | LaTour et al. |
| 2021/0345916 A1 | 11/2021 | Boock et al. |
| 2021/0353229 A1 | 11/2021 | Pierart et al. |
| 2021/0379370 A1 | 12/2021 | Windmiller et al. |
| 2021/0386338 A1 | 12/2021 | Zhang et al. |
| 2021/0393201 A1 | 12/2021 | Morelock et al. |
| 2022/0031244 A1 | 2/2022 | Windmiller et al. |
| 2022/0047190 A1 | 2/2022 | Taylor et al. |
| 2022/0054813 A1 | 2/2022 | Pushpala et al. |
| 2022/0054814 A1 | 2/2022 | Pushpala et al. |
| 2022/0104773 A1 | 4/2022 | Lee et al. |
| 2022/0151516 A1 | 5/2022 | Wang et al. |
| 2022/0151518 A1 | 5/2022 | Pushpala et al. |
| 2022/0151519 A1 | 5/2022 | Pushpala et al. |
| 2022/0151558 A1 | 5/2022 | Pushpala et al. |
| 2022/0175278 A1 | 6/2022 | Campbell et al. |
| 2022/0175279 A1 | 6/2022 | Pushpala et al. |
| 2022/0175282 A1 | 6/2022 | Hoss et al. |
| 2022/0214300 A1 | 7/2022 | Wang et al. |
| 2022/0225901 A1 | 7/2022 | Chapman et al. |
| 2022/0233107 A1 | 7/2022 | Pushpala et al. |
| 2022/0249189 A1 | 8/2022 | Choi et al. |
| 2022/0298291 A1 | 9/2022 | Shin et al. |
| 2022/0322975 A1 | 10/2022 | Baker et al. |
| 2022/0322977 A1 | 10/2022 | Simpson et al. |
| 2022/0370011 A1 | 11/2022 | Windmiller et al. |
| 2023/0074798 A1 | 3/2023 | Tangney et al. |
| 2023/0094419 A1 | 3/2023 | Mansfield, III et al. |
| 2023/0099617 A1 | 3/2023 | Mansfield, III et al. |
| 2023/0137258 A1 | 5/2023 | Windmiller |
| 2023/0190147 A1 | 6/2023 | Campbell et al. |
| 2023/0256220 A1 | 8/2023 | Mansfield et al. |

FOREIGN PATENT DOCUMENTS

| | | |
|---|---|---|
| EP | 1006868 B1 | 6/2004 |
| EP | 1 372 602 B1 | 4/2007 |
| EP | 1792565 B1 | 10/2008 |
| EP | 1 187 653 B1 | 3/2010 |
| EP | 2 898 821 B1 | 12/2017 |
| EP | 3 381 370 A1 | 10/2018 |
| JP | H0222552 A | 1/1990 |
| JP | H-02-031741 A | 2/1990 |
| JP | H-07-275227 A | 10/1995 |
| JP | 2003-038464 A | 2/2003 |
| JP | 2003-038465 A | 2/2003 |
| JP | 2005-087613 A | 4/2005 |
| JP | 2006-510467 A | 4/2005 |
| JP | 2005-525141 A | 8/2005 |
| JP | 2005-322591 A | 11/2005 |
| JP | 2008-512162 A | 4/2008 |
| JP | 2008-540013 A | 11/2008 |
| JP | 2017108763 A | 6/2017 |
| JP | 2019205852 A | 12/2019 |
| JP | 2020170011 A | 10/2020 |
| JP | 2022501100 A | 1/2022 |
| KR | 10-2016-0108111 A | 9/2016 |
| WO | WO-00/74763 A2 | 12/2000 |
| WO | WO-00/74763 A3 | 12/2000 |
| WO | WO-2006/060106 A1 | 6/2006 |
| WO | WO-2006/093422 A1 | 9/2006 |
| WO | WO-2006/116242 A2 | 11/2006 |
| WO | WO-2006/116242 A3 | 11/2006 |
| WO | WO-2007/040938 A1 | 4/2007 |
| WO | WO-2009/034313 A2 | 3/2009 |
| WO | WO-2009/034313 A3 | 3/2009 |
| WO | WO-2009/064164 A2 | 5/2009 |
| WO | WO-2009/064164 A3 | 5/2009 |
| WO | WO-2009/124095 A1 | 10/2009 |
| WO | WO-2010/014959 A2 | 2/2010 |
| WO | WO-2010/014959 A3 | 2/2010 |
| WO | WO-2010/022252 A2 | 2/2010 |
| WO | WO-2010/022252 A3 | 2/2010 |
| WO | WO-2010/045247 A1 | 4/2010 |
| WO | WO-2010/059276 A1 | 5/2010 |
| WO | WO-2010/120364 A2 | 10/2010 |
| WO | WO-2010/120364 A3 | 10/2010 |
| WO | WO-2011/056095 A1 | 5/2011 |
| WO | WO-2012/020332 A2 | 2/2012 |
| WO | WO-2012/020332 A3 | 2/2012 |
| WO | WO-2012/142625 A2 | 10/2012 |
| WO | WO-2012/142625 A3 | 10/2012 |
| WO | WO-2013/058879 A2 | 4/2013 |
| WO | WO-2013/058879 A3 | 4/2013 |
| WO | WO-2014120114 A1 | 8/2014 |
| WO | WO-2015/073459 A1 | 5/2015 |
| WO | WO-2016189301 A1 | 12/2016 |
| WO | WO-2017/129980 A1 | 8/2017 |
| WO | WO-2017/189707 A1 | 11/2017 |
| WO | WO-2018/017196 A1 | 1/2018 |
| WO | WO-2018/071265 A1 | 4/2018 |
| WO | WO-2018/164886 A1 | 9/2018 |
| WO | WO-2018/170363 A1 | 9/2018 |

(56) References Cited

FOREIGN PATENT DOCUMENTS

| WO | WO-2019/156934 A1 | 8/2019 |
|---|---|---|
| WO | WO-2019/222615 A1 | 11/2019 |
| WO | WO-2019/239258 A1 | 12/2019 |
| WO | WO-2020/023804 A1 | 1/2020 |
| WO | WO-2020117918 A1 | 6/2020 |
| WO | WO-2021/015389 A1 | 1/2021 |
| WO | WO-2021/025260 A1 | 2/2021 |
| WO | WO-2021086690 A1 | 5/2021 |
| WO | WO-2021118124 A1 | 6/2021 |
| WO | WO-2021118431 A1 | 6/2021 |
| WO | WO-2022026764 A1 | 2/2022 |
| WO | WO-2022066985 A1 | 3/2022 |
| WO | WO-2022066992 A1 | 3/2022 |
| WO | WO-2022090741 A1 | 5/2022 |
| WO | WO-2022136785 A1 | 6/2022 |
| WO | WO-2023055755 A1 | 4/2023 |
| WO | WO-2023064877 A1 | 4/2023 |
| WO | WO-2023133468 A1 | 7/2023 |

OTHER PUBLICATIONS

American Diabetes Association® Press Release (2020). "American Diabetes Association® Applauds policymakers' Focus on Addressing High Costs of Insulin for Seven Million Americans," 4 pages.
Bantle, J.P. et al. (1997). "Glucose measurement in patients with diabetes mellitus with dermal interstitial fluid," J. Lab. Clin. Med. 130:436-441.
Beckles, G.L. et al. (2016). "Disparities in the prevalence of diagnosed diabetes—United States, 1999-2002 and 2011-2014," MMWR 65:1265-1269.
Cao, J. et al. (2017). "Validation of capillary blood analysis and capillary testing mode on the epoc Point of Care system," Pract. Lab. Med. 9:24-27.
Castle, J.R. et al. (2012). "The accuracy benefit of multiple amperometric glucose sensors in people with type 1 diabetes," Diabetes Care 35:706-710.
Chang, H. et al. (2017). "A swellable microneedle patch to rapidly extract skin interstitial fluid for timely metabolic analysis," Adv. Mater. 29:1702243.
Dexcom (2020). Analyst Day Presentation, 27 total pages.
Dexcom (2020). Analyst Day Presentation, 19 total pages.
Diabetes Care (2021). "7. Diabetes Technology: Standards of Medical Care in Diabetes—2021," Diabetes Care 44(Supplement 1):S85-S99.
Donnelly, R.F. et al. (2007). "Microstructured Devices for Transdermal Drug Delivery and Minimally-Invasive Patient Monitoring," Recent Patents on Drug Delivery & Formulation 1:195-200.
Extended European Search Report dated May 8, 2015, for EP Application No. 12 842 020.5, filed on Aug. 31, 2012, 7 pages.
Extended European Search Report dated Oct. 27, 2022, for EP Application No. 21 850 331.6, filed on Jul. 29, 2021, 8 pages.
Fang, M. et al. (2021). "Trends in Diabetes Treatment and Control in U.S. Adults, 1999-2018," N. Engl. Med. 384:2219-2228.
Final Office Action dated Aug. 19, 2016, for U.S. Appl. No. 14/965,755, filed Dec. 10, 2015, 17 pages.
Final Office Action dated Nov. 28, 2016, for U.S. Appl. No. 14/342,536, filed Jul. 30, 2014, 34 pages.
Final Office Action dated May 18, 2018, for U.S. Appl. No. 15/687,145, filed Aug. 25, 2017, 23 pages.
Final Office Action dated Dec. 7, 2020, for U.S. Appl. No. 15/961,793, filed Apr. 24, 2018, 13 pages.
Final Office Action dated May 21, 2021, for U.S. Appl. No. 16/051,398, filed Jul. 31, 2018, 11 pages.
Final Office Action dated Jun. 9, 2021, for U.S. Appl. No. 16/169,939, filed Oct. 24, 2018, 24 pages.
Final Office Action dated Sep. 23, 2021, for U.S. Appl. No. 15/913,709, filed Mar. 6, 2018, 17 pages.
Final Office Action dated May 9, 2022, for U.S. Appl. No. 17/389,153, filed Jul. 29, 2021, 17 pages.
Final Office Action dated Aug. 15, 2022, for U.S. Appl. No. 16/051,398, filed Jul. 31, 2018, 15 pages.
Final Office Action dated Oct. 27, 2022, for U.S. Appl. No. 15/913,709, filed Mar. 6, 2018, 21 pages.
French, D.P. et al. (2008). "Original Article: Psychological Care Self-monitoring of blood glucose changed non-insulin-treated Type 2 diabetes patients' beliefs about diabetes and self-monitoring in a randomized trial," Diav. Med. 25:1218-1228.
Gittard, S.D. et al. (2009). "Fabrication of Polymer Microneedles Using a Two-Photon Polymerization and Micromolding Process," J. Diabetes Sci. Technol. 3:304-311.
Grady, M. et al. (2017). "Examining the Impact of a Novel Blood Glucose Monitor With Color Range Indicator on Decision-Making in Patients With Type 1 and Type 2 Diabetes and its Association With Patient Numeracy Level," JMIR Diabetes 2:e24.
Grady, M. et al. (2018). "Use of Blood Glucose Meters Featuring Color Range Indicators Improves Glycemic Control in Patients with Diabetes in Comparison to Blood Glucose Meters Without Color (ACCENTS Study)," J. Diab. Sci. Tech. 12:1211-1219.
Groenendaal, W. et al. (2008). "Modeling Glucose and Water Dynamics in Human Skin," Diab. Tech. Therap. 10:283-293.
International Search Report dated Dec. 30, 2021, for PCT Application No. PCT/US2021/043786, filed on Jul. 29, 2021, 7 pages.
International Search Report dated Sep. 10, 2020, for PCT Application No. PCT/US2020/037379, filed on Jun. 12, 2020, 2 pages.
International Search Report dated Feb. 4, 2021, for PCT Application No. PCT/US2020/056517, filed on Oct. 20, 2020, 2 pages.
International Search Report dated Sep. 30, 2021, for PCT Application No. PCT/US2021/040385, filed on Jul. 2, 2021, 2 pages.
International Search Report dated Aug. 29, 2022, for PCT Application No. PCT/US2022/028196, filed on May 6, 2022, 2 pages.
International Search Report dated Jun. 27, 2013, for PCT Application No. PCT/US2012/053544, filed on Aug. 31, 2012, 4 pages.
Jeon, G. et al. (2011). "Electrically Actuatable Smart Nanoporous Membrane for Pulsatile Drug Release," Nano Lett. 11:1284-1288.
Jina, A et al. (2014). "Design, development, and evaluation of a novel microneedle array-based continuous glucose monitor," J. Diabetes Sci. Technol. 8:483-487.
Juvenile Diabetes Research Foundation Continuous Glucose Monitoring Study Group (2008). "Continuous Glucose Monitoring and Intensive Treatment of Type 1 Diabetes," N. Engl. Med. 359:1464-1476.
Karter, A.J. et al. (2021). "Association of Real-time Continuous Glucose Monitoring with Glycemic Control and Acute Metabolic Events Among Patients with Insulin-Treated Diabetes," JAMA 325:2273-2284.
Lhernould, M.S. et al. (2015). "Review of Patents for Microneedle Application Devices Allowing Fluid Injections Through the Skin," Recent Patents on Drug Delivery & Formulation 9:146-157.
Malitesta et al. (1990). "Glucose fast-response amperometric sensor based on glucose oxidase immobilized in an electropolymerized poly(o-phenylenediamine) film," Anal. Chem. 62:2735-2740.
Martens, T. et al. (2021). "Effect of Continuous Glucose Monitoring on Glycemic Control in Patients with Type 2 Diabetes Treated with Basal Insulin a Randomized Clinical Trial," JAMA 325:2262-2272.
McClatchey, P.M. et al. (2019). "Fibrotic Encapsulation Is the Dominant Source of Continuous Glucose Monitor Delays," Diabetes 68:1892-1901.
Miller, P.R. et al. (2011). "Integrated carbon fiber electrodes within hollow polymer microneedles for transdermal electrochemical sensing," BioMicrofluidics 5(1):013415.
Mohan, A.M. (2017). "Continuous minimally-invasive alcohol monitoring using microneedle sensor arrays," Biosensors and Bioelectronics 91:574-579.
Neerken, S. et al. (2004). "Characterization of age-related effects in human skin: A comparative study that applies confocal laser scanning microscopy and optical coherence tomography," J. Biomed. Optics 9:274-281.
Non-Final Office Action dated Mar. 10, 2016, for U.S. Appl. No. 14/965,755, filed Dec. 10, 2015, 15 pages.
Non-Final Office Action dated Mar. 30, 2016, for U.S. Appl. No. 14/342,536, filed Jul. 30, 2014, 31 pages.
Non-Final Office Action dated Mar. 9, 2017, for U.S. Appl. No. 14/965,755, filed Dec. 10, 2015, 17 pages.

(56) References Cited

OTHER PUBLICATIONS

Non-Final Office Action dated Apr. 6, 2017, for U.S. Appl. No. 14/342,536, filed Jul. 30, 2014, 32 pages.
Non-Final Office Action dated Nov. 1, 2017, for U.S. Appl. No. 15/687,145, filed Aug. 25, 2017, 19 pages.
Non-Final Office Action dated Jan. 19, 2018, for U.S. Appl. No. 14/843,926, filed Sep. 2, 2015, 11 pages.
Non-Final Office Action dated Apr. 13, 2020, for U.S. Appl. No. 15/961,793, filed Apr. 24, 2018, 13 pages.
Non-Final Office Action dated Sep. 3, 2020, for U.S. Appl. No. 16/169,939, filed Oct. 24, 2018, 19 pages.
Non-Final Office Action dated Sep. 16, 2020, for U.S. Appl. No. 15/913,709, filed Mar. 6, 2018, 15 pages.
Non-Final Office Action dated Oct. 16, 2020, for U.S. Appl. No. 16/051,398, filed Jul. 31, 2018, 13 pages.
Non-Final Office Action dated Nov. 4, 2021, for U.S. Appl. No. 16/169,939, filed Oct. 24, 2018, 20 pages.
Non-Final Office Action dated Nov. 26, 2021, for U.S. Appl. No. 16/051,398, filed Jul. 31, 2018, 15 pages.
Non-Final Office Action dated Nov. 29, 2021, for U.S. Appl. No. 17/389,153, filed Jul. 29, 2021, 14 pages.
Non-Final Office Action dated Apr. 8, 2022, for U.S. Appl. No. 17/650,056, filed Feb. 4, 2022, 14 pages.
Non-Final Office Action dated May 13, 2022, for U.S. Appl. No. 15/913,709, filed Mar. 6, 2018, 20 pages.
Non-Final Office Action dated Dec. 21, 2022, for U.S. Appl. No. 16/051,398, filed Jul. 31, 2018, 12 pages.
Notice of Allowance dated Jul. 6, 2017, for U.S. Appl. No. 14/965,755, filed Dec. 10, 2015, 12 pages.
Notice of Allowance dated Jul. 12, 2017, for U.S. Appl. No. 14/342,536, filed Jul. 30, 2014, 14 pages.
Notice of Allowance dated Feb. 13, 2018, for U.S. Appl. No. 14/843,926, filed Sep. 2, 2015, 8 pages.
Notice of Allowance dated Aug. 24, 2018, for U.S. Appl. No. 15/687,145, filed Aug. 25, 2017, 7 pages.
Notice of Allowance dated May 25, 2021, for U.S. Appl. No. 15/961,793, filed Apr. 24, 2018, 11 pages.
Notice of Allowance dated Sep. 12, 2022, for U.S. Appl. No. 17/389,153, filed Jul. 29, 2021, 8 pages.
Polonsky, W.H. et al. (2011). "A survey of blood glucose monitoring in patients with type 2 diabetes: Are recommendations from health care professionals being followed?" Curr. Med. Res. & Opinion 27:31-37.
Rigla, M. et al. (2018). "Human Subcutaneous Tissue Response to Glucose Sensors: Macrophages Accumulation Impact on Sensor Accuracy," Diabetes Technology & Therapeutics 20:296-302.
Sachdeva, V. et al. (2011). "Microneedles and their applications," Recent Patents on Drug Delivery & Formulation 5:95-132.
Sheikh, Z. et al. (2015). "Macrophages, Foreign Body Giant Cells and Their Response to Implantable Biomaterials," Materials 8:5671-5701.
Shi, T. et al. (2016). "Modeling and Measurement of Correlation between Blood and Interstitial Glucose Changes," J. Diab. Res. vol. 2016, 9 pages.
Singh, T.R.R. et al. (2010). "Microporation techniques for enhanced delivery of therapeutic agents," Recent Patents on Drug Delivery & Formulation 4:1-17.
Texas Instruments (Sep. 2007). Data sheet for a LMP2234 quad micropower, 1.6V, precision, operational amplifier with CMOS input, Sep. 2007, revised Mar. 2013, 31 total pages.
Windmiller, J.R. (2012). "Molecular scale biocomputing: An enzyme logic approach," University of California, San Diego, A dissertation submitted in partial satisfaction of the requirements for the degree Doctor of Philosophy in Electrical Engineering (Photonics), 78 total pages.
Windmiller, J.R. et al. (2011). "Bicomponent microneedle array biosensor for minimally-invasive glutamate monitoring," Electroanalysis 23:2302-2309.
Windmiller, J.R. et al. (2011). "Microneedle array-based carbon paste amperometric sensors and biosensors," Analyst 136:1846-1851.
Written Opinion of the International Searching Authority dated Dec. 30, 2021, for PCT Application No. PCT/US2021/043786, filed on Jul. 29, 2021, 10 pages.
Written Opinion of the International Searching Authority dated Sep. 10, 2020, for PCT Application No. PCT/US2020/037379, filed on Jun. 12, 2020, 4 pages.
Written Opinion of the International Searching Authority dated Feb. 4, 2021, for PCT Application No. PCT/US2020/056517, filed on Oct. 20, 2020, 5 pages.
Written Opinion of the International Searching Authority dated Sep. 30, 2021, for PCT Application No. PCT/US2021/040385, filed on Jul. 2, 2021, 2 pages.
Written Opinion of the International Searching Authority dated Aug. 29, 2022, for PCT Appiication No. PCT/US2022/028196, filed on May 6, 2022, 5 pages.
Written Opinion of the International Searching Authority dated Jun. 27, 2013, for PCT Application No. PCT/US2012/053544, filed on Aug. 31, 2012, 15 pages.
Yoon, Y. et al. (2013). "Fabrication of a Microneedle/CNT Hierarchical Micro/Nano Surface Electrochemical Sensor and Its In-Vitro Glucose Sensing Characterization," Sensors 13:16672-16681.
Al Hayek et al., "Patient Satisfaction and Clinical Efficacy of Novel Blood Glucose Meters Featuring Color Range Indicators in Patients With Type 2 Diabetes: A Prospective Study" Cureus Oct. 27, 2020; 12(10):e11195. doi: 10.7759/cureus.11195.
Allen et al., "Continuous glucose monitoring counseling improves physical activity behaviors of individuals with type 2 diabetes: A randomized clinical trial" Diabetes Res Clin Pract. Jun. 2008; 80(3): 371-379. doi:10.1016/j.diabres.2008.01.006.
Barrett et al., "Risk for Newly Diagnosed Diabetes >30 Days After SARS-CoV-2 Infection Among Persons Aged <18 Years—United States, Mar. 1, 2020-Jun. 28, 2021" MMWR Morb Mortal Wkly Rep. Jan. 14, 2022; 71(2):59-65. doi: 10.15585/mmwr.mm7102e2.
Centers for Disease Control, "National Diabetes Statistics Report 2020 Estimates of Diabetes and Its Burden in the United States" (2020) 32 pages.
Dunkin et al., "Scarring occurs at a critical depth of skin injury: precise measurement in a graduated dermal scratch in human volunteers" Plast Reconstr Surg. May 2007; 119(6):1722-1732. doi: 10.1097/01.prs.0000258829.07399.f0.
Ehrhardt et al, "The Effect of Real-Time Continuous Glucose Monitoring on Glycemic Control in Patients with Type 2 Diabetes Mellitus" Journal of Diabetes Science and Technology May 2011; 5(3):668-675.
Ehrhardt et al, "Behavior Modification in Prediabetes and Diabetes: Potential Use of Real-Time Continuous Glucose Monitoring" Journal of Diabetes Science and Technology Mar. 2019; 13(2):271-275.
Ehrhardt et al., "Continuous Glucose Monitoring As a Behavior Modification Tool" Clin Diabetes. Apr. 2020; 38(2):126-131. doi: 10.2337/cd19-0037.
Extended European Search Report dated Mar. 30, 2023, for European Application No. EP20881425.1, 8 pages.
Fonda et al., "The Cost-Effectiveness of Real-Time Continuous Glucose Monitoring (RT-CGM) in Type 2 Diabetes" Journal of Diabetes Science and Technology (2016) 10(4):898-904.
Han et al., "The End of the Road for the YSI 2300 Analyzer: Where Do We Go Now?" Journal of Diabetes Science and Technology (2020) 14(3):595-600.
Han et al., "The YSI 2300 Analyzer Replacement Meeting Report" Journal of Diabetes Science and Technology (2020) 14(3):679-686.
Non-Final Office Action dated Jan. 27, 2023, for U.S. Appl. No. 17/971,415, filed Oct. 21, 2022, 15 pages.
Non-Final Office Action dated Feb. 16, 2023 for U.S. Appl. No. 17/738,990, 9 pages.
Non-Final Office Action dated Mar. 9, 2023 for U.S. Appl. No. 17/389,156, filed Jul. 29, 2021, 24 pages.
Non-Final Office Action dated May 2, 2023 for U.S. Appl. No. 15/913,709, filed Mar. 6, 2018, 18 pages.
Sharifi et al., "Redundancy in Glucose Sensing: Enhanced Accuracy and Reliability of an Electrochemical Redundant Sensor for Con-

(56) References Cited

OTHER PUBLICATIONS tinuous Glucose Monitoring" Journal of Diabetes Science and Technology (2016) 10(3):669-678.
Swedish Search Report dated Feb. 3, 2023 for SE Application No. 2350067-1, 7 pages.
Turner et al., "Intensive blood-glucose control with sulphonylureas or insulin compared with conventional treatment and risk of complications in patients with type 2 diabetes (UKPDS 33)" The Lancet Sep. 1998; 352(9131):837-853.
Vigersky et al., "Short- and Long-Term Effects of Real-Time Continuous Glucose Monitoring in Patients with Type 2 Diabetes" Diabetes Care Jan. 2012; 35:32-38.
Wolicki et al., "Epidemiology and Prevention of Vaccine-Preventable Diseases: Chapter 6: Vaccine Administration" Centers for Disease Control and Prevention (2021) 17 pages.
World Health Organization, "Diabetes", Sep. 16, 2022, 5 pages.
Young et al., "Glucose Self-monitoring in Non-Insulin-Treated Patients With Type 2 Diabetes in Primary Care Settings: A Randomized Trial" JAMA Intern Med. Jul. 2017; 177(7):920-929.
Brown, "Design of Electronics for Wearable Electrochemical Sensors" University of California, San Diego, Master's Thesis (2019) 48 pages.
Final Office Action dated Aug. 29, 2023, for U.S. Appl. No. 18/086,543, filed Dec. 21, 2022, 17 pages.
Non-Final Office Action dated May 24, 2023, for U.S. Appl. No. 18/086,543, filed Dec. 21, 2022, 19 pages.
Non-Final Office Action dated Jun. 2, 2023, for U.S. Appl. No. 17/367,274, filed Jul. 2, 2021, 27 pages.
Non-Final Office Action dated Jun. 20, 2023, for U.S. Appl. No. 17/073,331, filed Oct. 17, 2020, 10 pages.
Notice of Allowance dated Jun. 12, 2023, for U.S. Appl. No. 17/971,415, filed Oct. 21, 2022, 14 pages.
Supplementary European Search Report dated Oct. 9, 2023, for EP Application No. 22808101.4, 4 pages.

\* cited by examiner

FAULT DETECTION FOR MICRONEEDLE ARRAY BASED CONTINUOUS ANALYTE MONITORING DEVICE

CROSS-REFERENCE TO RELATED APPLICATIONS

This application claims priority to U.S. Provisional Patent No. 63/186,086, filed May 8, 2021, the contents of which are hereby incorporated in their entirety by this reference.

TECHNICAL FIELD

This invention relates generally to the field of analyte monitoring, such as continuous glucose monitoring.

BACKGROUND

Diabetes is a chronic disease in which the body does not produce or properly utilize insulin, a hormone that regulates blood glucose. Insulin may be administered to a diabetic patient to help regulate blood glucose levels, though blood glucose levels must nevertheless be carefully monitored to help ensure that timing and dosage are appropriate. Without proper management of their condition, diabetic patients may suffer from a variety of complications resulting from hyperglycemia (high blood sugar levels) or hypoglycemia (low blood sugar levels).

Blood glucose monitors help diabetic patients manage their condition by measuring blood glucose levels from a sample of blood. For example, a diabetic patient may obtain a blood sample through a fingerstick sampling mechanism, transfer the blood sample to a test strip with suitable reagent(s) that react with the blood sample, and use a blood glucose monitor to analyze the test strip to measure glucose level in that blood sample. However, a patient using this process can typically only measure his or her glucose levels at discrete instances in time, which may fail to capture a hyperglycemia or hypoglycemia condition in a timely manner. Yet a more recent variety of glucose monitor is a continuous glucose monitor (CGM) device, which includes implantable transdermal electrochemical sensors that are used to continuously detect and quantify blood glucose levels by proxy measurement of glucose levels in the subcutaneous interstitial fluid. However, conventional CGM devices also have weaknesses including tissue trauma from insertion and signal latency (e.g., due to the time required for the glucose analyte to diffuse from capillary sources to the sensor). These weaknesses also lead to a number of drawbacks, such as pain experienced by the patient when electrochemical sensors are inserted, and limited accuracy in glucose measurements, particularly when blood glucose levels are changing rapidly. Accordingly, there is a need for a new and improved analyte monitoring system.

SUMMARY

In some variations, a microneedle array-based analyte monitoring device includes a working electrode, a reference electrode, a counter electrode, an analog front end, and a controller. The working electrodes includes an electrochemical sensing coating configured to generate a sensing current indicative of a redox reaction of an analyte at a surface of the working electrode, and the working electrode is positioned on a surface of a distal portion of a first microneedle in a microneedle array. The reference electrode is positioned on a surface of a distal portion of a second microneedle in the microneedle array. The counter electrode is positioned on a surface of a distal portion of a third microneedle in the microneedle array. The analog front end is configured to maintain a fixed potential relationship between the working electrode and the reference electrode and to allow potential of the counter electrode to swing to sustain the redox reaction at the working electrode. The controller is in communication with the analog front end and is configured to: monitor a counter electrode voltage at the counter electrode; identify a characteristic of the counter electrode voltage that meets or exceeds a threshold value; determine, in response to identifying the characteristic of the counter electrode voltage that exceeds the threshold value, a correlation between the counter electrode voltage and the sensing current; and apply, based on the characteristic of the counter electrode voltage and the correlation, a mode of operation to the microneedle array-based analyte monitoring device.

In some variations, a method includes monitoring a counter electrode voltage at a counter electrode of a microneedle array-based analyte monitoring device, the counter electrode positioned on a surface of a distal portion of a first microneedle in the microneedle array; identifying a characteristic of the counter electrode voltage that meets or exceeds a threshold value; determining, in response to identifying the characteristic of the counter electrode voltage that exceeds the threshold value, a correlation between the counter electrode voltage and a sensing current, the sensing current generated at a surface of a working electrode of the microneedle array-based analyte monitoring device; and applying, based on the characteristic of the counter electrode voltage and the correlation, a mode of operation to the microneedle array-based analyte monitoring device. The working electrode may include an electrochemical sensing coating configured to generate the sensing current indicative of a redox reaction of an analyte at the surface of the working electrode, the working electrode positioned on a surface of a distal portion of a second microneedle in a microneedle array. The microneedle array-based analyte monitoring device may further include a reference electrode positioned on a surface of a distal portion of a third microneedle in the microneedle array, and an analog front end configured to maintain a fixed potential relationship between the working electrode and the reference electrode and to allow potential of the counter electrode to swing to sustain the redox reaction at the working electrode.

In some variations, the characteristic of the counter electrode voltage include one or more of a rate of change of the counter electrode voltage or a lower compliance limit of the counter electrode voltage.

In some variations, changes in the counter electrode voltage and changes in the sensing current are indicative of the correlation between the counter electrode voltage and the sensing current.

In some variations, the mode of operation includes disregarding the sensing current if the changes in the counter electrode voltage correspond with the changes in the sensing current and if the rate of change of the counter electrode voltage exceeds a threshold rate of change.

In some variations, the controller is further configured to interrupt the mode of operation of disregarding the sensing current, in response to a subsequent determination that the rate of change of the counter electrode voltage does not exceed the threshold rate of change.

In some variations, the mode of operation includes discontinuing application of a potential between the working electrode and the reference electrode if the lower compliance limit of the counter electrode voltage meets a threshold compliance limit.

In some variations, the mode of operation includes discontinuing application of a potential between the working electrode and the reference electrode if the changes in the counter electrode voltage deviate from the changes in the sensing current and if the rate of change of the counter electrode voltage exceeds a threshold rate of change.

In some variations, the microneedle array-based analyte monitoring device further includes one or more additional working electrodes, each of the one or more additional working electrodes generating a respective sensing current. The controller is further configured to determine, in response to identifying the characteristic of the counter electrode voltage that exceeds the threshold value, a correlation between the counter electrode voltage and the respective sensing current.

In some variations, the mode of operation is further based on the correlation between the counter electrode voltage and the respective sensing current.

In some variations, the sensing current at the working electrode and the respective sensing current at the one or more additional working electrodes are combined to determine a combined correlation.

DETAILED DESCRIPTION

Non-limiting examples of various aspects and variations of the invention are described herein and illustrated in the accompanying drawings.

Figure 1:
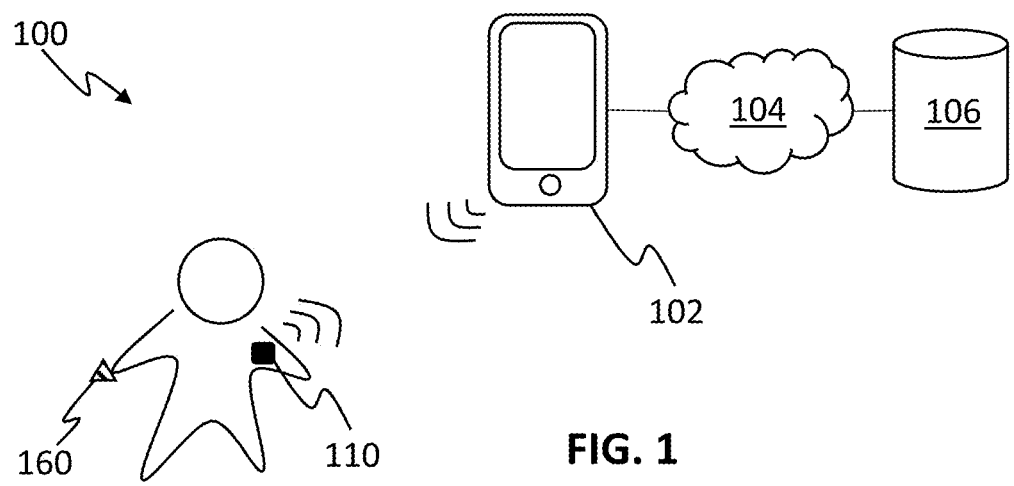
FIG. 1 depicts an illustrative schematic of an analyte monitoring system with a microneedle array.

As generally described herein, an analyte monitoring system may include an analyte monitoring device that is worn by a user and includes one or more sensors for monitoring at least one analyte of a user. The sensors may, for example, include one or more electrodes configured to perform electrochemical detection of at least one analyte. The analyte monitoring device may communicate sensor data to an external computing device for storage, display, and/or analysis of sensor data. For example, as shown in FIG. 1, an analyte monitoring system 100 may include an analyte monitoring device 110 that is worn by a user, and the analyte monitoring device 110 may be a continuous analyte monitoring device (e.g., continuous glucose monitoring device). The analyte monitoring device 110 may include, for example, a microneedle array comprising at least one electrochemical sensor for detecting and/or measuring one or more analytes in body fluid of a user. In some variations, the analyte monitoring device may be applied to the user using suitable applicator 160, or may be applied manually. The analyte monitoring device 110 may include one or more processors for performing analysis on sensor data, and/or a communication module (e.g., wireless communication module) configured to communicate sensor data to a mobile computing device 102 (e.g., smartphone) or other suitable computing device. In some variations, the mobile computing device 102 may include one or more processors executing a mobile application to handle sensor data (e.g., displaying data, analyzing data for trends, etc.) and/or provide suitable alerts or other notifications related to the sensor data and/or analysis thereof. It should be understood that while in some variations the mobile computing device 102 may perform sensor data analysis locally, other computing device(s) may alternatively or additionally remotely analyze sensor data and/or communicate information related to such analysis with the mobile computing device 102 (or other suitable user interface) for display to the user. Furthermore, in some variations the mobile computing device 102 may be configured to communicate sensor data and/or analysis of the sensor data over a network 104 to one or more storage devices 106 (e.g., server) for archiving data and/or other suitable information related to the user of the analyte monitoring device.

The analyte monitoring devices described herein have characteristics that improve a number of properties that are advantageous for a continuous analyte monitoring device such as a continuous glucose monitoring (CGM) device. For example, the analyte monitoring device described herein have improved sensitivity (amount of sensor signal produced per given concentration of target analyte), improved selectivity (rejection of endogenous and exogenous circulating compounds that can interfere with the detection of the target analyte), and improved stability to help minimize change in sensor response over time through storage and operation of the analyte monitoring device. Additionally, compared to conventional continuous analyte monitoring devices, the analyte monitoring devices described herein have a shorter warm-up time that enables the sensor(s) to quickly provide a stable sensor signal following implantation, as well as a short response time that enables the sensors(s) to quickly provide a stable sensor signal following a change in analyte concentration in the user. Furthermore, as described in further detail below, the analyte monitoring devices described herein may be applied to and function in a variety of wear sites, and provide for pain-free sensor insertion for the user. Other properties such as biocompatibility, sterilizability, and mechanical integrity are also optimized in the analyte monitoring devices described herein.

Although the analyte monitoring systems described herein may be described with reference to monitoring of glucose (e.g., in users with Type 2 diabetes, Type 1 diabetes), it should be understood that such systems may additionally or alternatively be configured to sense and monitor other suitable analytes. As described in further detail below, suitable target analytes for detection may, for example, include glucose, ketones, lactate, and cortisol. One target analyte may be monitored, or multiple target analytes may be simultaneously monitored (e.g., in the same analyte monitoring device). For example, monitoring of other target analytes may enable the monitoring of other indications such as stress (e.g., through detection of rising cortisol and glucose) and ketoacidosis (e.g., through detection of rising ketones).

Figure 2A:
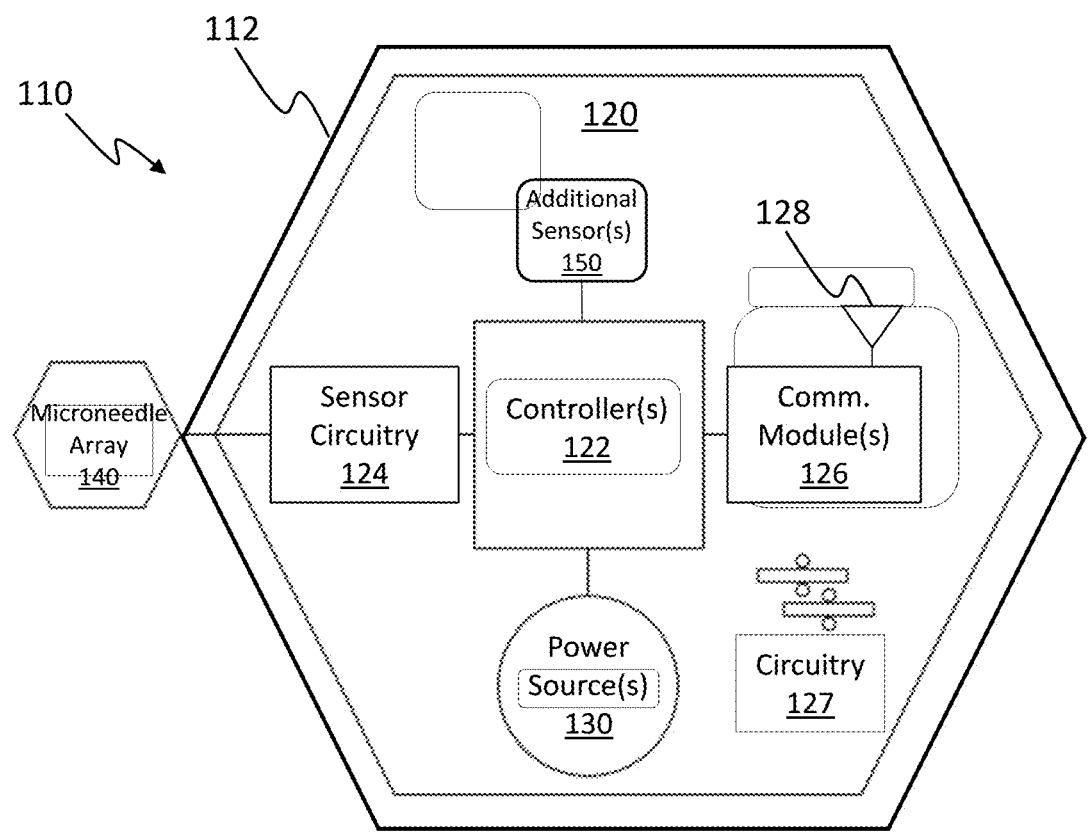
FIG. 2A depicts an illustrative schematic of an analyte monitoring device.

As shown in FIG. 2A, in some variations, an analyte monitoring device 110 may generally include a housing 112 and a microneedle array 140 extending outwardly from the housing. The housing 112, may, for example, be a wearable housing configured to be worn on the skin of a user such that the microneedle array 140 extends at least partially into the skin of the user. For example, the housing 112 may include an adhesive such that the analyte monitoring device 110 is a skin-adhered patch that is simple and straightforward for application to a user. The microneedle array 140 may be configured to puncture the skin of the user and include one or more electrochemical sensors (e.g., electrodes) configured for measuring one or more target analytes that are accessible after the microneedle array 140 punctures the skin of the user. In some variations, the analyte monitoring device 110 may be integrated or self-contained as a single unit, and the unit may be disposable (e.g., used for a period of time and replaced with another instance of the analyte monitoring device 110).

An electronics system 120 may be at least partially arranged in the housing 112 and include various electronic components, such as sensor circuitry 124 configured to perform signal processing (e.g., biasing and readout of electrochemical sensors, converting the analog signals from the electrochemical sensors to digital signals, etc.). The electronics system 120 may also include at least one microcontroller 122 for controlling the analyte monitoring device 110, at least one communication module 126, at least one power source 130, and/or other various suitable passive circuitry 127. The microcontroller 122 may, for example, be configured to interpret digital signals output from the sensor circuitry 124 (e.g., by executing a programmed routine in firmware), perform various suitable algorithms or mathematical transformations (e.g., calibration, etc.), and/or route processed data to and/or from the communication module 126. In some variations, the communication module 126 may include a suitable wireless transceiver (e.g., Bluetooth transceiver or the like) for communicating data with an external computing device 102 via one or more antennas 128. For example, the communication module 126 may be configured to provide uni-directional and/or bi-directional communication of data with an external computing device 102 that is paired with the analyte monitoring device 110. The power source 130 may provide power for the analyte monitoring device 110, such as for the electronics system. The power source 130 may include battery or other suitable source, and may, in some variations, be rechargeable and/or replaceable. Passive circuitry 127 may include various non-powered electrical circuitry (e.g., resistors, capacitors, inductors, etc.) providing interconnections between other electronic components, etc. The passive circuitry 127 may be configured to perform noise reduction, biasing and/or other purposes, for example. In some variations, the electronic components in the electronics system 120 may be arranged on one or more printed circuit boards (PCB), which may be rigid, semi-rigid, or flexible, for example. Additional details of the electronics system 120 are described further below.

In some variations, the analyte monitoring device 110 may further include one or more additional sensors 150 to provide additional information that may be relevant for user monitoring. For example, the analyte monitoring device 110 may further include at least one temperature sensor (e.g., thermistor) configured to measure skin temperature, thereby enabling temperature compensation for the sensor measurements obtained by the microneedle array electrochemical sensors.

Figure 2B:
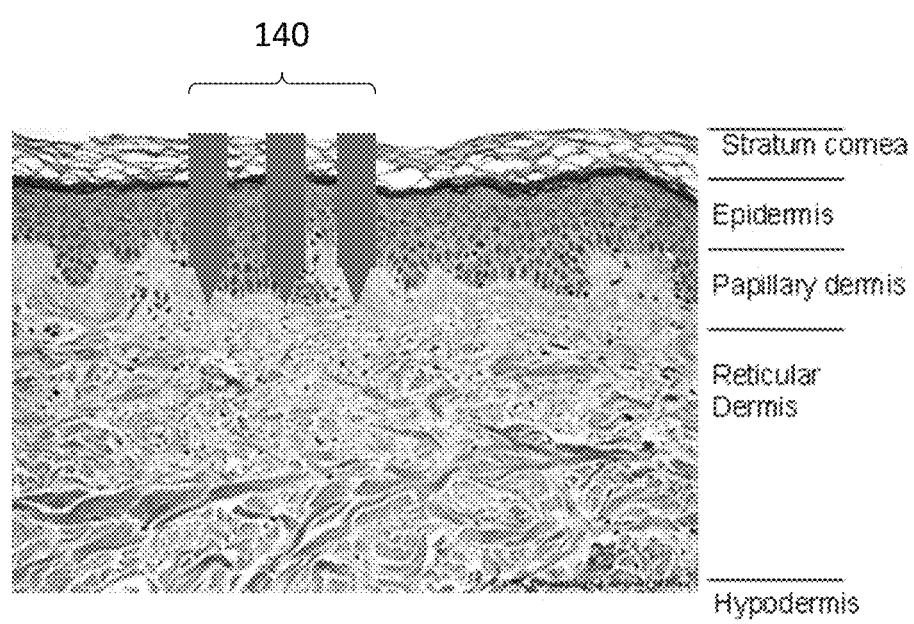
FIG. 2B depicts an illustrative schematic of microneedle insertion depth in an analyte monitoring device.

In some variations, the microneedle array 140 in the analyte monitoring device 110 may be configured to puncture skin of a user. As shown in FIG. 2B, when the device 110 is worn by the user, the microneedle array 140 may extend into the skin of the user such that electrodes on distal regions of the microneedles rest in the dermis. Specifically, in some variations, the microneedles may be designed to penetrate the skin and access the upper dermal region (e.g., papillary dermis and upper reticular dermis layers) of the skin, in order to enable the electrodes to access interstitial fluid that surrounds the cells in these layers. For example, in some variations, the microneedles may have a height generally ranging between at least 350 μm and about 515 μm. In some variations, one or more microneedles may extend from the housing such that a distal end of the electrode on the microneedle is located less than about 5 mm from a skin-interfacing surface of the housing, less than about 4 mm from the housing, less than about 3 mm from the housing, less than about 2 mm from the housing, or less than about 1 mm from the housing.

In contrast to traditional continuous analyte monitoring devices (e.g., CGM devices), which include sensors typically implanted between about 8 mm and about 10 mm beneath the skin surface in the subcutis or adipose layer of the skin, the analyte monitoring device 110 has a shallower microneedle insertion depth of about 0.25 mm (such that electrodes are implanted in the upper dermal region of the skin) that provides numerous benefits. These benefits include access to dermal interstitial fluid including one or more target analytes for detection, which is advantageous at least because at least some types of analyte measurements of dermal interstitial fluid have been found to closely correlate to those of blood. For example, it has been discovered that glucose measurements performed using electrochemical sensors accessing dermal interstitial fluid are advantageously highly linearly correlated with blood glucose measurements. Accordingly, glucose measurements based on dermal interstitial fluid are highly representative of blood glucose measurements.

Additionally, because of the shallower microneedle insertion depth of the analyte monitoring device 110, a reduced time delay in analyte detection is obtained compared to traditional continuous analyte monitoring devices. Such a shallower insertion depth positions the sensor surfaces in close proximity (e.g., within a few hundred micrometers or less) to the dense and well-perfused capillary bed of the reticular dermis, resulting in a negligible diffusional lag from the capillaries to the sensor surface. Diffusion time is related to diffusion distance according to $t=x^2/(2D)$ where t is the diffusion time, x is the diffusion distance, and D is the mass diffusivity of the analyte of interest. Therefore, positioning an analyte sensing element twice as far away from the source of an analyte in a capillary will result in a quadrupling of the diffusional delay time. Accordingly, conventional analyte sensors, which reside in the very poorly vascularized adipose tissue beneath the dermis, result in a significantly greater diffusion distance from the vasculature in the dermis and thus a substantial diffusional latency (e.g., typically 5-20 minutes). In contrast, the shallower microneedle insertion depth of the analyte monitoring device 110 benefits from low diffusional latency from capillaries to the sensor, thereby reducing time delay in analyte detection and providing more accurate results in real-time or near real-time. For example, in some embodiments, diffusional latency may be less than 10 minutes, less than 5 minutes, or less than 3 minutes.

Furthermore, when the microneedle array rests in the upper dermal region, the lower dermis beneath the microneedle array includes very high levels of vascularization and perfusion to support the dermal metabolism, which enables thermoregulation (via vasoconstriction and/or vasodilation) and provides a barrier function to help stabilize the sensing environment around the microneedles. Yet another advantage of the shallower insertion depth is that the upper dermal layers lack pain receptors, thus resulting in a reduced pain sensation when the microneedle array punctures the skin of the user, and providing for a more comfortable, minimally-invasive user experience.

Thus, the analyte monitoring devices and methods described herein enable improved continuous monitoring of one or more target analytes of a user. For example, as described above, the analyte monitoring device may be simple and straightforward to apply, which improves ease-of-use and user compliance. Additionally, analyte measurements of dermal interstitial fluid may provide for highly accurate analyte detection. Furthermore, compared to traditional continuous analyte monitoring devices, insertion of the microneedle array and its sensors may be less invasive and involve less pain for the user. Additional advantages of other aspects of the analyte monitoring devices and methods are further described below.

Figure 3A:
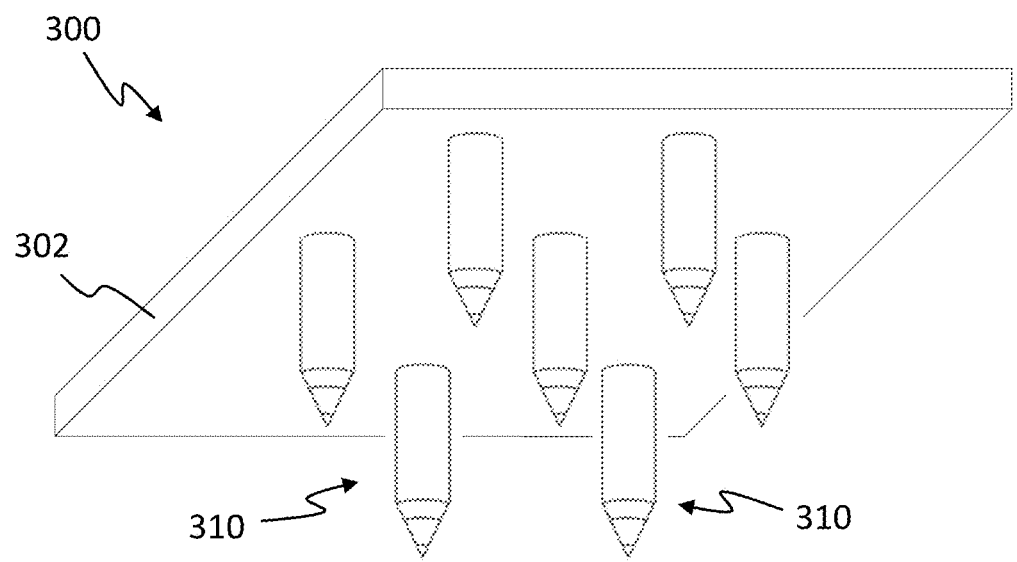
FIG. 3A depicts an illustrative schematic of a microneedle array.
Figure 3B:
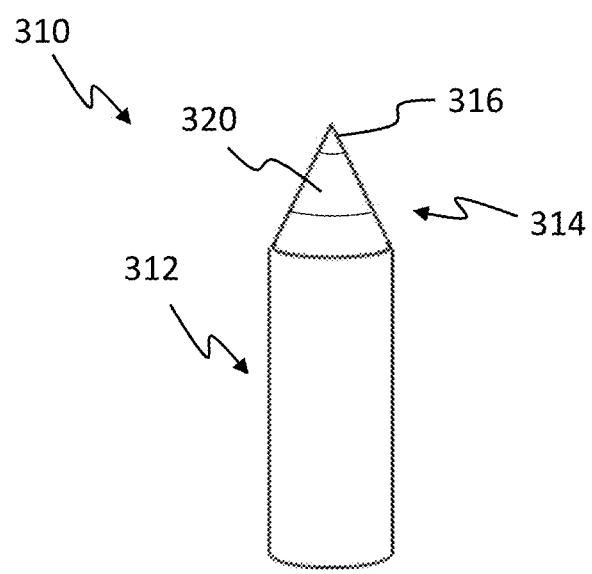
FIG. 3B depicts an illustrative schematic of a microneedle in the microneedle array depicted in FIG. 3A.

As shown in the schematic of FIG. 3A, in some variations, a microneedle array 300 for use in sensing one or more analytes may include one or more microneedles 310 projecting from a substrate surface 302. The substrate surface 302 may, for example, be generally planar and one or more microneedles 310 may project orthogonally from the planar surface. Generally, as shown in FIG. 3B, a microneedle 310 may include a body portion 312 (e.g., shaft) and a tapered distal portion 314 configured to puncture skin of a user. In some variations, the tapered distal portion 314 may terminate in an insulated distal apex 316. The microneedle 310 may further include an electrode 320 on a surface of the tapered distal portion. In some variations, electrode-based measurements may be performed at the interface of the electrode and interstitial fluid located within the body (e.g., on an outer surface of the overall microneedle). In some variations, the microneedle 310 may have a solid core (e.g., solid body portion), though in some variations the microneedle 310 may include one or more lumens, which may be used for drug delivery or sampling of the dermal interstitial fluid, for example. Other microneedle variations, such as those described below, may similarly either include a solid core or one or more lumens.

The microneedle array 300 may be at least partially formed from a semiconductor (e.g., silicon) substrate and include various material layers applied and shaped using various suitable microelectromechanical systems (MEMS) manufacturing techniques (e.g., deposition and etching techniques), as further described below. The microneedle array may be reflow-soldered to a circuit board, similar to a typical integrated circuit. Furthermore, in some variations the microneedle array 300 may include a three electrode setup including a working (sensing) electrode having an electrochemical sensing coating (including a biorecognition element such as an enzyme) that enables detection of a target analyte, a reference electrode, and a counter electrode. In other words, the microneedle array 300 may include at least one microneedle 310 that includes a working electrode, at least one microneedle 310 including a reference electrode, and at least one microneedle 310 including a counter electrode. Additional details of these types of electrodes are described in further detail below.

Figure 4:
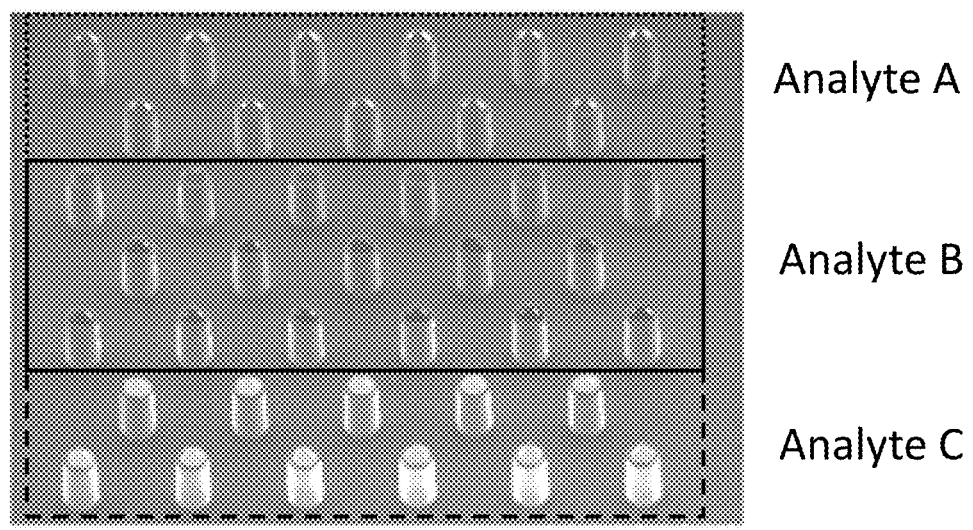
FIG. 4 depicts an illustrative schematic of a microneedle array used for sensing multiple analytes.

In some variations, the microneedle array 300 may include a plurality of microneedles that are insulated such that the electrode on each microneedle in the plurality of microneedles is individually addressable and electrically isolated from every other electrode on the microneedle array. The resulting individual addressability of the microneedle array 300 may enable greater control over each electrode's function, since each electrode may be separately probed. For example, the microneedle array 300 may be used to provide multiple independent measurements of a given target analyte, which improves the device's sensing reliability and accuracy. Furthermore, in some variations the electrodes of multiple microneedles may be electrically connected to produce augmented signal levels. As another example, the same microneedle array 500 may additionally or alternatively be interrogated to simultaneously measure multiple analytes to provide a more comprehensive assessment of physiological status. For example, as shown in the schematic of FIG. 4, a microneedle array may include a portion of microneedles to detect a first Analyte A, a second portion of microneedles to detect a second Analyte B, and a third portion of microneedles to detect a third Analyte C. It should be understood that the microneedle array may be configured to detect any suitable number of analytes (e.g., 1, 2, 3, 4, 5 or more, etc.). Suitable target analytes for detection may, for example, include glucose, ketones, lactate, and cortisol. Thus, individual electrical addressability of the microneedle array 300 provides greater control and flexibility over the sensing function of the analyte monitoring device.

In some variations of microneedles (e.g., microneedles with a working electrode), the electrode 320 may be located proximal to the insulated distal apex 316 of the microneedle. In other words, in some variations the electrode 320 does not cover the apex of the microneedle. Rather, the electrode 320 may be offset from the apex or tip of the microneedle. The electrode 320 being proximal to or offset from the insulated distal apex 316 of the microneedle advantageously provides more accurate sensor measurements. For example, this arrangement prevents concentration of the electric field at the microneedle apex 316 during manufacturing, thereby avoiding non-uniform electro-deposition of sensing chemistry on the surface of the electrode 320 that would result in faulty sensing.

As another example, placing the electrode 320 offset from the microneedle apex further improves sensing accuracy by reducing undesirable signal artefacts and/or erroneous sensor readings caused by stress upon microneedle insertion. The distal apex of the microneedle is the first region to penetrate into the skin, and thus experiences the most stress caused by the mechanical shear phenomena accompanying the tearing or cutting of the skin. If the electrode 320 were placed on the apex or tip of the microneedle, this mechanical stress may delaminate the electrochemical sensing coating on the electrode surface when the microneedle is inserted, and/or cause a small yet interfering amount of tissue to be transported onto the active sensing portion of the electrode. Thus, placing the electrode 320 sufficiently offset from the microneedle apex may improve sensing accuracy. For example, in some variations, a distal edge of the electrode 320 may be located at least about 10 μm (e.g., between about 20 μm and about 30 μm) from the distal apex or tip of the microneedle, as measured along a longitudinal axis of the microneedle.

The body portion 312 of the microneedle 310 may further include an electrically conductive pathway extending between the electrode 320 and a backside electrode or other electrical contact (e.g., arranged on a backside of the substrate of the microneedle array). The backside electrode may be soldered to a circuit board, enabling electrical communication with the electrode 320 via the conductive pathway. For example, during use, the in-vivo sensing current (inside the dermis) measured at a working electrode is interrogated by the backside electrical contact, and the electrical connection between the backside electrical contact and the working electrode is facilitated by the conductive pathway. In some variations, this conductive pathway may be facilitated by a metal via running through the interior of the microneedle body portion (e.g., shaft) between the microneedle's proximal and distal ends. Alternatively, in some variations the conductive pathway may be provided by the entire body portion being formed of a conductive material (e.g., doped silicon). In some of these variations, the complete substrate on which the microneedle array 300 is built upon may be electrically conductive, and each microneedle 310 in the microneedle array 300 may be electrically isolated from adjacent microneedles 310 as described below. For example, in some variations, each microneedle 310 in the microneedle array 300 may be electrically isolated from adjacent microneedles 310 with an insulative barrier including electrically insulative material (e.g., dielectric material such as silicon dioxide) that surrounds the conductive pathway extending between the electrode 320 and backside electrical contact. For example, body portion 312 may include an insulative material that forms a sheath around the conductive pathway, thereby preventing electrical communication between the conductive pathway and the substrate. Other example variations of structures enabling electrical isolation among microneedles are described in further detail below.

Such electrical isolation among microneedles in the microneedle array permits the sensors to be individually addressable. This individually addressability advantageously enables independent and parallelized measurement among the sensors, as well as dynamic reconfiguration of sensor assignment (e.g., to different analytes). In some variations, the electrodes in the microneedle array can be configured to provide redundant analyte measurements, which is an advantage over conventional analyte monitoring devices. For example, redundancy can improve performance by improving accuracy (e.g., averaging multiple analyte measurement values for the same analyte which reduces the effect of extreme high or low sensor signals on the determination of analyte levels) and/or improving reliability of the device by reducing the likelihood of total failure.

In some variations, as described in further detail below with respective different variations of the microneedle, the microneedle array may be formed at least in part with suitable semiconductor and/or MEMS fabrication techniques and/or mechanical cutting or dicing. Such processes may, for example, be advantageous for enabling large-scale, cost-efficient manufacturing of microneedle arrays.

Figure 5A:
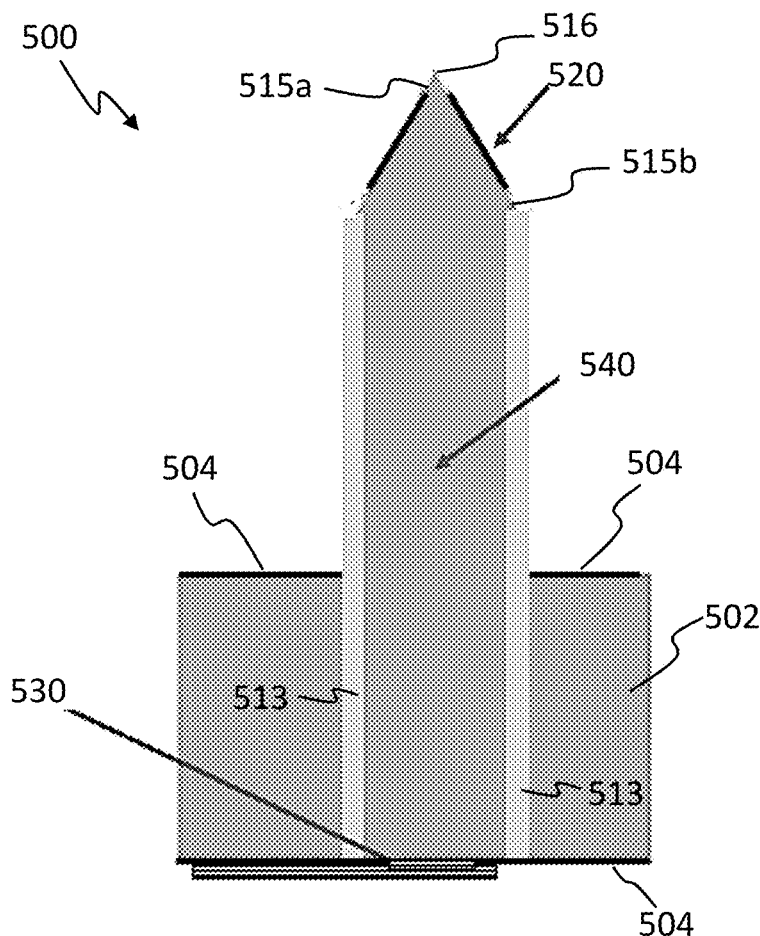
FIG. 5A depicts a cross-sectional side view of a columnar microneedle having a tapered distal end.
Figure 5B:
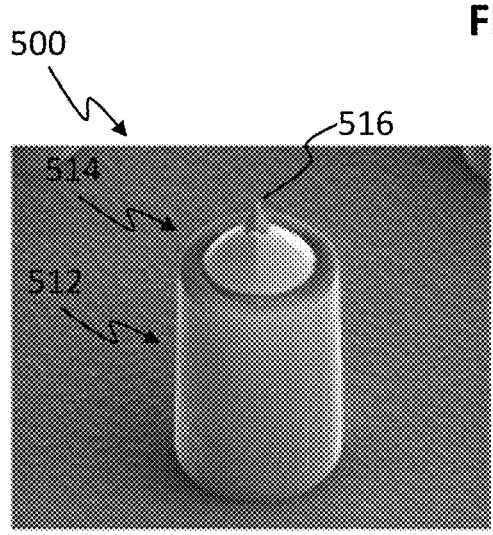
FIGS. 5B and 5C are images depicting perspective and detailed views, respectively, of an embodiment of the microneedle shown in FIG. 5A.
Figure 5C:
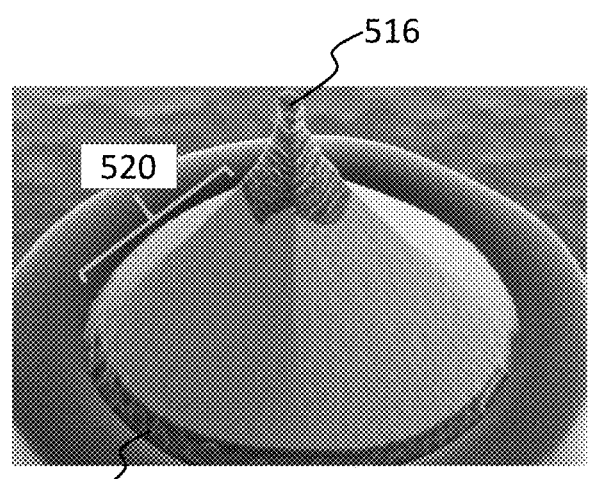

In some variations, a microneedle may have a generally columnar body portion and a tapered distal portion with an electrode. For example, FIGS. 5A-5C illustrate an example variation of a microneedle 500 extending from a substrate 502. FIG. 5A is a side cross-sectional view of a schematic of microneedle 500, while FIG. 5B is a perspective view of the microneedle 500 and FIG. 5C is a detailed perspective view of a distal portion of the microneedle 500. As shown in FIGS. 5B and 5C, the microneedle 500 may include a columnar body portion 512, a tapered distal portion 514 terminating in an insulated distal apex 516, and an annular electrode 520 that includes a conductive material (e.g., Pt, Ir, Au, Ti, Cr, Ni, etc.) and is arranged on the tapered distal portion 514. As shown in FIG. 5A, the annular electrode 520 may be proximal to (or offset or spaced apart from) the distal apex 516. For example, the electrode 520 may be electrically isolated from the distal apex 516 by a distal insulating surface 515a including an insulating material (e.g., $SiO_2$). In some variations, the electrode 520 may also be electrically isolated from the columnar body portion 512 by a second distal insulating surface 515b. The electrode 520 may be in electrical communication with a conductive core 540 (e.g., conductive pathway) passing along the body portion 512 to a backside electrical contact 530 (e.g., made of Ni/Au alloy) or other electrical pad in or on the substrate 502. For example, the body portion 512 may include a conductive core material (e.g., highly doped silicon). As shown in FIG. 5A, in some variations, an insulating moat 513 including an insulating material (e.g., $SiO_2$) may be arranged around (e.g., around the perimeter) of the body portion 512 and extend at least partially through the substrate 502. Accordingly, the insulating moat 513 may, for example, help prevent electrical contact between the conductive core 540 and the surrounding substrate 502. The insulating moat 513 may further extend over the surface of the body portion 512. Upper and/or lower surfaces of the substrate 502 may also include a layer of substrate insulation 504 (e.g., $SiO_2$). Accordingly, the insulation provided by the insulating moat 513 and/or substrate insulation 504 may contribute at least in part to the electrical isolation of the microneedle 500 that enables individual addressability of the microneedle 500 within a microneedle array. Furthermore, in some variations the insulating moat 513 extending over the surface of the body portion 512 may function to increase the mechanical strength of the microneedle 500 structure.

The microneedle 500 may be formed at least in part by suitable MEMS fabrication techniques such as plasma etching, also called dry etching. For example, in some variations, the insulating moat 513 around the body portion 512 of the microneedle may be made by first forming a trench in a silicon substrate by deep reactive ion etching (DRIE) from the backside of the substrate, then filling that trench with a sandwich structure of SiO$_2$/polycrystalline silicon (poly-Si)/SiO$_2$ by low pressure chemical vapor deposition (LPCVD) or other suitable process. In other words, the insulating moat 513 may passivate the surface of the body portion 512 of the microneedle, and continue as a buried feature in the substrate 502 near the proximal portion of the microneedle. By including largely compounds of silicon, the insulating moat 513 may provide good fill and adhesion to the adjoining silicon walls (e.g., of the conductive core 540, substrate 502, etc.). The sandwich structure of the insulating moat 513 may further help provide excellent matching of coefficient of thermal expansion (CTE) with the adjacent silicon, thereby advantageously reducing faults, cracks, and/or other thermally-induced weaknesses in the insulating moat 513.

The tapered distal portion may be fashioned out by an isotropic dry etch from the frontside of the substrate, and the body portion 512 of the microneedle 500 may be formed from DRIE. The frontside metal electrode 520 may be deposited and patterned on the distal portion by specialized lithography (e.g., electron-beam evaporation) that permits metal deposition in the desired annular region for the electrode 520 without coating the distal apex 516. Furthermore, the backside electrical contact 530 of Ni/Au may be deposited by suitable MEMS manufacturing techniques (e.g., sputtering).

The microneedle 500 may have any suitable dimensions. By way of illustration, the microneedle 500 may, in some variations, have a height of between about 300 µm and about 500 µm. In some variations, the tapered distal portion 514 may have a tip angle between about 60 degrees and about 80 degrees, and an apex diameter of between about 1 µm and about 15 µm. In some variations, the surface area of the annular electrode 520 may include between about 9,000 µm$^2$ and about 11,000 µm$^2$, or about 10,000 µm$^2$.

As described above, each microneedle in the microneedle array may include an electrode. In some variations, multiple distinct types of electrodes may be included among the microneedles in the microneedle array. For example, in some variations the microneedle array may function as an electrochemical cell operable in an electrolytic manner with three types of electrodes. In other words, the microneedle array may include at least one working electrode, at least one counter electrode, and at least one reference electrode. Thus, the microneedle array may include three distinct electrode types, though one or more of each electrode type may form a complete system (e.g., the system might include multiple distinct working electrodes). Furthermore, multiple distinct microneedles may be electrically joined to form an effective electrode type (e.g., a single working electrode may be formed from two or more connected microneedles with working electrode sites). Each of these electrode types may include a metallization layer and may include one or more coatings or layers over the metallization layer that help facilitate the function of that electrode.

Generally, the working electrode is the electrode at which oxidation and/or reduction reaction of interest occurs for detection of an analyte of interest. The counter electrode functions to source (provide) or sink (accumulate) the electrons, via an electrical current, that are required to sustain the electrochemical reaction at the working electrode. The reference electrode functions to provide a reference potential for the system; that is, the electrical potential at which the working electrode is biased is referenced to the reference electrode. A fixed, time-varying, or at least controlled potential relationship is established between the working and reference electrodes, and within practical limits no current is sourced from or sinked to the reference electrode. Additionally, to implement such a three-electrode system, the analyte monitoring device may include a suitable potentiostat or electrochemical analog front end to maintain a fixed potential relationship between the working electrode and reference electrode contingents within the electrochemical system (via an electronic feedback mechanism), while permitting the counter electrode to dynamically swing to potentials required to sustain the redox reaction of interest.

Working Electrode

As described above, the working electrode is the electrode at which the oxidation and/or reduction reaction of interest occurs. In some variations, sensing may be performed at the interface of the working electrode and interstitial fluid located within the body (e.g., on an outer surface of the overall microneedle). In some variations, a working electrode may include an electrode material and a biorecognition layer in which a biorecognition element (e.g., enzyme) is immobilized on the working electrode to facilitate selective analyte quantification. In some variations, the biorecognition layer may also function as an interference-blocking layer and may help prevent endogenous and/or exogenous species from directly oxidizing (or reducing) at the electrode.

A redox current detected at the working electrode may be correlated to a detected concentration of an analyte of interest. This is because assuming a steady-state, diffusion-limited system, the redox current detected at the working electrode follows the Cottrell relation below:

$$i(t) = \frac{nFA\sqrt{D}\,C}{\sqrt{\pi t}}$$

where n is the stoichiometric number of electrons mitigating a redox reaction, F is Faraday's constant, A is electrode surface area, D is the diffusion coefficient of the analyte of interest, C is the concentration of the analyte of interest, and t is the duration of time that the system is biased with an electrical potential. Thus, the detected current at the working electrode scales linearly with the analyte concentration.

Moreover, because the detected current is a direct function of electrode surface area A, the surface area of the electrode may be increased to enhance the sensitivity (e.g., amperes per molar of analyte) of the sensor. For example, multiple singular working electrodes may be grouped into arrays of two or more constituents to increase total effective sensing surface area. Additionally or alternatively, to obtain redundancy, multiple working electrodes may be operated as parallelized sensors to obtain a plurality of independent measures of the concentration of an analyte of interest. The working electrode can either be operated as the anode (such that an analyte is oxidized at its surface), or as the cathode (such that an analyte is reduced at its surface).

Figure 6A:
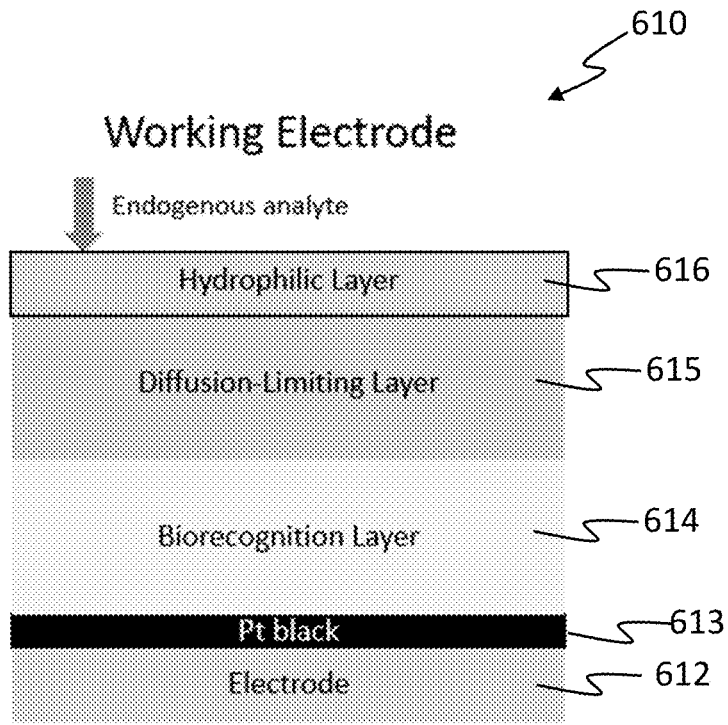
FIGS. 6A-6C depict illustrative schematics of layered structures of a working electrode, a counter electrode, and a reference electrode, respectively.

FIG. 6A depicts a schematic of an exemplary set of layers for a working electrode 610. For example, as described above, in some variations the working electrode 610 may include an electrode material 612 and a biorecognition layer including a biorecognition element. The electrode material 612 functions to encourage the electrocatalytic detection of an analyte or the product of the reaction of the analyte and the biorecognition element. The electrode material 612 also provides ohmic contact and routes an electrical signal from the electrocatalytic reaction to processing circuitry. In some variations, the electrode material 612 may include platinum as shown in FIG. 6A. However, the electrode material 612 may alternatively include, for example, palladium, iridium, rhodium, gold, ruthenium, titanium, nickel, carbon, doped diamond, or other suitable catalytic and inert material.

In some variations, the electrode material 612 may be coated with a highly porous electrocatalytic layer, such as a platinum black layer 613, which may augment the electrode surface area for enhanced sensitivity. Additionally or alternatively, the platinum black layer 613 may enable the electrocatalytic oxidation or reduction of the product of the biorecognition reaction facilitated by the biorecognition layer 614. However, in some variations the platinum black layer 613 may be omitted (as shown in FIGS. 6D and 6G, for example). The electrode may enable the electrocatalytic oxidation or reduction of the product of the biorecognition reaction if the platinum black layer 613 is not present.

The biorecognition layer 614 may be arranged over the electrode material 612 (or platinum black layer 613 if it is present) and functions to immobilize and stabilize the biorecognition element which facilitates selective analyte quantification for extended time periods. In some variations, the biorecognition element may include an enzyme, such as an oxidase. As an exemplary variation for use in a glucose monitoring system, the biorecognition element may include glucose oxidase, which converts glucose, in the presence of oxygen, to an electroactive product (i.e., hydrogen peroxide) that can be detected at the electrode surface. Specifically, the redox equation associated with this exemplary variation is Glucose+Oxygen→Hydrogen Peroxide+Gluconolactone (mediated by glucose oxidase); Hydrogen Peroxide→Water+Oxygen (mediated by applying an oxidizing potential at the working electrode).

However, in other variations the biorecognition element may additionally or alternatively comprise another suitable oxidase or oxidoreductase enzyme such as lactate oxidase, alcohol oxidase, beta-hydroxybutyrate dehydrogenase, tyrosinase, catalase, ascorbate oxidase, cholesterol oxidase, choline oxidase, pyruvate oxidase, urate oxidase, urease, and/or xanthine oxidase.

In some variations, the biorecognition element may be cross-linked with an amine-condensing carbonyl chemical species that may help stabilize the biorecognition element within the biorecognition layer 614. As further described below, in some variations, the cross-linking of the biorecognition element may result in the microneedle array being compatible with ethylene oxide (EO) sterilization, which permits exposure of the entire analyte monitoring device (including sensing elements and electronics) to the same sterilization cycle, thereby simplifying the sterilization process and lowering manufacture costs. For example, the biorecognition element may be cross-linked with glutaraldehyde, formaldehyde, glyoxal, malonaldehyde, succinaldehyde, and/or other suitable species. In some variations, the biorecognition element may be cross-linked with such an amine-condensing carbonyl chemical species to form cross-linked biorecognition element aggregates. Cross-linked biorecognition element aggregates that have at least a threshold molecular weight may then be embedded in a conducting polymer. By embedding only those aggregates that have a threshold molecular weight, any uncross-linked enzymes may be screened out and not incorporated into the biorecognition layer. Accordingly, only aggregates having a desired molecular weight may be selected for use in the conducting polymer, to help ensure that only sufficiently stabilized, cross-linked enzyme entities are included in the biorecognition layer, thereby contributing to a biorecognition layer that is overall better suited for EO sterilization without loss in sensing performance. In some variations, only cross-linked aggregates that have a molecular weight that is at least twice that of glucose oxidase may be embedded in the conducting polymer.

In some variations, the conducting polymer may be permselective to contribute to the biorecognition layer's robustness against circulating androgynous electroactive species (e.g., ascorbic acid, vitamin C, etc.), fluctuations of which may adversely affect the sensitivity of the sensor. Such a permselective conducting polymer in the biorecognition layer may further be more robust against pharmacological interferences (e.g., acetaminophen) in the interstitial fluid that may affect sensor accuracy. Conducting polymers may be made permselective by, for example, removing excess charge carriers by an oxidative electropolymerization process or by neutralizing these charge carriers with a counter-ion dopant, thereby transforming the conducting polymer into a non-conducting form. These oxidatively-polymerized conducting polymers exhibit permselectivity and are hence able to reject ions of similar charge polarity to the dopant ion (net positive or negative) or by via size exclusion due to the dense and compact form of the conducting polymers.

Furthermore, in some variations the conducting polymer may exhibit self-sealing and/or self-healing properties. For example, the conducting polymer may undergo oxidative electropolymerization, during which the conducting polymer may lose its conductivity as the thickness of the deposited conducting polymer on the electrode increases, until the lack of sufficient conductivity causes the deposition of additional conducting polymer to diminish. In the event that the conducting polymer has succumbed to minor physical damage (e.g., during use), the polymeric backbone may re-assemble to neutralize free charge and thereby lower overall surface energy of the molecular structure, which may manifest as self-sealing and/or self-healing properties.

In some variations, the working electrode may further include a diffusion-limiting layer 1615 arranged over the biorecognition layer 614. The diffusion-limiting layer 615 may function to limit the flux of the analyte of interest in order to reduce the sensitivity of the sensor to endogenous oxygen fluctuations. For example, the diffusion-limiting layer 615 may attenuate the concentration of the analyte of interest so that it becomes the limiting reactant to an aerobic enzyme. However, in some variation (e.g., if the biorecognition element is not aerobic), the diffusion-limiting layer 615 may be omitted.

The working electrode may further include, in some variations, a hydrophilic layer 616 that provides for a biocompatible interface to, for example, reduce the foreign body response. However, in some variations the hydrophilic layer 616 may be omitted (e.g., if the diffusion-limiting layer expresses hydrophilic moieties to serve this purpose), as shown in FIGS. 6D and 6G, for example.

Counter Electrode

As described above, the counter electrode is the electrode that is sourcing or sinking electrons (via an electrical current) required to sustain the electrochemical reaction at the working electrode. The number of counter electrode constituents can be augmented in the form of a counter electrode array to enhance surface area such that the current-carrying capacity of the counter electrode does not limit the redox reaction of the working electrode. It thus may be desirable to have an excess of counter electrode area versus the working electrode area to circumvent the current-carrying capacity limitation. If the working electrode is operated as an anode, the counter electrode will serve as the cathode and vice versa. Similarly, if an oxidation reaction occurs at the working electrode, a reduction reaction occurs at the counter electrode and vice versa. Unlike the working or reference electrodes, the counter electrode is permitted to dynamically swing to electrical potentials required to sustain the redox reaction of interest on the working electrode.

Figure 6B:
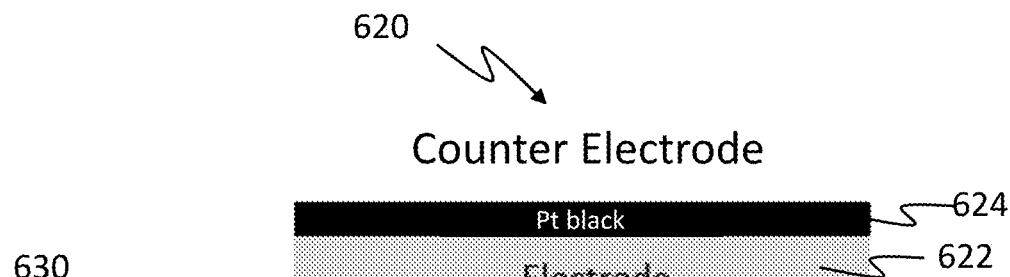

As shown in FIG. 6B, a counter electrode 620 may include an electrode material 622, similar to electrode material 612. For example, like the electrode material 612, the electrode material 622 in the counter electrode 620 may include a noble metal such as gold, platinum, palladium, iridium, carbon, doped diamond, and/or other suitable catalytic and inert material.

In some variations, the counter electrode 620 may have few or no additional layers over the electrode material 632. However, in some variations the counter electrode 620 may benefit from increase surface area to increase the amount of current it can support. For example, the counter electrode material 632 may be textured or otherwise roughened in such a way to augment the surface area of the electrode material 632 for enhanced current sourcing or sinking ability. Additionally or alternatively, the counter electrode 620 may include a layer of platinum black 624, which may augment electrode surface as described above with respect to some variations of the working electrode. However, in some variations of the counter electrode, the layer of platinum black may be omitted (e.g., as shown in FIG. 6E). In some variations, the counter electrode may further include, a hydrophilic layer that provides for a biocompatible interface to, for example, reduce the foreign body response.

Figure 6C:
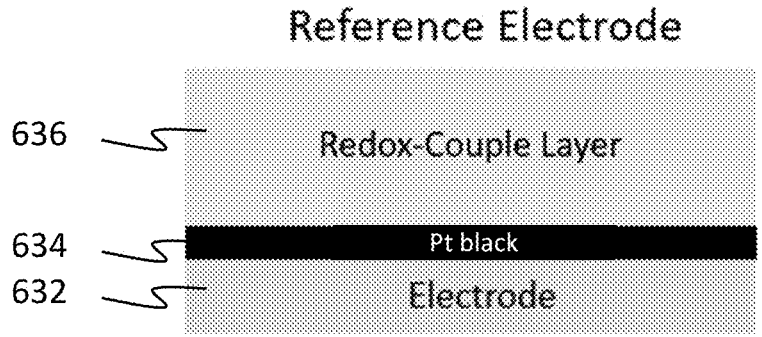
Figure 6D:
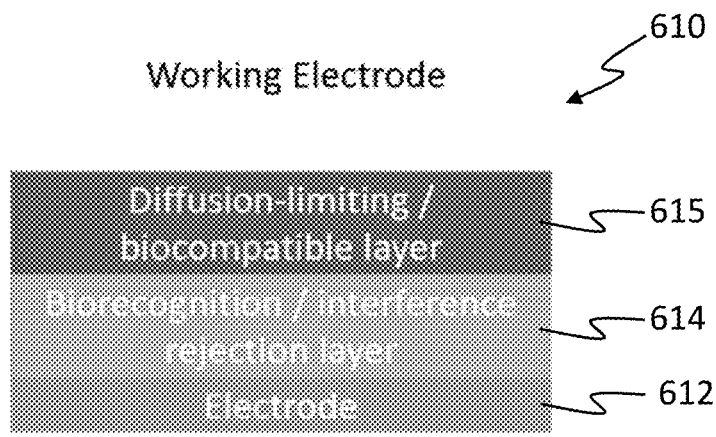
FIGS. 6D-6F depict illustrative schematics of layered structures of a working electrode, a counter electrode, and a reference electrode, respectively.
Figure 6E:
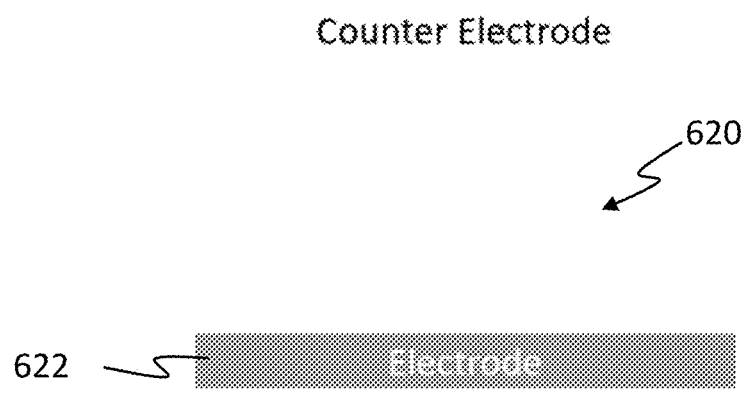
Figure 6F:
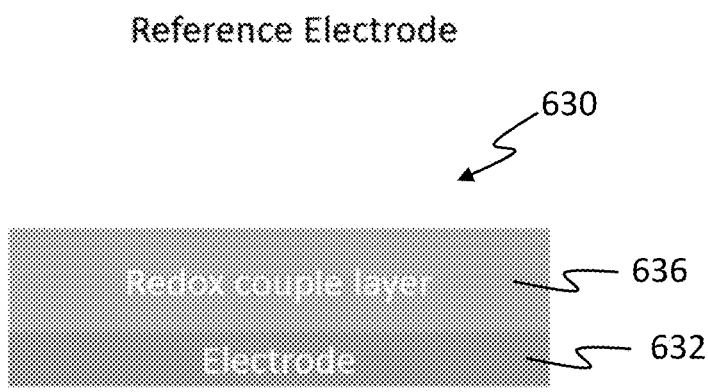
Figure 6G:
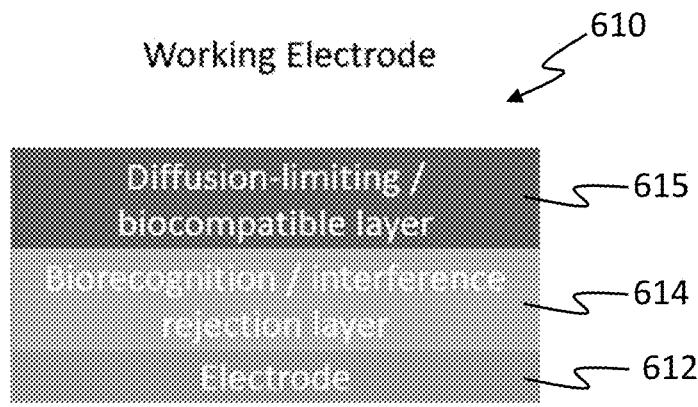
FIGS. 6G-6I depict illustrative schematics of layered structures of a working electrode, a counter electrode, and a reference electrode, respectively.
Figure 6H:
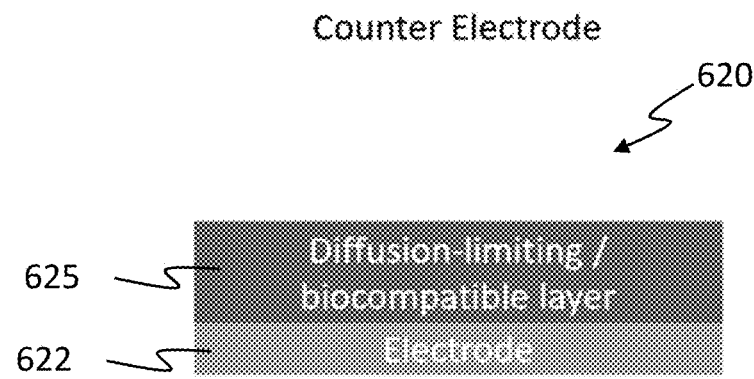

Additionally or alternatively, in some variations as shown in FIG. 6H, the counter electrode 620 may include a diffusion-limiting layer 625 (e.g., arranged over the electrode). The diffusion-limiting layer 625 may, for example, be similar to the diffusion-limiting layer 615 described above with respect to FIG. 6A.

Reference Electrode

As described above, the reference electrode functions to provide a reference potential for the system; that is, the electrical potential at which the working electrode is biased is referenced to the reference electrode. A fixed or at least controlled potential relationship may be established between the working and reference electrodes, and within practical limits no current is sourced from or sinked to the reference electrode.

As shown in FIG. 6C, a reference electrode 630 may include an electrode material 632, similar to electrode material 612. In some variations, like the electrode material 612, the electrode material 632 in the reference electrode 630 may include a metal salt or metal oxide, which serves as a stable redox coupled with a well-known electrode potential. For example, the metal salt may, for example, include silver-silver chloride (Ag/AgCl) and the metal oxide may include iridium oxide ($IrOx/Ir_2O_3/IrO_2$). In other variations, noble and inert metal surfaces may function as quasi-reference electrodes and include gold, platinum, palladium, iridium, carbon, doped diamond, and/or other suitable catalytic and inert material. Furthermore, in some variations the reference electrode 630 may be textured or otherwise roughened in such a way to enhance adhesion with any subsequent layers. Such subsequent layers on the electrode material 632 may include a platinum black layer 634. However, in some variations, the platinum black layer may be omitted (e.g., as shown in FIGS. 6F and 6I).

The reference electrode 630 may, in some variations, further include a redox-couple layer 636, which main contain a surface-immobilized, solid-state redox couple with a stable thermodynamic potential. For example, the reference electrode may operate at a stable standard thermodynamic potential with respect to a standard hydrogen electrode (SHE). The high stability of the electrode potential may be attained by employing a redox system with constant (e.g., buffered or saturated) concentrations of each participant of the redox reaction. For example, the reference electrode may include saturated Ag/AgCl (E=+0.197V vs. SHE) or IrOx (E=+0.177 vs. SHE, pH=7.00) in the redox-couple layer 636. Other examples of redox-couple layers 636 may include a suitable conducting polymer with a dopant molecule such as that described in U.S. Patent Pub. No. 2019/0309433, which is incorporated in its entirety herein by this reference. In some variations, the reference electrode may be used as a half-cell to construct a complete electrochemical cell.

Figure 6I:
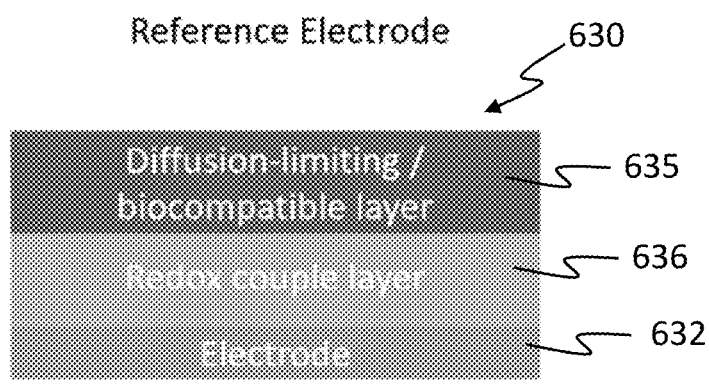

Additionally or alternatively, in some variations as shown in FIG. 6I, the reference electrode 630 may include a diffusion-limiting layer 635 (e.g., arranged over the electrode and/or the redox-couple layer). The diffusion-limiting layer 635 may, for example, be similar to the diffusion-limiting layer 615 described above with respect to FIG. 16A.

Exemplary Electrode Layer Formation

Various layers of the working electrode, counter electrode, and reference electrode may be applied to the microneedle array and/or functionalized, etc. using suitable processes such as those described below.

In a pre-processing step for the microneedle array, the microneedle array may be plasma cleaned in an inert gas (e.g., RF-generated inert gas such as argon) plasma environment to render the surface of the material, including the electrode material (e.g., electrode material 612, 622, and 632 as described above), to be more hydrophilic and chemically reactive. This pre-processing functions to not only physically remove organic debris and contaminants, but also to clean and prepare the electrode surface to enhance adhesion of subsequently deposited films on its surface.

Multiple microneedles (e.g., any of the microneedle variations described herein, each of which may have a working electrode, counter electrode, or reference electrode as described above) may be arranged in a microneedle array. Considerations of how to configure the microneedles include factors such as desired insertion force for penetrating skin with the microneedle array, optimization of electrode signal levels and other performance aspects, manufacturing costs and complexity, etc.

For example, the microneedle array may include multiple microneedles that are spaced apart at a predefined pitch (distance between the center of one microneedle to the center of its nearest neighboring microneedle). In some variations, the microneedles may be spaced apart with a sufficient pitch so as to distribute force (e.g., avoid a "bed of nails" effect) that is applied to the skin of the user to cause the microneedle array to penetrate the skin. As pitch increases, force required to insert the microneedle array tends to decrease and depth of penetration tends to increase. However, it has been found that pitch only begins to affect insertion force at low values (e.g., less than about 150 µm). Accordingly, in some variations the microneedles in a microneedle array may have a pitch of at least 200 µm, at least 300 µm, at least 400 µm, at least 500 µm, at least 600 µm, at least 700 µm, or at least 750 µm. For example, the pitch may be between about 200 µm and about 800 µm, between about 300 µm and about 700 µm, or between about 400 µm and about 600 µm. In some variations, the microneedles may be arranged in a periodic grid, and the pitch may be uniform in all directions and across all regions of the microneedle array. Alternatively, the pitch may be different as measured along different axes (e.g., X, Y directions) and/or some regions of the microneedle array may include a smaller pitch while other may include a larger pitch.

Figure 7:
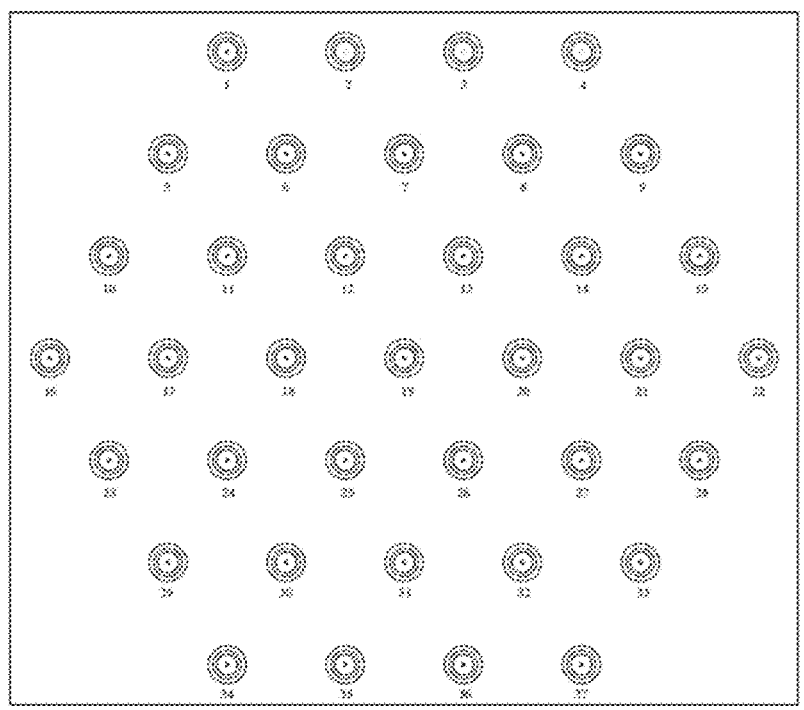
FIG. 7 depicts an illustrative schematic of a microneedle array configuration.
Figure 8A:
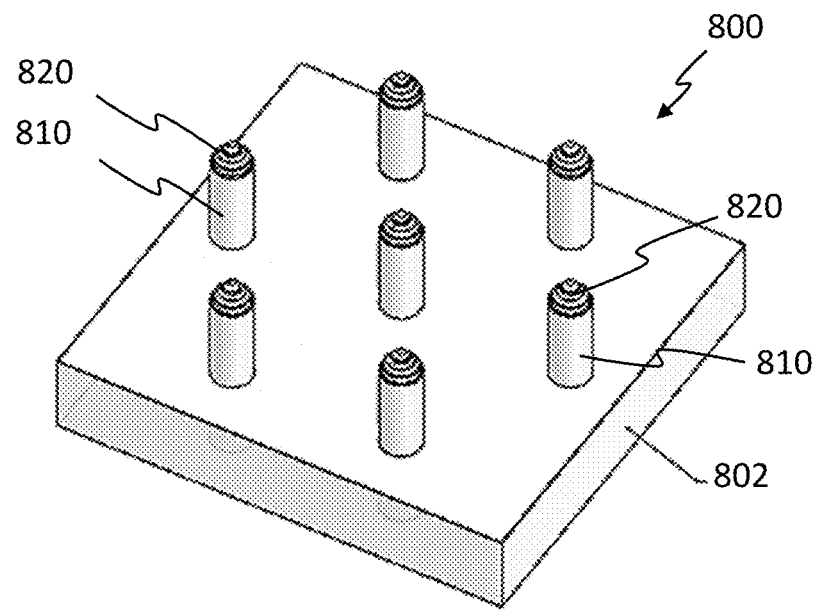
FIGS. 8A-8D depict illustrative schematics of a microneedle array configuration.

Furthermore, for more consistent penetration, microneedles may be spaced equidistant from one another (e.g., same pitch in all directions). To that end, in some variations, the microneedles in a microneedle array may be arranged in a hexagonal configuration as shown in FIG. 7. Alternatively, the microneedles in a microneedle array may arranged in a rectangular array (e.g., square array), or in another suitable symmetrical manner Another consideration for determining configuration of a microneedle array is overall signal level provided by the microneedles. Generally, signal level at each microneedle is invariant of the total number of microneedle elements in an array. However, signal levels can be enhanced by electrically interconnecting multiple microneedles together in an array. For example, an array with a large number of electrically connected microneedles is expected to produce a greater signal intensity (and hence increased accuracy) than one with fewer microneedles. However, a higher number of microneedles on a die will increase die cost (given a constant pitch) and will also require greater force and/or velocity to insert into skin. In contrast, a lower number of microneedles on a die may reduce die cost and enable insertion into the skin with reduced application force and/or velocity. Furthermore, in some variations a lower number of microneedles on a die may reduce the overall footprint area of the die, which may lead to less unwanted localized edema and/or erythema. Accordingly, in some variations, a balance among these factors may be achieved with a microneedle array including 37 microneedles as shown in FIG. 7 or a microneedle array including 7 microneedles are shown in FIGS. 8A8C. However, in other variations there may be fewer microneedles in an array (e.g., between about 5 and about 35, between about 5 and about 30, between about 5 and about 25, between about 5 and about 20, between about 5 and about 15, between about 5 and about 100, between about 10 and about 30, between about 15 and about 25, etc.) or more microneedles in an array (e.g., more than 37, more than 40, more than 45, etc.).

Additionally, as described in further detail below, in some variations only a subset of the microneedles in a microneedle array may be active during operation of the analyte monitoring device. For example, a portion of the microneedles in a microneedle array may be inactive (e.g., no signals read from electrodes of inactive microneedles). In some variations, a portion of the microneedles in a microneedle array may be activated at a certain time during operation and remain active for the remainder of the operating lifetime of the device. Furthermore, in some variations, a portion of the microneedles in a microneedle array may additionally or alternatively be deactivated at a certain time during operation and remain inactive for the remainder of the operating lifetime of the device.

In considering characteristics of a die for a microneedle array, die size is a function of the number of microneedles in the microneedle array and the pitch of the microneedles. Manufacturing costs are also a consideration, as a smaller die size will contribute to lower cost since the number of dies that can be formed from a single wafer of a given area will increase. Furthermore, a smaller die size will also be less susceptible to brittle fracture due to the relative fragility of the substrate.

Furthermore, in some variations, microneedles at the periphery of the microneedle array (e.g., near the edge or boundary of the die, near the edge or boundary of the housing, near the edge or boundary of an adhesive layer on the housing, along the outer border of the microneedle array, etc.) may be found to have better performance (e.g., sensitivity) due to better penetration compared to microneedles in the center of the microneedle array or die. Accordingly, in some variations, working electrodes may be arranged largely or entirely on microneedles located at the periphery of the microneedle array, to obtain more accurate and/or precise analyte measurements.

FIG. 7 depicts an illustrative schematic of 37 microneedles arranged in an example variation of a microneedle array. The 37 microneedles may, for example, be arranged in a hexagonal array with an inter-needle center-to-center pitch of about 750 μm (or between about 700 μm and about 800 μm, or between about 725 μm and about 775 μm) between the center of each microneedle and the center of its immediate neighbor in any direction.

Figure 8B:
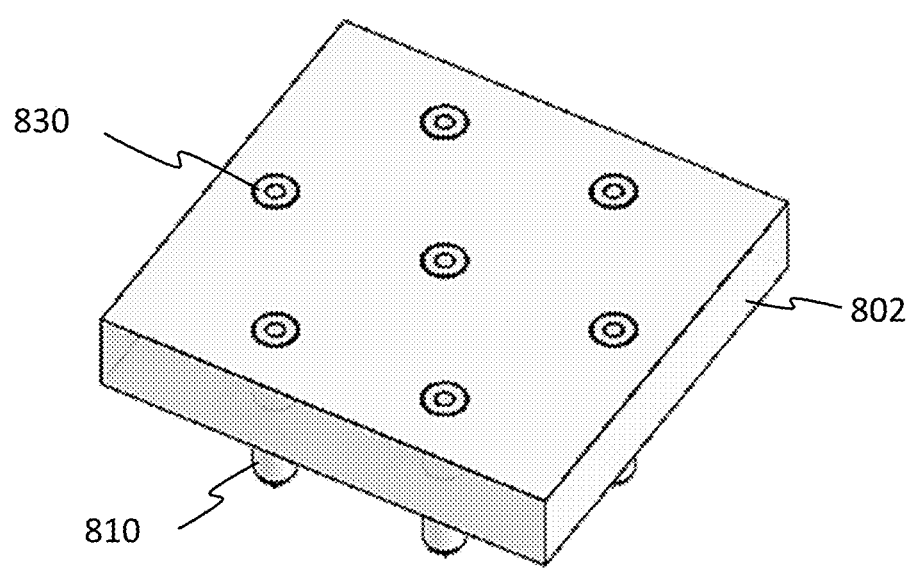
Figure 8C:
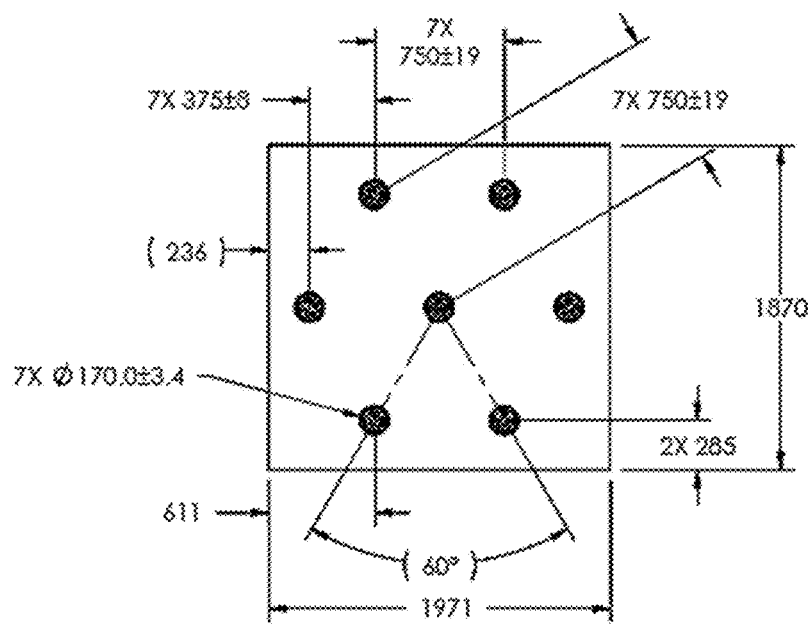
Figure 8D:
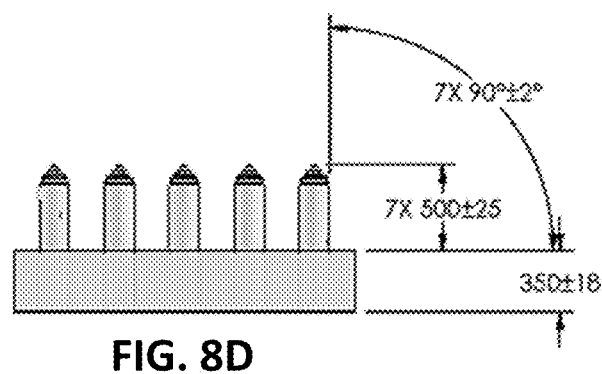

FIGS. 8A and 8B depict perspective views of an illustrative schematic of seven microneedles 810 arranged in an example variation of a microneedle array 800. The seven microneedles 810 are arranged in a hexagonal array on a substrate 802. As shown in FIG. 8A, the electrodes 820 are arranged on distal portions of the microneedles 810 extending from a first surface of the substrate 802. As shown in FIG. 8B, proximal portions of the microneedles 810 are conductively connected to respective backside electrical contacts 830 on a second surface of the substrate 802 opposite the first surface of the substrate 802. FIGS. 8C and 8D depict plan and side views of an illustrative schematic of a microneedle array similar to microneedle array 800. As shown in FIGS. 8C and 8D, the seven microneedles are arranged in a hexagonal array with an inter-needle center-to-center pitch of about 750 μm between the center of each microneedle and the center of its immediate neighbor in any direction. In other variations the inter-needle center-to-center pitch may be, for example, between about 700 μm and about 800 μm, or between about 725 μm and about 775 μm. The microneedles may have an approximate outer shaft diameter of about 170 μm (or between about 150 μm and about 190 μm, or between about 125 μm and about 200 μm) and a height of about 500 μm (or between about 475 μm and about 525 μm, or between about 450 μm and about 550 μm).

Furthermore, the microneedle arrays described herein may have a high degree of configurability concerning where the working electrode(s), counter electrode(s), and reference electrode(s) are located within the microneedle array. This configurability may be facilitated by the electronics system.

Figure 9A:
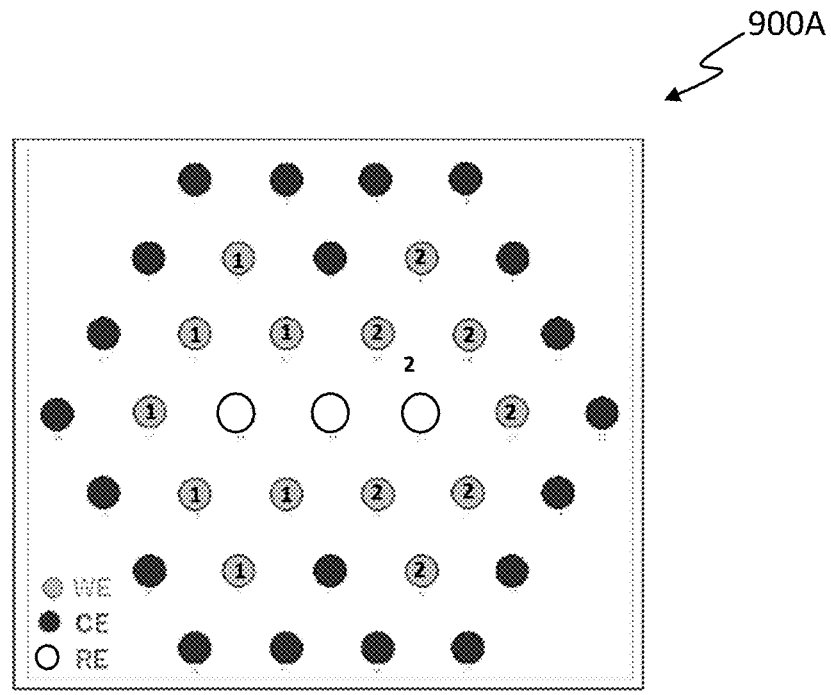
FIGS. 9A-9J depict illustrative schematics of different variations of microneedle array configurations.

In some variations, a microneedle array may include electrodes distributed in two or more groups in a symmetrical or non-symmetrical manner in the microneedle array, with each group featuring the same or differing number of electrode constituents depending on requirements for signal sensitivity and/or redundancy. For example, electrodes of the same type (e.g., working electrodes) may be distributed in a bilaterally or radially symmetrical manner in the microneedle array. For example, FIG. 9A depicts a variation of a microneedle array 900A including two symmetrical groups of seven working electrodes (WE), with the two working electrode groups labeled "1" and "2". In this variation, the two working electrode groups are distributed in a bilaterally symmetrical manner within the microneedle array. The working electrodes are generally arranged between a central region of three reference electrodes (RE) and an outer perimeter region of twenty counter electrodes (CE). In some variations, each of the two working electrode groups may include seven working electrodes that are electrically connected amongst themselves (e.g., to enhance sensor signal). Alternatively, only a portion of one or both of the working electrode groups may include multiple electrodes that are electrically connected amongst themselves. As yet another alternative, the working electrode groups may include working electrodes that are standalone and not electrically connected to other working electrodes. Furthermore, in some variations the working electrode groups may be distributed in the microneedle array in a non-symmetrical or random configuration.

Figure 9B:
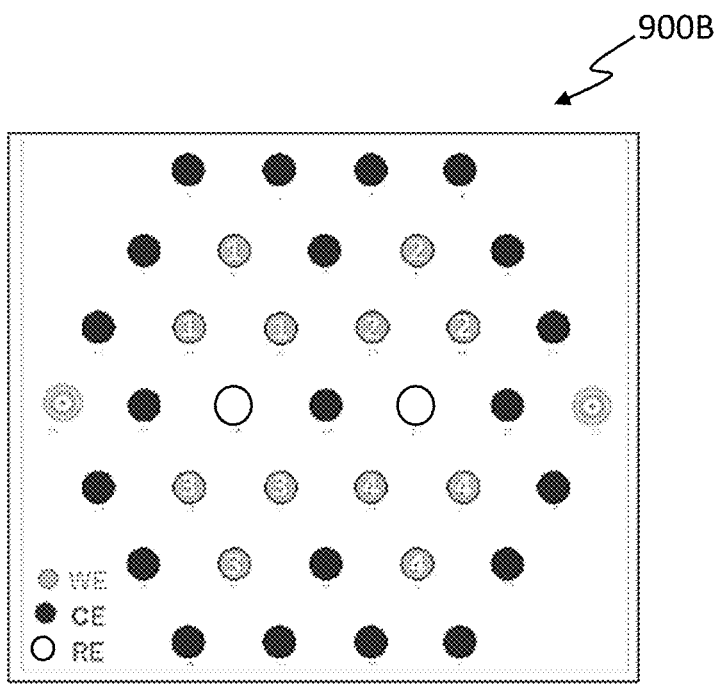

As another example, FIG. 9B depicts a variation of a microneedle array 900B including four symmetrical groups of three working electrodes (WE), with the four working electrode groups labeled "1", "2", "3", and "4." In this variation, the four working electrode groups are distributed in a radially symmetrical manner in the microneedle array. Each working electrode group is adjacent to one of two reference electrode (RE) constituents in the microneedle array and arranged in a symmetrical manner. The microneedle array also includes counter electrodes (CE) arranged around the perimeter of the microneedle array, except for two electrodes on vertices of the hexagon that are inactive or may be used for other features or modes of operation.

Figure 9C:
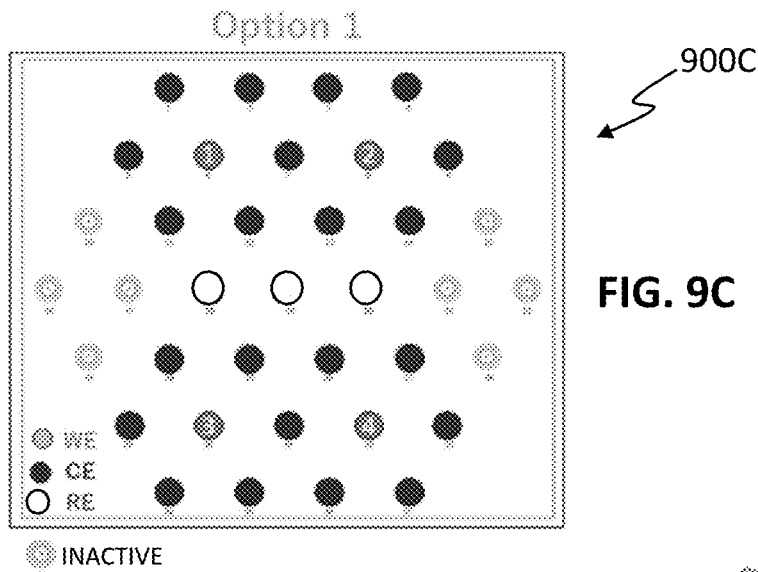

In some variations, only a portion of microneedle array may include active electrodes. For example, FIG. 9C depicts a variation of a microneedle array 900C with 37 microneedles and a reduced number of active electrodes, including four working electrodes (labeled "1", "2", "3", and "4") in a bilaterally symmetrical arrangement, twenty-two counter electrodes, and three reference electrodes. The remaining eight electrodes in the microneedle array are inactive. In the microneedle array shown in FIG. 9C, each of the working electrodes is surrounded by a group of counter electrodes. Two groups of such clusters of working electrodes and counter electrodes are separated by a row of the three reference electrodes.

Figure 9D:
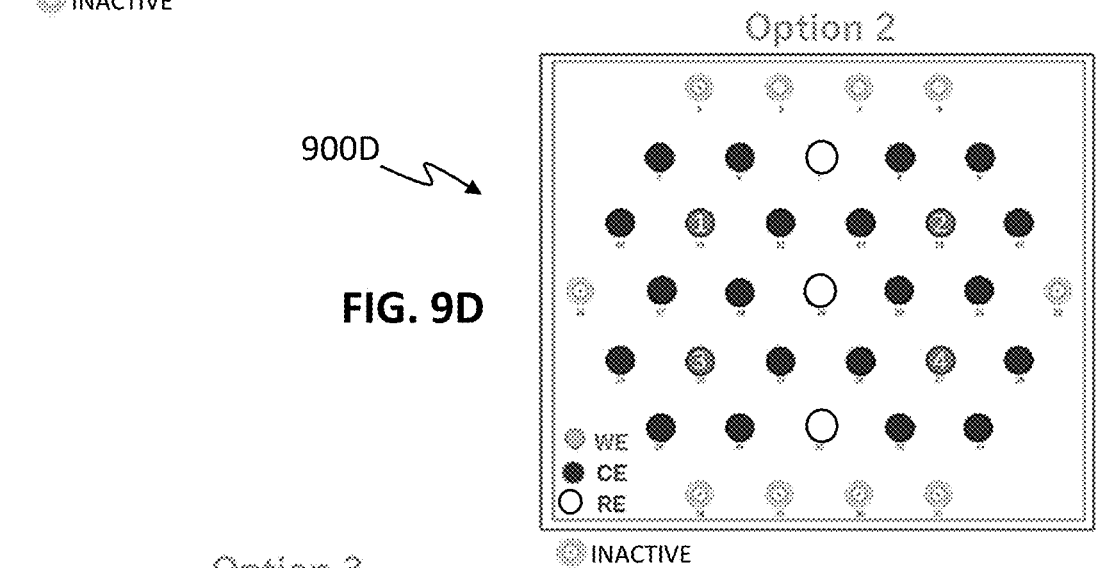

As another example, FIG. 9D depicts a variation of a microneedle array 900D with 37 microneedles and a reduced number of active electrodes, including four working electrodes (labeled "1", "2", "3", and "4") in a bilaterally symmetrical arrangement, twenty counter electrodes, and three reference electrodes, where the remaining ten electrodes in the microneedle array are inactive.

Figure 9E:
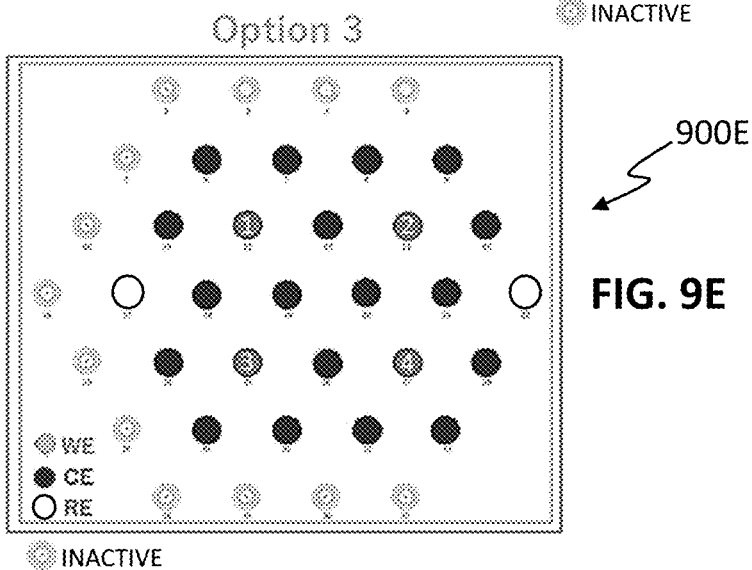

As another example, FIG. 9E depicts a variation of a microneedle array 900E with 37 microneedles and a reduced number of active electrodes, including four working electrodes (labeled "1", "2", "3", and "4"), eighteen counter electrodes, and two reference electrodes. The remaining thirteen electrodes in the microneedle array are inactive. The inactive electrodes are along a partial perimeter of the overall microneedle array, thereby reducing the effective size and shape of the active microneedle arrangement to a smaller hexagonal array. Within the active microneedle arrangement, the four working electrodes are generally in a radially symmetrical arrangement, and each of the working electrodes is surrounded by a group of counter electrodes.

Figure 9F:
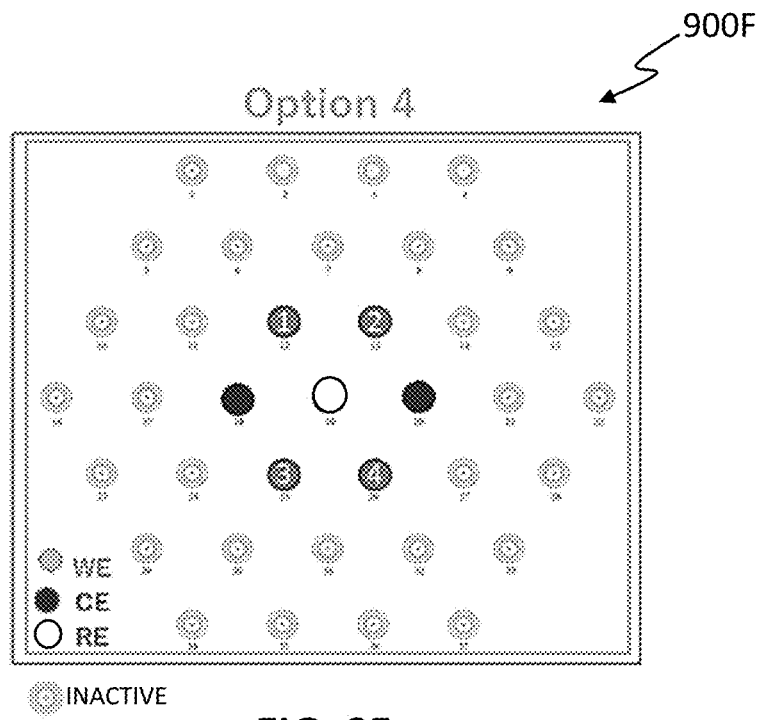

FIG. 9F depicts another example variation of a microneedle array 900F with 37 microneedles and a reduced number of active electrodes, including four working electrodes (labeled "1", "2", "3", and "4"), two counter electrodes, and one reference electrode. The remaining thirty electrodes in the microneedle array are inactive. The inactive electrodes are arranged in two layers around the perimeter of the overall microneedle array, thereby reducing the effective size and shape of the active microneedle arrangement to a smaller hexagonal array centered around the reference electrode. Within the active microneedle arrangement, the four working electrodes are in a bilaterally symmetrical arrangement and the counter electrodes are equidistant from the central reference electrode.

Figure 9G:
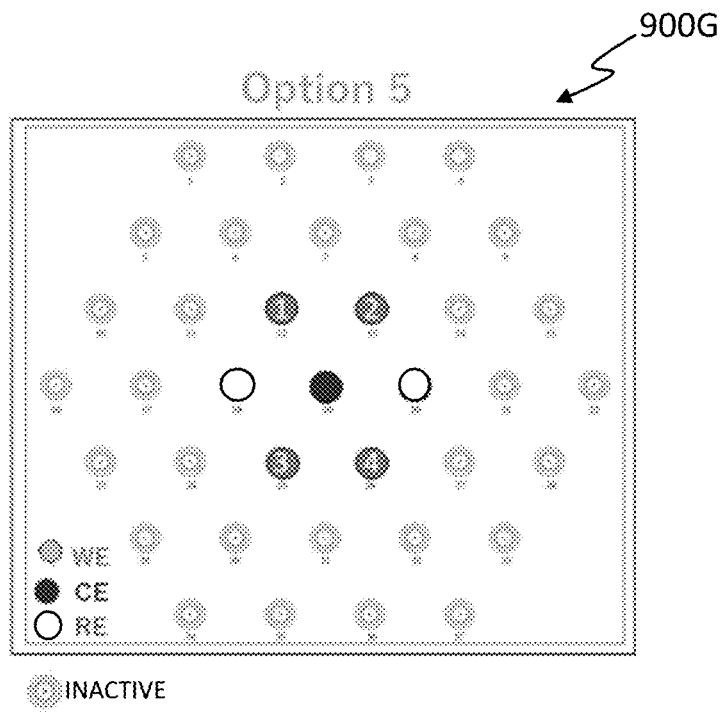

FIG. 9G depicts another example variation of a microneedle array 900G with 37 microneedles and a reduced number of active electrodes. The active electrodes in microneedle array 900G are arranged in a similar manner as that in microneedle array 900F shown in FIG. 9F, except that the microneedle array 900G includes one counter electrode and two reference electrodes, and the smaller hexagonal array of active microneedles is centered around the counter electrode. Within the active microneedle arrangement, the four working electrodes are in a bilaterally symmetrical arrangement and the reference electrodes are equidistant from the central counter electrode.

Figure 9H:
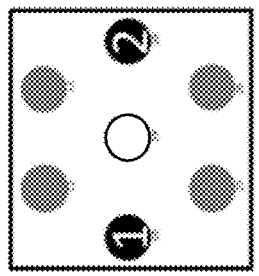

FIG. 9H depicts another example variation of a microneedle array 900H with seven microneedles. The microneedle arrangement contains two microneedles assigned as independent working electrodes (1 and 2), a counter electrode contingent comprised of four microneedles, and a single reference electrode. There is bilateral symmetry in the arrangement of working and counter electrodes, which are equidistant from the central reference electrode. Additionally, the working electrodes are arranged as far as possible from the center of the microneedle array (e.g., at the periphery of the die or array) to take advantage of a location where the working electrodes are expected to have greater sensitivity and overall performance.

Figure 9I:
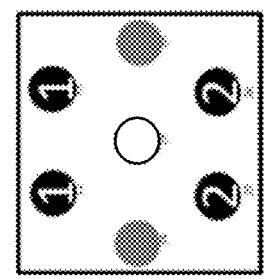

FIG. 9I depicts another example variation of a microneedle array 900I with seven microneedles. The microneedle arrangement contains four microneedles assigned as two independent groupings (1 and 2) of two working electrodes each, a counter electrode contingent comprised of two microneedles, and a single reference electrode. There is bilateral symmetry in the arrangement of working and counter electrodes, which are equidistant from the central reference electrode. Additionally, the working electrodes are arranged as far as possible from the center of the microneedle array (e.g., at the periphery of the die or array) to take advantage of a location where the working electrodes are expected to have greater sensitivity and overall performance.

Figure 9J:
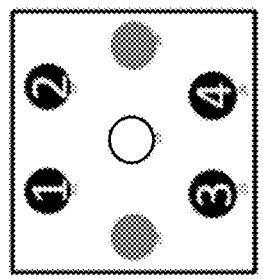

FIG. 9J depicts another example variation of a microneedle array 900J with seven microneedles. The microneedle arrangement contains four microneedles assigned as independent working electrodes (1, 2, 3, and 4), a counter electrode contingent comprised of two microneedles, and a single reference electrode. There is bilateral symmetry in the arrangement of working and counter electrodes, which are equidistant from the central reference electrode. Additionally, the working electrodes are arranged as far as possible from the center of the microneedle array (e.g., at the periphery of the die or array) to take advantage of a location where the working electrodes are expected to have greater sensitivity and overall performance.

While FIGS. 9A-9J illustrate example variations of microneedle array configurations, it should be understood that these figures are not limiting and other microneedle configurations (including different numbers and/or distributions of working electrodes, counter electrodes, and reference electrodes, and different numbers and/or distributions of active electrodes and inactive electrodes, etc.) may be suitable in other variations of microneedle arrays.

Analog Front End

In some variations, the electronics system of the analyte monitoring device may include an analog front end. The analog front end may include sensor circuitry (e.g., sensor circuitry 124 as shown in FIG. 2A) that converts analog current measurements to digital values that can be processed by the microcontroller. The analog front end may, for example, include a programmable analog front end that is suitable for use with electrochemical sensors. For example, the analog front end may include a MAX30131, MAX30132, or MAX30134 component (which have 1, 2, and 4 channel, respectively), available from Maxim Integrated (San Jose, Calif.), which are ultra-low power programmable analog front ends for use with electrochemical sensors. The analog front end may also include an AD5940 or AD5941 component, available from Analog Devices (Norwood, Mass.), which are high precision, impedance and electrochemical front ends. Similarly, the analog front end may also include an LMP91000, available from Texas Instruments (Dallas, Tex.), which is a configurable analog front end potentiostat for low-power chemical sensing applications. The analog front end may provide biasing and a complete measurement path, including the analog to digital converters (ADCs). Ultra-low power may allow for the continuous biasing of the sensor to maintain accuracy and fast response when measurement is required for an extended duration (e.g. 7 days) using a body-worn, battery-operated device.

In some variations, the analog front end device may be compatible with both two and three terminal electrochemical sensors, such as to enable both DC current measurement, AC current measurement, and electrochemical impedance spectroscopy (EIS) measurement capabilities. Furthermore, the analog front end may include an internal temperature sensor and programmable voltage reference, support external temperature monitoring and an external reference source and integrate voltage monitoring of bias and supply voltages for safety and compliance.

In some variations, the analog front end may include a multi-channel potentiostat to multiplex sensor inputs and handle multiple signal channels. For example, the analog front end may include a multi-channel potentiostat such as that described in U.S. Pat. No. 9,933,387, which is incorporated herein in its entirety by this reference.

In some variations, the analog front end and peripheral electronics may be integrated into an application-specific integrated circuit (ASIC), which may help reduce cost, for example. This integrated solution may include the microcontroller described below, in some variations.

Microcontroller

In some variations, the electronics system of the analyte monitoring device may include at least one microcontroller (e.g., controller 122 as shown in FIG. 2A). The microcontroller may include, for example, a processor with integrated flash memory. In some variations, the microcontroller in the analyte monitoring device may be configured to perform analysis to correlate sensor signals to an analyte measurement (e.g., glucose measurement). For example, the microcontroller may execute a programmed routine in firmware to interpret the digital signal (e.g., from the analog front end), perform any relevant algorithms and/or other analysis, and route processed data to and/or from the communication module. Keeping the analysis on-board the analyte monitoring device may, for example, enable the analyte monitoring device to broadcast analyte measurement(s) to multiple devices (e.g., mobile computing devices such as a smartphone or smartwatch, therapeutic delivery systems such as insulin pens or pumps, etc.) in parallel, while ensuring that each connected device has the same information.

In some variations, the microcontroller may be configured to activate and/or inactivate the analyte monitoring device on one or more detected conditions. For example, the device may be configured to power on the analyte monitoring device upon insertion of the microneedle array into skin. This may, for example, enable a power-saving feature in which the battery is disconnected until the microneedle array is placed in skin, at which time the device may begin broadcasting sensor data. Such a feature may, for example, help improve the shelf life of the analyte monitoring device and/or simplify the analyte monitoring device-external device pairing process for the user.

Aspects of the current subject matter are directed to fault detection, as well as diagnostics related to the fault detection, in a microneedle array-based analyte monitoring device, such as the analyte monitoring device 110. The electrochemical sensors (e.g., electrodes of the analyte monitoring device 110) configured for measuring one or more target analytes may experience various faults during use of the analyte monitoring device 110. A fault may be a failure of one or more aspects of the analyte monitoring device 110 in which the failure affects operation of the analyte monitoring device 110. Examples of faults include degradation of the electrode membrane (e.g., cracking, delamination, and/or other damage to the membrane structure and/or surface that affects sensing), degradation of the biorecognition element (e.g., inactivation and/or denaturation), a physiologic response to implantation of the microneedle array (e.g., a foreign body response, encapsulation, protein adhesion, or collagen formation occurring in response to the insertion of the microneedles on which the electrodes are formed), improper placement or insertion of the microneedle array (e.g., the microneedles, on which the electrodes are formed, not placed at a sufficient depth for the analyte sensing), pressure attenuation (e.g., pressure applied to the analyte monitoring device 110), and external environmental influences (e.g., external impact to the electronics of the analyte monitoring device 110). The fault may affect the electrical and/or electrochemical behavior of the analyte monitoring device 110, resulting in errors and/or unreliability in measurements of the target analyte or analytes. In some instances, the fault may be temporary, such as in the case of pressure attenuations. In other instances, the fault may permanently affect operation of the analyte monitoring device 110.

Some faults may be detectable by monitoring the current draw. For example, a value of the sensing current at the working electrode of the analyte monitoring device 110 may indicate and/or correlate to some faults. In these instances, if the sensing current exhibits extreme, erratic, and/or unexpected behaviors or patterns, the fault may be determinable based on characteristics of the exhibited behaviors or patterns of the sensing current. The extreme, erratic, and/or unexpected behaviors or patterns of the sensing current may be characterized by rapid rates of change that are non-physiologically capable or possible. High noise may also contribute to the behaviors or patterns of the sensing current.

Other faults, however, may not impact the sensing current while still impacting the electrical and/or electrochemical behavior of the analyte monitoring device 110. An alternative or additional variable is thus needed for insight to and verification of changes to the electrical and/or electrochemical behavior of the analyte monitoring device 110. Voltage at the counter electrode is an example of a variable that provides such insight and verification. Thus, by monitoring the voltage at the counter electrode, a fault may be detected.

While various types of faults, such as those described above, may occur, faults may generally be characterized by if the analyte monitoring device 110 can recover from the fault (e.g., the fault is temporary) or if the analyte monitoring device 110 is damaged and operation should cease (e.g., the fault is permanent). By monitoring the counter electrode voltage, as well as, in some variations, how the counter electrode voltage corresponds with or is correlated to the sensing current, such a characterization may be made and a response to the fault may be determined. The response to the fault may be in the form of a mode of operation in which to operate the analyte monitoring device. For example, if the fault is temporary, the mode of operation may include blanking and/or disregarding any sensing data during the fault. In this situation, sensing data is inaccurate and thus not reported to the user or used for operational purposes. If the fault is permanent, the mode of operation may be to stop operation of the analyte monitoring device. In some variations, this may include ceasing application of a bias potential between the working electrode and the reference electrode.

In some variations, the counter electrode voltage is monitored to identify one or more characteristics that may serve as an indication of a fault. The characteristics indicative of a fault may include a rate of change of the counter electrode voltage and/or a lower compliance limit of the counter electrode voltage. The characteristics may be explained by considering the relationship between the counter electrode potential and the current at the working electrode. That is, as further described herein, the counter electrode voltage dynamically swings or adjusts to electrical potentials required to sustain the redox reaction at the working electrode. The counter electrode voltage may thus be considered as the voltage that is required to support the level of current at the working electrode (e.g., the sensing current). As the sensing current fluctuates or changes, the counter electrode voltage fluctuates or changes in a corresponding or reciprocal manner. If the sensing current experiences a rapid rate of change, the counter electrode voltage responds with a rapid rate of change. The correspondence, or correlation, between the sensing current and the counter electrode voltage may be defined as equal but opposite in rate of change (or near equal but opposite (e.g., up to about a 5% difference between the rates of change)). If the sensing current changes at a specified rate, the counter electrode voltage changes at the specified rate in the opposite direction. The rate of change of the counter electrode voltage then serves as an indicator of the rate of change of the sensing current. A sensing current that exhibits a rapid rate of change is non-physiologically capable or possible. Thus, by monitoring the counter electrode voltage, a determination may be made as to the physiological viability of the sensing current. As a rapid rate of change is not physiologically possible, such a change serves as an indication that something is wrong with the device. In some variations, a rapid rate of change of the counter electrode voltage may be defined as about 0.10 volts/minute. In some variations, a rapid rate of change of the counter electrode voltage may be defined as between about 0.05 volts/minute and about 0.15 volts/minute. For example, in some variations, a rapid rate of change of the counter electrode voltage may be defined as about 0.05 volts/minute, about 0.06 volts/minute, about 0.07 volts/minute, about 0.08 volts/minute, about 0.09 volts/minute, about 0.10 volts/minute, about 0.11 volts/minute, about 0.12 volts/minute, about 0.13 volts/minute, about 0.14 volts/minute, or about 0.15 volts/minute. A rapid rate of change of the sensing current may be associated with a rate of change of the analyte being measured. In the example of glucose, a rapid rate of change may be about 4 mg/dL/min. In some variations, a rapid rate of change of glucose may be between about 3.5 mg/dL/min and about 6 mg/dL/min.

The lower compliance limit of the counter electrode voltage may be defined as the lowest level to which the counter electrode voltage may swing. The counter electrode voltage may also have an upper compliance limit, the highest level to which the counter electrode may swing. If the counter electrode voltage swings to the lower compliance limit, this may serve as an indication that the sensing current reached a high magnitude current that is not physiologically capable, indicating occurrent of a fault.

Thus, the counter electrode voltage experiencing a rate of change that meets or exceeds a threshold rate of change and/or meets a threshold compliance limit serve as indications that there is a fault within the analyte monitoring device 110. In some variations, upon identifying that the rate of change of the counter electrode voltage meets or exceeds a threshold rate of change and/or that the counter electrode voltage meets a threshold compliance limit, characteristics or parameters of the counter electrode voltage may be compared to characteristics or parameters of the sensing current to determine if the fault is temporary or permanent. The comparison may include determination of the correspondence, or correlation, between the counter electrode voltage and the sensing current.

In some variations, the counter electrode voltage corresponding with the sensing current such that the counter electrode voltage is changing in an equal rate of change as that of the sensing current, is representative of a pressure-induced signal attenuation. Such a pressure-induced signal attenuation may be caused by external pressure being applied to the analyte monitoring device 110 and may be characterized as a temporary fault. When the external pressure is removed, the analyte monitoring device 110 operates as intended.

In some variations, changes in the counter electrode voltage corresponding with changes in the sensing current, such that the correspondence is maintained, coupled with the counter electrode voltage meeting a lower compliance limit is representative of changes in the physiologic environment surrounding the sensor and/or changes in the sensor surface. In other variations, the counter electrode voltage meeting the lower compliance limit, regardless of the sensing current, is representative of a change in the physiologic environment and/or changes in the sensor surface. In this scenario, the counter electrode voltage does not need to be correlated with the sensing current. Changes in the physiologic environment surrounding the sensor and changes in the sensor surface may be examples of permanent faults.

In some variations, changes in the counter electrode voltage deviating from the changes in the sensing current, such that the counter electrode voltage and the sensing current are changing in different ways, coupled with the rapid rate of change of the counter electrode voltage, may be representative of an external impact to the electronics of the analyte monitoring device. An external impact may be an example of a permanent fault.

When the correlation between the counter electrode voltage and the sensing current is determined, the analyte monitoring device 110 (e.g., the controller) responds by applying a mode of operation consistent with the fault. For example, based on the identified characteristic of the counter electrode voltage and the correspondence of the counter electrode voltage and the sensing current, a mode of operation is applied to the microneedle array-based analyte monitoring device.

In some variations, the mode of operation includes disregarding the sensing current if the changes in the counter electrode voltage correspond with the changes in the sensing current and if the rate of change of the counter electrode voltage exceeds a threshold rate of change. As described herein, this may be representative of pressure-induced signal attenuation. When the pressure-induced signal attenuation is removed from the counter electrode voltage and the sensing current (e.g., the rate of change of the counter electrode voltage does not exceed the threshold rate of change), the sensing current is no longer disregarded as the fault has been remedied.

In some variations, the mode of operation includes discontinuing application of a potential between the working electrode and the reference electrode if the changes in the counter electrode voltage correspond with the changes in the sensing current and if the lower compliance limit of the counter electrode voltage meets a threshold compliance limit. The threshold compliance limit being reached is an indication of a permanent fault, and the bias potential is removed to stop operation.

In some variations, the mode of operation includes discontinuing application of a potential between the working electrode and the reference electrode if the changes in the counter electrode voltage deviate from the changes in the sensing current and if the rate of change of the counter electrode voltage exceeds a threshold rate of change. This is an indication of a permanent fault, and the bias potential is removed to stop operation.

As further described herein, the reference electrode functions to provide a reference potential for the three-electrode electrochemical system implemented by the analyte monitoring device 110. The electrical potential at which the working electrode is biased is referenced to the reference electrode. A fixed, time-varying, or at least controlled potential relationship is established between the working and reference electrodes, and within practical limits no current is sourced from or sinked to the reference electrode. To implement such a three-electrode electrochemical system, the analyte monitoring device 110 includes a potentiostat or an electrochemical analog front end (e.g., an analog front end) to maintain a fixed potential relationship between the working electrode and the reference electrode within the three-electrode electrochemical system, while permitting the counter electrode to dynamically swing to potentials required to sustain the redox reaction of interest. Biasing the electrochemical system with the potentiostat or the analog front end to establish the electrical potential relationship between the working electrode and the reference electrode drives the redox reaction at the working electrode and causes the counter electrode to sink an electrical current in an oxidative process or source an electrical current in a reductive process to sustain the redox reaction at the working electrode. The magnitude of the electrical current is proportional to the magnitude of the redox reaction occurring at the working electrode and to the impedance or resistance between the working electrode and the counter electrode. Biasing the electrochemical system results in formation of a voltage at the counter electrode, the value of which is also proportional to the magnitude of the redox reaction at the working electrode and to the impedance or resistance between the working electrode and the counter electrode.

The voltage at the counter electrode adjusts to the electrical potential to balance the redox reaction occurring at the working electrode when maintained at the electrical potential versus the reference electrode. Upon occurrence of a fault, in which one or more aspects of the analyte monitoring device 110 affects operation of the analyte monitoring device 110, the voltage at the counter electrode is modulated and reflective of the accumulated impedance between the working electrode and the counter electrode. By monitoring the voltage at the counter electrode, an indication of the impedance between the working electrode and the counter electrode may be determined. The three-electrode electrochemical system of the analyte monitoring device 110 can be modeled as an electrical network or system, including electrical components to correlate the voltage at the counter electrode with the impedance or resistance between the working electrode and the counter electrode, which can be correlated with one or more conditions, including fault types. By associating or characterizing the impedance with certain conditions including faults of the three-electrode electrochemical system, voltage values can be correlated with one or more faults.

Figure 10:
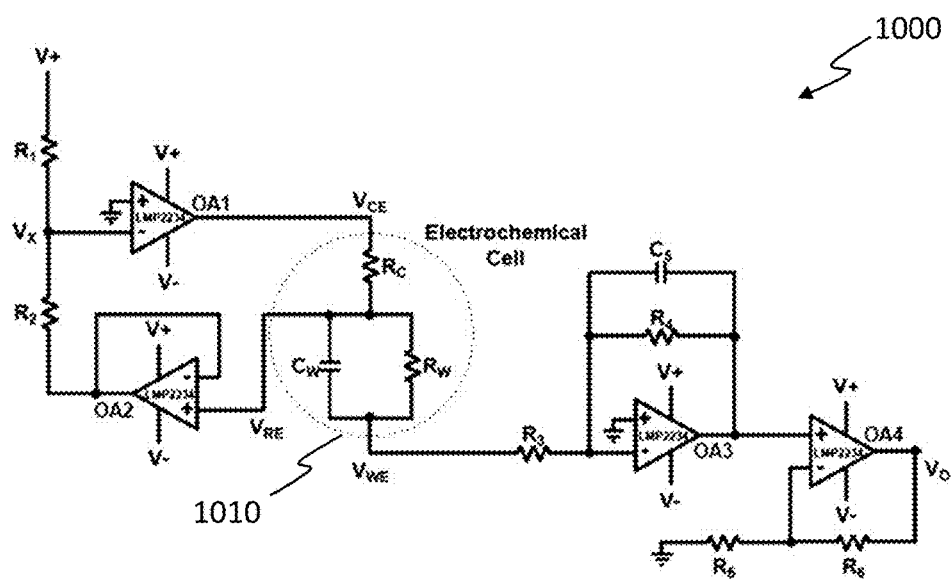
FIG. 10 depicts a representation of a potentiostat circuit of an analyte monitoring device.

FIG. 10 depicts a representation of a potentiostat circuit 1000 of the analyte monitoring device 110. The potentiostat circuit 1000 may be part of the sensor circuitry 124, depicted in and described with reference to FIG. 2A. The potentiostat circuit 1000 includes an electrochemical cell 1010 that connects the working electrode and the counter electrode of the three-electrode electrochemical system.

Figure 11:
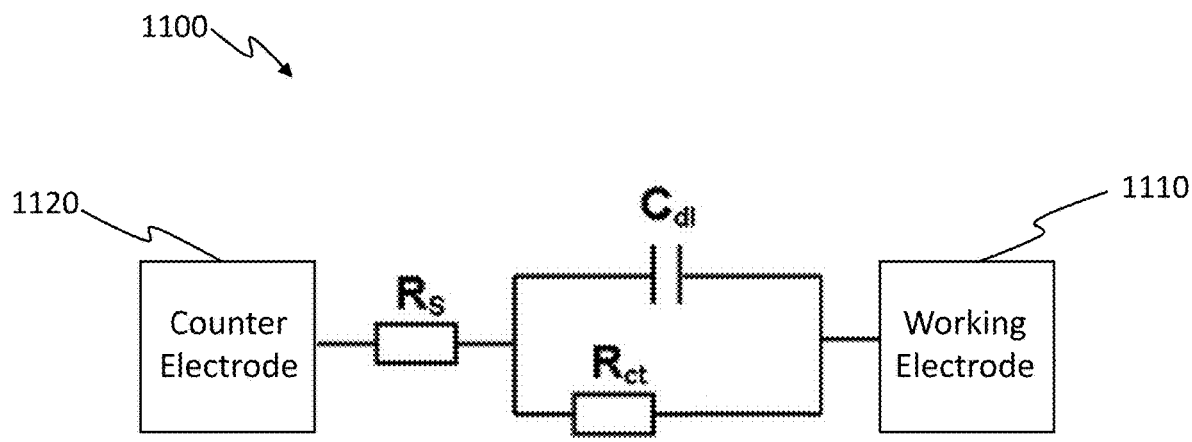
FIG. 11 depicts a Randles equivalent circuit representative of an electrochemical cell of an analyte monitoring device.

FIG. 11 depicts a Randles equivalent circuit 1100 that is representative of the electrochemical cell 1010 shown in FIG. 10A. The Randles equivalent circuit 1100 includes a solution resistance $R_s$ (also referred to as an uncompensated resistance $R_u$ or $R_\Omega$), a charge transfer resistance $R_{ct}$, and a double-layer capacitance Cal between a counter electrode 1120 and a working electrode 1110. The solution resistance $R_s$ is in series with a parallel combination of the charge transfer resistance $R_{ct}$ and the double-layer capacitance $C_{dl}$. The Randles equivalent circuit 1100 connects the terminals between the counter electrode 1120 and the working electrode 1110. The solution resistance $R_s$ is indicative of the level of ohmic contact between the counter electrode 1120 and the working electrode 1110 and may indicate the electrolytic content/ionic strength of the medium in which the analyte monitoring device 110 is operating (e.g., the fluid in which the electrodes of the microneedle array are positioned, such as, for example, interstitial fluid). The charge transfer resistance $R_{ct}$ is indicative of the magnitude of the electrochemical reaction occurring at the working electrode 1110. The double-layer capacitance $C_{dl}$ is indicative of surface morphology and constituency at the working electrode 1110 (e.g., the composition and makeup of the surface of the working electrode 1110).

The Randles equivalent circuit 1100 of the electrochemical cell 1010 of the analyte monitoring device 110 is a simplification of the redox reaction occurring within the electrochemical cell 1010. By modeling the electrochemical cell 1010 with the Randles equivalent circuit 1100, contributions from the solution resistance $R_s$, the charge-transfer resistance $R_{ct}$, and the double-layer capacitance $C_{dl}$ may be identified. A frequency response analysis, including amplitude and phase components, may be used to understand the impedance behavior of the electrochemical cell 1010 at DC ($\omega \to 0$) and at AC ($\omega \to \infty$) frequency perturbations. The voltage at the counter electrode 1120, in the DC case, provides an assessment of the overall resistive components of the system (e.g., $R_s + R_{ct}$) as $C_{dl}$ is assumed to have infinite impedance as $\omega \to 0$. In the other extreme, as $\omega \to \infty$, $C_{dl}$ approaches negligible impedance and $R_{ct}$ is bypassed. This allows the quantification of $R_s$ alone, which may be realized with an impulse or unit step function applied to the counter electrode 1120.

In the DC case ($\omega \rightarrow 0$), the voltage at the counter electrode 1120 is expected to swing to more extreme values, to the compliance voltage of the potentiostat, when additional current must be sourced or sinked to maintain the fixed potential relationship between the working electrode and the reference electrode. This is manifested via the counter electrode voltage migrating away from the voltage established at the working electrode 1110. In extreme cases, the voltage at the counter electrode 1120 approaches the compliance voltage, or the maximal voltage afforded by the circuit driving the counter electrode 1120. The manifestation of this mode of operation in the Randles equivalent circuit is a charge transfer resistance $R_{ct}$ that tends toward the value of the solution resistance $R_s$. In the DC case, this is an indication that one or more of the following faults is occurring: a short circuit generated between the working electrode and the counter electrode, a failure of the reference electrode's ability to maintain a stable thermodynamic potential, a compromise to a diffusion-limiting membrane, and a steady increase of the porosity of the sensing layer contained within analyte-selective sensor.

The counter electrode voltage approaches the voltage value in which the working electrode 1110 is maintained in scenarios in which the current requirements to sustain the fixed potential relationship between the working electrode and the reference electrode tend toward negligible values (e.g., inconsequential values of current flow through the system, $i \rightarrow 0$). The manifestation of this mode of operation in the Randles equivalent circuit is a charge transfer resistance $R_{ct}$ that tends toward infinity. In the DC case, this is an indication that one or more of the following faults is occurring: improper sensor insertion, improper access to a viable anatomic compartment, partial or complete occlusion of the sensor (e.g., due to biofouling/protein adsorption/collagen formation/encapsulation) such that analyte diffusion is attenuated, and a failure of the reference electrode's ability to maintain a stable thermodynamic potential.

Measurement of the voltage at the counter electrode may be achieved by a potentiostat, an electrochemical analog front end, or a converter, such as a voltage-sensitive or current-sensitive analog-to-digital converter (ADC).

Figure 12:
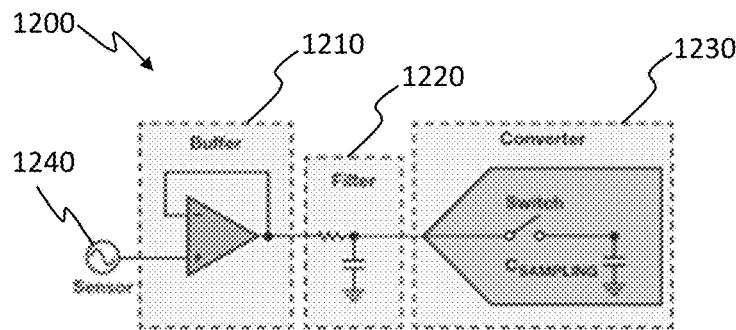
FIG. 12 depicts a measurement circuit of an analyte monitoring device.

In some instances, and as shown in a measurement circuit 1200 in FIG. 12, a buffer 1210 and a filter 1220 (e.g., a low-pass filter) may provide isolation from a converter 1230 to isolate the components from the counter electrode included in the electrochemical sensor 1240. In some implementations, a differential amplifier, a transimpedance amplifier, or a finite gain amplifier may be incorporated. The filter 1220 may be positioned before the converter 1230 to reduce high-frequency, low-frequency, both high-frequency and low-frequency, and/or band-limited signals from interfering with the measurement of the counter electrode voltage.

In some instances, a voltage arising at one or more working electrodes is measured and used to supplement and/or complement the fault identification. The working electrode voltage may be compared against a counter electrode voltage to assess and/or determine the fault. An analog-to-digital converter may be in electrical communication with the working electrode. In some implementations, a galvanostat is incorporated to establish a desired electrical current relationship between the working electrode and the counter electrode.

Scenarios where the voltage at a counter electrode approaches that of the voltage at the working electrode is indicative of an impedance or resistance value of an analyte sensor decaying to low levels, by merit of Ohm's Law (v=Zi, where Z is the accumulated impedance of the analyte sensor). This is an indication that any one or more of the following faults is occurring: a short circuit generated between the working electrode and the counter electrode, a failure of the reference electrode's ability to maintain a stable thermodynamic potential, a compromise to a diffusion-limiting membrane, or a steady increase of the porosity of the sensing layer contained within analyte-selective sensor. The counter electrode voltage approaches the working electrode voltage in situations in which the counter electrode voltage is swinging in a positive direction to support the level of current at the working electrode (e.g., the sensing current).

If the difference between the voltage at the counter electrode and the voltage at the working electrode increases, this is indicative of an impedance or resistance value of an analyte sensor increasing to very large values. This is an indication that any one or more of the following faults is occurring: improper sensor insertion, partial or complete occlusion of the sensor (e.g., due to biofouling/protein adsorption/collagen formation/encapsulation) such that analyte diffusion is attenuated, or a failure of the reference electrode's ability to maintain a stable thermodynamic potential. The difference between the counter electrode voltage and the working electrode voltage increasing occurs when the counter electrode voltage swings in a negative direction to support the sensing current.

Figure 13A:
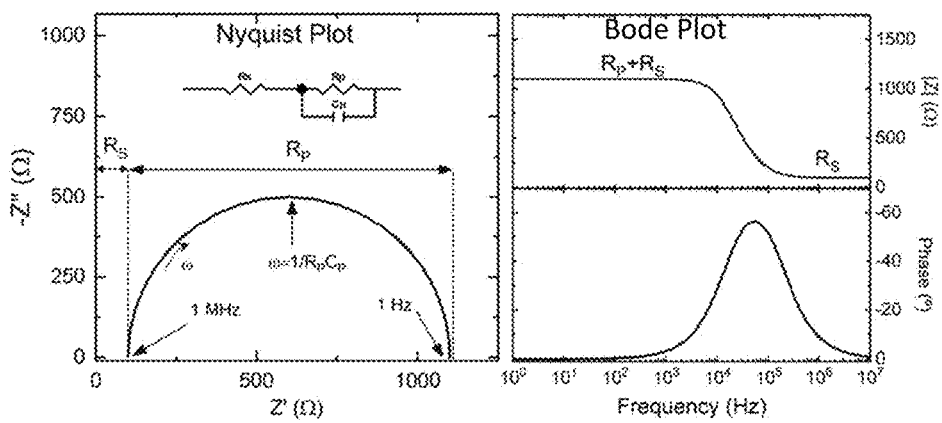
FIG. 13A is a representation of an electrochemical cell using both the Nyquist plot and the Bode plot formulation.

Thus, in some instances, a voltage is measured at the working electrode and the counter electrode to identify the fault. The voltage value of the counter electrode adjusts dynamically to support the prescribed current requirements of the analyte sensor, as shown in FIG. 13A. FIG. 13A is a representation of the electrochemical cell using both the Nyquist plot and the Bode plot formulation. The Bode plot illustrates the amplitude and phase response of the electrochemical cell.

Figure 13B:
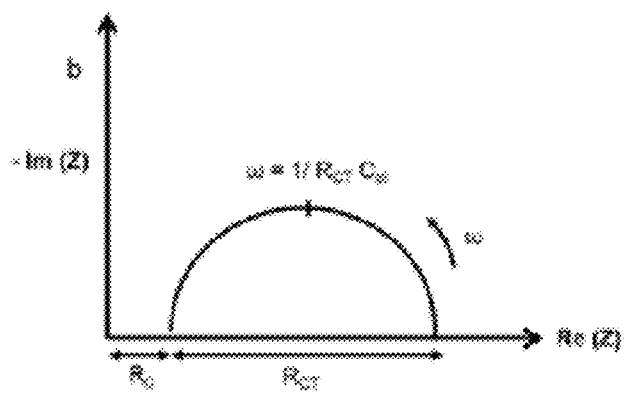
FIG. 13B is a representation of an electrochemical cell using a Nyquist plot formulation.

FIG. 13B is a Nyquist plot of the electrochemical cell, illustrating the real (Re{Z}) and imaginary (Im{Z}) components of the electrochemical impedance as radian frequency $\omega$ is varied. A zero imaginary component of the impedance is achieved in two cases according to the Randles equivalent circuit model: (1) when the radian frequency approaches $\infty$, allowing inference of the solution resistance ($R_s/R_\Omega$), and (2) when the radian frequency approaches 0, allowing inference of the charge-transfer resistance ($R_{ct}$) combined with the solution resistance $R_s$. Perturbing the electrochemical cell at both frequency extremes enables a full characterization of the real (resistive) components of the electrochemical cell. Assuming the electrochemical cell is purely capacitive, a semi-circle interpolation between both Im{Z} $\rightarrow 0$ intersection enables the calculation of a double-layer capacitance $C_{dl}$.

FIGS. 14-17 are example plots illustrating the relationship between current and corresponding counter electrode voltage in different fault situations, indicating the operational relationship between the sensing current and the counter electrode voltage. The example plots may be used to provide indications of sensor impedance changes between the counter electrode and the working electrode.

Figure 14:
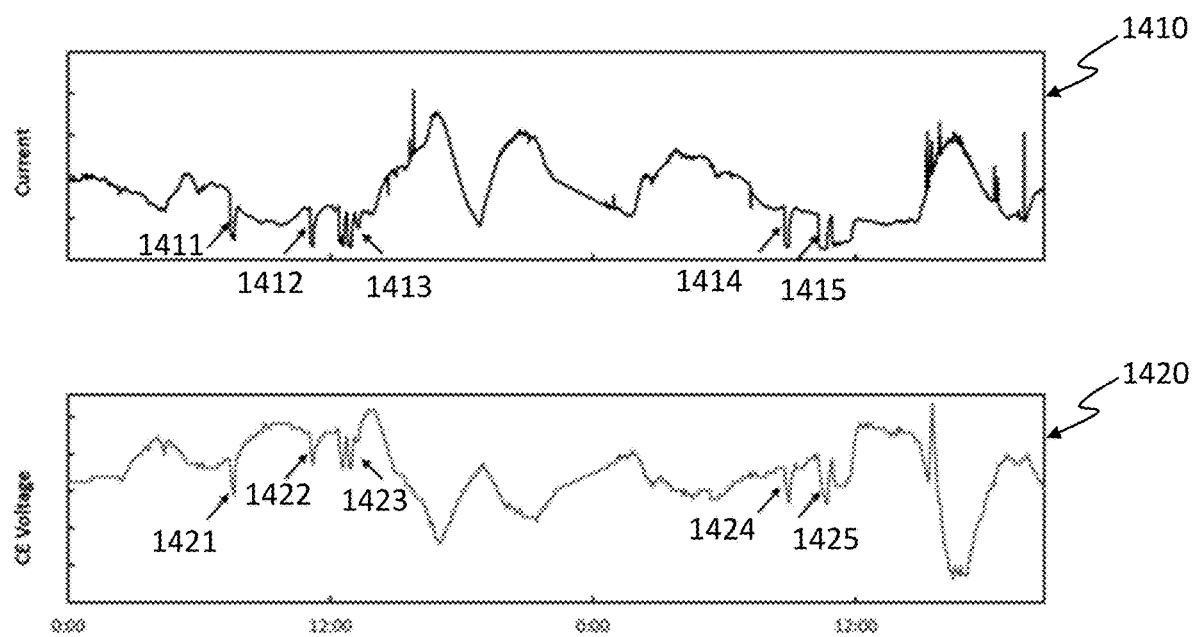
FIGS. 14-17 are plots of current and corresponding voltage at a counter electrode, depicting fault detection aspects.

FIG. 14 includes a sensing current plot 1410 and a corresponding counter electrode voltage plot 1420, versus time. During normal operation (e.g., before points 1411, 1421 and between points 1413, 1423 and points 1414, 1424), as the sensor current changes, the counter electrode voltage changes in an equal or near equal but opposite rate of change, which is visually depicted in the plots 1410 and 1420 as a mirrored response. During normal operation in which no faults are exhibited, the counter electrode voltage rate of change and the sensing current rate of change may be near equal or substantially equal. For example, a difference of up to about 5% may exist between the rates of change. In some variations, a difference of up to 10% may exist between the rates of change. The difference between the counter electrode voltage rate of change and the sensing current rate of change may vary, within the near equal or substantially equal range of up to 5% or in some instances up to 10%, during normal operation.

Faults are indicated at points 1421, 1422, 1423, 1424, and 1425 in the counter electrode voltage and correspond, respectively, to points 1411, 1412, 1413, 1414, and 1415 in the sensing current. The faults at points 1421, 1422, 1423, 1424, and 1425 are representative of pressure-induced signal attenuations and are identified by deviation in the correspondence between the counter electrode voltage and the sensing current. As shown in the plots 1410 and 1420, at the faults, the counter electrode voltage corresponds to the sensing current with an equal or near equal rate of change. For example, the rates of change may differ between one another by up to 5% or in some instances up to 10%.

Figure 15:
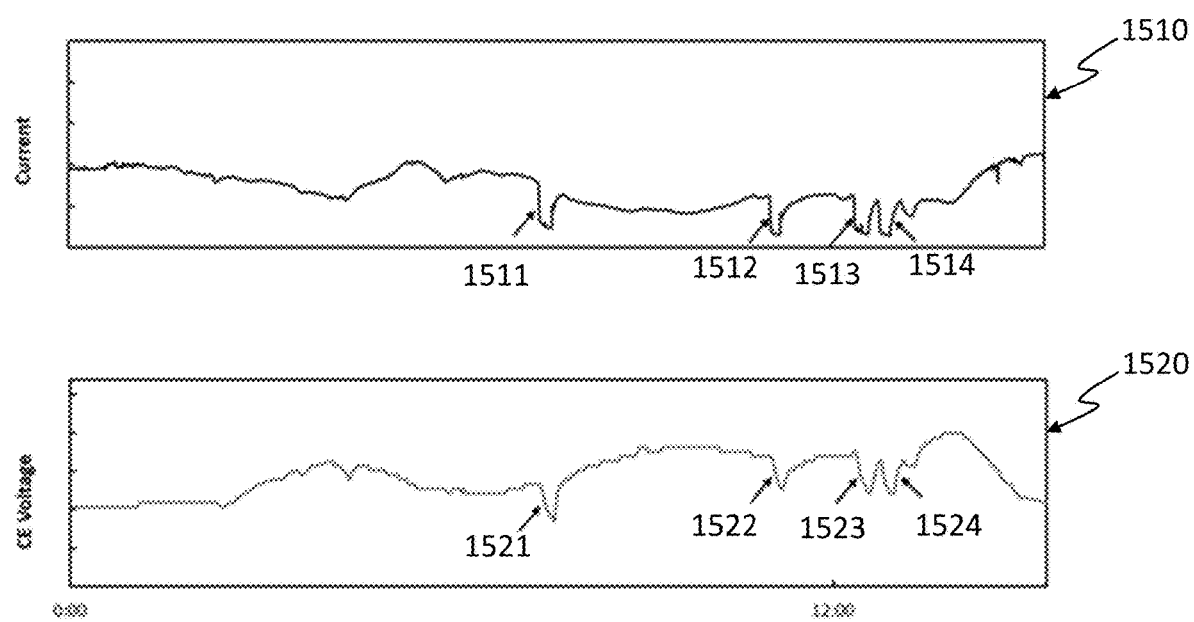

FIG. 15 (similar to FIG. 14) includes a current plot 1510 and a corresponding counter electrode voltage plot 1520, versus time. During normal operation (e.g., before points 1511,1521 and between points 1511, 1521 and points 1512, 1522), as the sensor current changes, the counter electrode voltage changes in an equal but opposite rate of change, which is visually depicted in the plots 1510 and 1520 as a mirrored response. During normal operation in which no faults are exhibited, the counter electrode voltage rate of change and the sensing current rate of change may be near equal or substantially equal. For example, a difference of up to about 5% may exist between the rates of change. In some variations, a difference of up to 10% may exist between the rates of change. The difference between the counter electrode voltage rate of change and the sensing current rate of change may vary, within the near equal or substantially equal range of up to 5% or in some instances up to 10%, during normal operation.

Faults are indicated at points 1521, 1522, 1523, and 1524 in the counter electrode voltage and correspond, respectively, to points 1511, 1512, 1513, and 1514 in the sensing current. The faults at points 1521, 1522, 1523, and 1524 are representative of pressure-induced signal attenuations and are identified by deviation in the correspondence between the counter electrode voltage and the sensing current. As shown in the plots 1510 and 1520, at the faults, the counter electrode voltage corresponds to the sensing current with an equal or near equal rate of change. For example, the rates of change may differ between one another by up to 5% or in some instances up to 10%.

Figure 16:
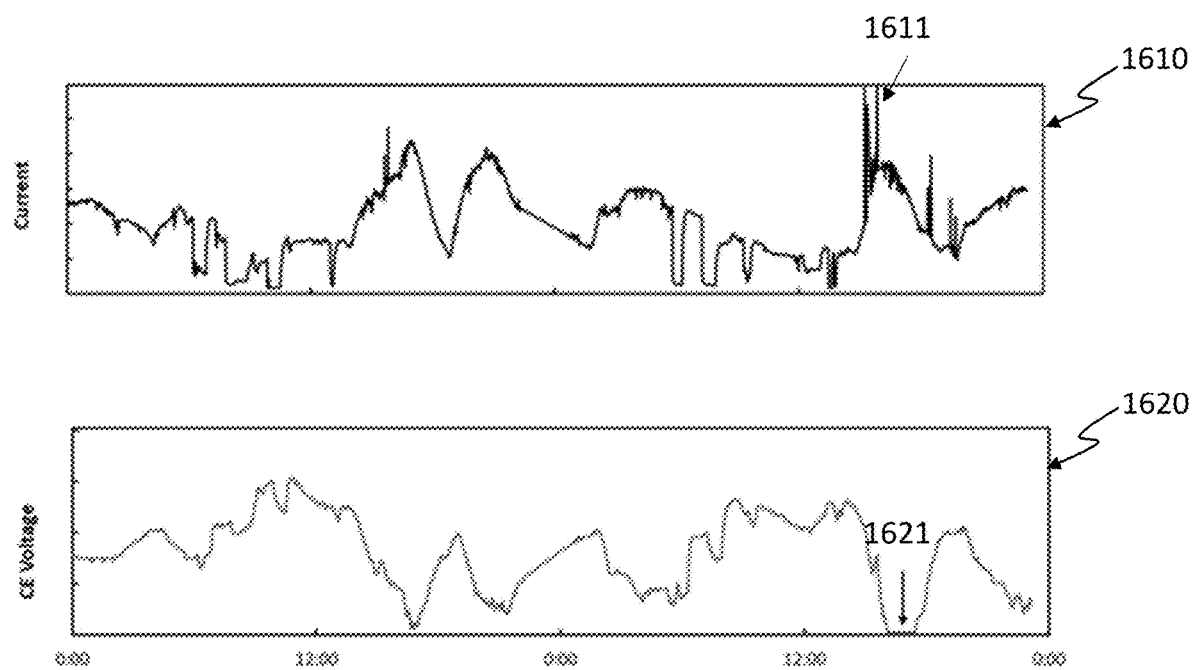

FIG. 16 includes a current plot 1610 and a corresponding counter electrode voltage plot 1620, versus time. During normal operation (e.g., before points 1621, 1611), as the sensor current changes, the counter electrode voltage changes in an equal or near equal but opposite rate of change, which is visually depicted in the plots 1610 and 1620 as a mirrored response. During normal operation in which no faults are exhibited, the counter electrode voltage rate of change and the sensing current rate of change may be near equal or substantially equal. For example, a difference of up to about 5% may exist between the rates of change. In some variations, a difference of up to 10% may exist between the rates of change. The difference between the counter electrode voltage rate of change and the sensing current rate of change may vary, within the near equal or substantially equal range of up to 5% or in some instances up to 10%, during normal operation.

The counter electrode voltage reaching a lower compliance limit at point 1621 is an indication of a fault. The point 1621 may correspond to a preceding current spike at point 1611 in the sensor current, but in some instances, it may not be a clear correlation between the counter electrode voltage and the sensing current. The fault at 1621, based on the lower compliance limit being reached, is representative of changes in the physiologic environment surrounding the sensor or changes in the sensor surface.

Figure 17:
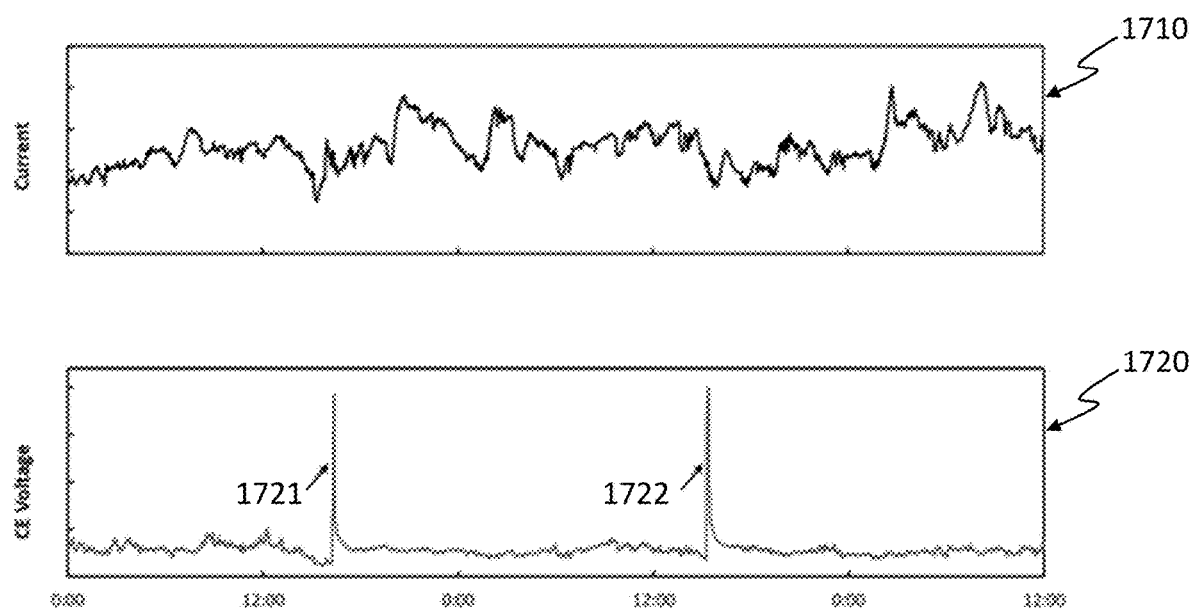

FIG. 17 includes a current plot 1710 and a corresponding counter electrode voltage plot 1720, versus time. Points 1721 and 1722, representative of faults due to the rapid rate of change exhibited, are indicated in the counter electrode voltage and, as shown, are unrelated to current of the analyte monitoring device. As the current is not experiencing substantial fluctuations or unexpected variations, the points 1721 and 1722 are indications of faults unrelated to current of the analyte monitoring device and are instead correlated to external environmental influences, such as external impact to the electronics of the analyte monitoring device.

Figure 18:
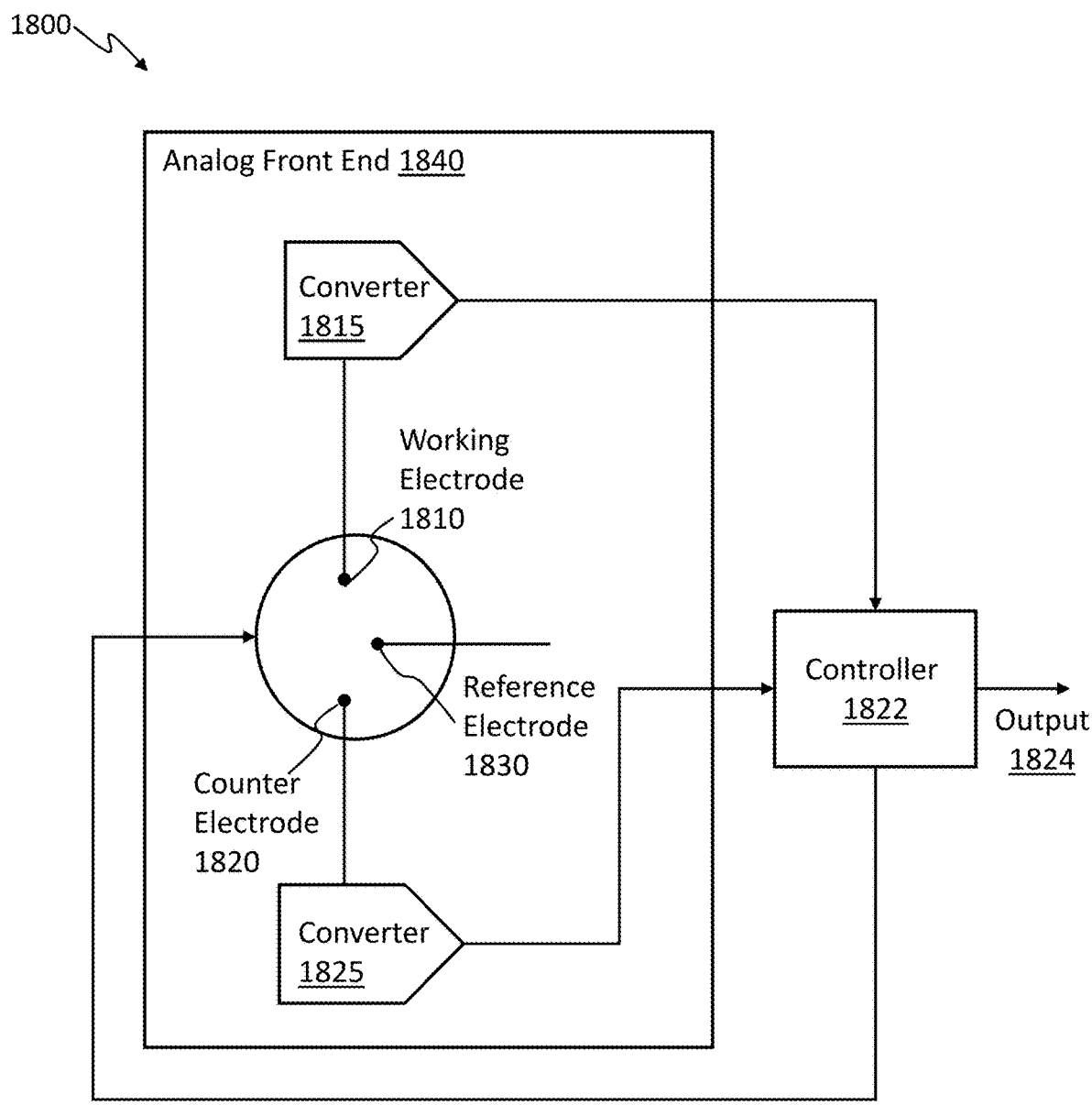
FIG. 18 depicts an illustrative schematic of an analyte monitoring device.

FIG. 18 depicts an illustrative schematic of a fault detection and diagnostics system 1800 for monitoring the counter electrode voltage and the working electrode voltage according to the described implementations. Aspects of the fault detection and diagnostics system 1800 may be incorporated in the analyte monitoring device 110. An analog front end 1840, as described herein and which maintains a fixed potential relationship between the working electrode 1810 and the reference electrode 1830 within the electrochemical system while permitting the counter electrode 1820 to dynamically swing to potentials required to sustain the redox reaction of interest at the working electrode, is included. A converter 1815 coupled to the working electrode 1810 is optionally provided to convert the working electrode voltage. A converter 1825 coupled to the counter electrode 1820 is provided to convert the counter electrode voltage. In some instances, one converter may be provided and coupled to each of the working electrode 1810 and the counter electrode 1820 for converting the voltages. The converter 1815, the converter 1825, and/or the single converter may be an analog to digital converter.

The digitized voltage signals are transmitted to a controller 1822 coupled to each converter. In some instances, the controller 122 shown in and described with reference to FIG. 2A may incorporate operational aspects of the controller 1822. The controller 1822 may be a separate component. In some instances, the controller 122 is incorporated in place of the controller 1822. The controller 1822 (and/or the controller 122) process the counter electrode voltage, the sensing current, and optionally the working electrode voltage to identify faults and associated modes of operation, according to aspects described herein. The controller 1822 may provide instructions or corrective signals to the three-electrode electrochemical system and may provide an output 1824 to alert the user of the faults and optionally the mode of operation. The output 1824 may be provided on a user interface of the analyte monitoring device and/or may be communicated (e.g., wirelessly through near-field communication, Bluetooth, or other wireless protocol) to a remote device and/or remote server.

In some variations, more than one working electrode is incorporated and used for detecting an analyte. For example, in the microneedle array configurations 900H, 900I, and/or 900J, shown in FIGS. 9H, 9I, and 9J, more than one working electrode and more than one counter electrode are incorporated. In variations in which more than one counter electrode are incorporated, the counter electrodes are shorted together such that one cumulative counter electrode voltage is monitored as the shorted together counter electrodes together act as one counter electrode.

With more than one working electrode, each additional working electrode generates a respective sensing current. In some variations, a correlation between the counter electrode voltage and each working electrode sensing current may be determined. As each working electrode is positioned on a separate and discrete microneedle in the microneedle array, faults that arise may not be consistent between the working electrodes. For example, electrode membrane degradation and biorecognition element degradation may vary across the plurality of working electrodes. Additionally, with respect to improper placement or insertion, in some instances the working electrodes may experience different insertion depths such that while one or more working electrodes are sufficiently inserted, others may not be. Pressure attenuations may also, in some instances, affect the working electrodes differently. Therefore, based on the differences that can occur across the microneedle array, it may be useful to separately monitor and analyze the counter electrode voltage against each working electrode sensing current. The separate monitoring and analysis may serve to provide an indication of a fault at one or more working electrodes. In some variations, when one fault is identified, a corresponding mode of operation is applied.

If more than one fault is identified and the faults are different, the mode of operation to discontinue application of a potential between the working electrode and the reference electrode takes a priority over the mode of operation to blank and/or disregard sensing data. In some variations, if a fault is detected at one working electrode but one or more additional working electrodes are operating according to normal operation (e.g., no fault detected), the potential applied at the working electrode exhibiting a fault may be discontinued while allowing operation to continue with the remaining working electrodes. In some variations, a minimum number of operational working electrodes may be defined such that operation of the analyte monitoring device continues if the number of operational working electrodes meets or exceeds the minimum number.

In some variations, a combined sensing current is based on the working electrode sensing currents being combined. For example, the sensing current from each of the working electrodes may be averaged to form a combined sensing current. The combined sensing current may be used with the counter electrode voltage, as described herein, to determine faults and modes of operation of the analyte monitoring device.

Additional details related to the Randles equivalent model are provided. The impedance Z of the Randles equivalent model is given by the relation:

$$Z = R_s + R_{ct} \| C_{dl} \quad [1]$$

Expanding this relation to represent the impedance as a function of radian frequency $\omega$:

$$\tilde{Z} = R_s + \frac{R_{ct}}{1 + j\omega R_{ct} C_{dl}} \quad [2]$$

At the DC case (zero frequency), the impedance is given by:

$$\tilde{Z}(\omega \to 0) = R_s + R_{ct} \quad [3]$$

At the AC case (high frequency extreme), the impedance is given by:

$$\tilde{Z}(\omega \to \infty) = R_s \quad [4]$$

Recasting equation 2:

$$\tilde{Z} = R_s + \frac{R_{ct}}{1 + \omega^2 R_{ct}^2 C_{dl}^2} - j \frac{\omega R_{ct}^2 C_{dl}}{1 + \omega^2 R_{ct}^2 C_{dl}^2} \quad [5]$$

The real and imaginary components of the impedance given in equation 5 may be easily identified as:

$$\text{Re}\{\tilde{Z}\} = R_s + \frac{R_{ct}}{1 + \omega^2 R_{ct}^2 C_{dl}^2} \quad [6]$$

$$\text{Im}\{\tilde{Z}\} = -\frac{\omega^2 R_{ct}^2 C_{dl}^2}{1 + \omega^2 R_{ct}^2 C_{dl}^2} \quad [7]$$

Given a substitution:

$$\xi = 1 + \omega^2 R_{ct}^2 C_{dl}^2 \quad [8]$$

The amplitude response of the system is given by:

$$|\tilde{Z}| = \sqrt{[\text{Re}\{\tilde{Z}\}]^2 + [\text{Im}\{\tilde{Z}\}]^2} = \sqrt{R_s^2 + \frac{R_{ct}}{\xi}\left(2R_s + \frac{R_{ct}}{\xi} + \frac{\omega^2 R_{ct}^3 C_{dl}^2}{\xi}\right)} \quad [9]$$

The phase response is accordingly computed:

$$\varphi = \tan^{-1}\left(\frac{\text{Im}\{\tilde{Z}\}}{\text{Re}\{\tilde{Z}\}}\right) = \tan^{-1}\left(-\frac{\omega R_{ct}^2 C_{dl}}{R_s \xi + R_{ct}}\right) \quad [10]$$

The current supported by the electrochemical reaction $i_{CELL}$ may be computed by applying Kirchoff's Voltage Law to the Randles cell:

$$i_{CELL}(\omega) = \frac{V_{CE} - V_{WE}}{\tilde{Z}} = \frac{V_{CE} - V_{WE}}{R_s + \frac{R_{ct}}{1 + j\omega R_{ct} C_{dl}}} \quad [11]$$

The counter electrode voltage, $V_{CE}$, may be computed by reformulating the above relation:

$$V_{CE} = V_{WE} + i_{CELL}(\omega)\left[R_s + \frac{R_{ct}}{1 + j\omega R_{ct} C_{dl}}\right] \quad [12]$$

The current may be a positive or negative quantity depending on the configuration of the potentiostat and whether the electrochemical reaction is undergoing oxidation or reduction. In the provided model and current worked equations, it is assumed that the current flows from the counter electrode (held at highest potential) through the electrochemical cell and into the working electrode, which is held at a lower potential (e.g., ground-referenced); this model assumes a reduction reaction (e.g., current flows into the working electrode and thus acts as an electron source). It is also possible for the counter electrode to be held at a lower potential than the working electrode (in oxidation), causing the current to flow from the working electrode into the counter electrode. In this case, the working electrode acts as an electron sink.

For the DC case:

$$V_{CE}=V_{WE}+i_{CELL}[R_s+R_{ct}] \quad [13]$$

For a given $R_s$ and $R_{ct}$, $V_{CE}$ will track $i_{CELL}$. For a finite charge transfer resistance $R_{ct}$:

$$\lim_{R_s \to \infty} V_{CE} = \infty \quad [14]$$

This is the compliance voltage limit of the potentiostat. In this scenario, there is no ohmic connection between the counter electrode and working electrode. Likewise:

$$\lim_{R_s \to 0} V_{CE} = V_{WE} + i_{CELL}R_{ct} \quad [15]$$

This represents the ideal operating condition for an electrochemical system. This is achieved by operating in a medium of sufficient electrolytic/ionic strength (e.g., buffer solution or a physiological fluid of a wearer). Likewise, for a finite solution resistance $R_s$:

$$\lim_{R_{ct} \to \infty} V_{CE} = V_{WE} \quad [16]$$

In other words, the counter electrode voltage will approach the working electrode voltage as the current through the electrochemical cell, $i_{CELL}$, approaches zero due to an infinite charge-transfer resistance. The practical manifestation of this is a complete passivation of the working electrode surface such that no current can flow; an ideal double-layer capacitor is thus formed. As for the case when the said charge transfer resistance approaches zero:

$$\lim_{R_{ct} \to 0} V_{CE} = V_{WE} + i_{CELL}R_s \quad [17]$$

The current through the electrochemical cell becomes invariant of the charge transfer process (e.g., as in an electrolysis reaction). Instead, the counter electrode will track the current flowing through the electrochemical cell (assuming the solution resistance/electrolytic content remains constant throughout the electrolysis).

In the AC case, as the frequency tends towards extreme values:

$$\lim_{\omega \to \infty} V_{CE} = V_{WE} + i_{CELL}R_s \quad [18]$$

The current through the electrochemical cell becomes invariant of the charge transfer process (e.g., as in an electrolysis reaction). Similarly, in the DC case, as the frequency tends towards zero:

$$\lim_{\omega \to 0} V_{CE} = V_{WE} + i_{CELL}[R_s + R_{ct}] \quad [19]$$

This is the same as equation 13.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

The invention claimed is:

1. A microneedle array-based analyte monitoring device, comprising:
    a working electrode comprising an electrochemical sensing coating configured to generate a sensing current indicative of a redox reaction of an analyte at a surface of the working electrode, the working electrode positioned on a surface of a distal portion of a first microneedle in a microneedle array;
    a reference electrode positioned on a surface of a distal portion of a second microneedle in the microneedle array;
    a counter electrode positioned on a surface of a distal portion of a third microneedle in the microneedle array;
    an analog front end configured to maintain a fixed potential relationship between the working electrode and the reference electrode and to allow potential of the counter electrode to swing to sustain the redox reaction at the working electrode;
    a controller in communication with the analog front end and configured to:
        monitor a counter electrode voltage at the counter electrode;
        identify a characteristic of the counter electrode voltage that meets or exceeds a threshold value;
        determine, in response to identifying the characteristic of the counter electrode voltage that exceeds the threshold value, a correlation between the counter electrode voltage and the sensing current; and
        apply, based on the characteristic of the counter electrode voltage and the correlation, a mode of operation to the microneedle array-based analyte monitoring device.

2. The microneedle array-based analyte monitoring device of claim 1, wherein the characteristic of the counter electrode voltage comprises one or more of a rate of change of the counter electrode voltage or a lower compliance limit of the counter electrode voltage. determine, in response to identifying the characteristic of the counter electrode voltage that exceeds the threshold value, a correlation between the counter electrode voltage and the respective sensing current.

3. The microneedle array-based analyte monitoring device of claim 2, wherein changes in the counter electrode voltage and changes in the sensing current are indicative of the correlation between the counter electrode voltage and the sensing current.

4. The microneedle array-based analyte monitoring device of claim 3, wherein the mode of operation comprises disregarding the sensing current if the changes in the counter electrode voltage correspond with the changes in the sensing current and if the rate of change of the counter electrode voltage exceeds a threshold rate of change.

5. The microneedle array-based analyte monitoring device of claim 4, wherein the controller is further configured to interrupt the mode of operation of disregarding the sensing current, in response to a subsequent determination that the rate of change of the counter electrode voltage does not exceed the threshold rate of change.

6. The microneedle array-based analyte monitoring device of claim 3, wherein the mode of operation comprises discontinuing application of a potential between the working electrode and the reference electrode if the lower compliance limit of the counter electrode voltage meets a threshold compliance limit.

7. The microneedle array-based analyte monitoring device of claim 3, wherein the mode of operation comprises discontinuing application of a potential between the working electrode and the reference electrode if the changes in the counter electrode voltage deviate from the changes in the sensing current and if the rate of change of the counter electrode voltage exceeds a threshold rate of change.

8. The microneedle array-based analyte monitoring device of claim 1, further comprising:
one or more additional working electrodes, each of the one or more additional working electrodes generating a respective sensing current;
wherein the controller is further configured to:
determine, in response to identifying the characteristic of the counter electrode voltage that exceeds the threshold value, a correlation between the counter electrode voltage and the respective sensing current.

9. The microneedle array-based analyte monitoring device of claim 8, wherein the mode of operation is further based on the correlation between the counter electrode voltage and the respective sensing current.

10. The microneedle array-based analyte monitoring device of claim 9, wherein the sensing current at the working electrode and the respective sensing current at the one or more additional working electrodes are combined to determine a combined correlation.

11. A method, comprising:
monitoring a counter electrode voltage at a counter electrode of a microneedle array-based analyte monitoring device, the counter electrode positioned on a surface of a distal portion of a first microneedle in the microneedle array;
identifying a characteristic of the counter electrode voltage that meets or exceeds a threshold value;
determining, in response to identifying the characteristic of the counter electrode voltage that exceeds the threshold value, a correlation between the counter electrode voltage and a sensing current, the sensing current generated at a surface of a working electrode of the microneedle array-based analyte monitoring device; and
applying, based on the characteristic of the counter electrode voltage and the correlation, a mode of operation to the microneedle array-based analyte monitoring device;
wherein the working electrode comprises an electrochemical sensing coating configured to generate the sensing current indicative of a redox reaction of an analyte at the surface of the working electrode, the working electrode positioned on a surface of a distal portion of a second microneedle in a microneedle array;
wherein the microneedle array-based analyte monitoring device further comprises a reference electrode positioned on a surface of a distal portion of a third microneedle in the microneedle array, and an analog front end configured to maintain a fixed potential relationship between the working electrode and the reference electrode and to allow potential of the counter electrode to swing to sustain the redox reaction at the working electrode.

12. The method of claim 11, wherein the characteristic of the counter electrode voltage comprises one or more of a rate of change of the counter electrode voltage or a lower compliance limit of the counter electrode voltage.

13. The method of claim 12, wherein changes in the counter electrode voltage and changes in the sensing current are indicative of the correlation between the counter electrode voltage and the sensing current.

14. The method of claim 13, wherein the mode of operation comprises disregarding the sensing current if the changes in the counter electrode voltage correspond with the changes in the sensing current and if the rate of change of the counter electrode voltage exceeds a threshold rate of change.

15. The method of claim 14, wherein the mode of operation of disregarding the sensing current is interrupted in response to a subsequent determination that the rate of change of the counter electrode voltage does not exceed the threshold rate of change.

16. The method of claim 13, wherein the mode of operation comprises discontinuing application of a potential between the working electrode and the reference electrode if the lower compliance limit of the counter electrode voltage meets a threshold compliance limit.

17. The method of claim 13, wherein the mode of operation comprises discontinuing application of a potential between the working electrode and the reference electrode if the changes in the counter electrode voltage deviate from the changes in the sensing current and if the rate of change of the counter electrode voltage exceeds a threshold rate of change.

18. The method of claim 11, wherein the microneedle array-based analyte monitoring device further comprises one or more additional working electrodes, each of the one or more additional working electrodes generating a respective sensing current;
the method further comprising determining, in response to identifying the characteristic of the counter electrode voltage that exceeds the threshold value, a correlation between the counter electrode voltage and the respective sensing current.

19. The method of claim 18, wherein the mode of operation is further based on the correlation between the counter electrode voltage and the respective sensing current.

20. The method of claim 19, wherein the sensing current at the working electrode and the respective sensing current at the one or more additional working electrodes are combined to determine a combined correlation.

* * * * *